United States Patent
Bonnet et al.

(10) Patent No.: US 10,596,536 B2
(45) Date of Patent: Mar. 24, 2020

(54) COMPOSITION COMPRISING HF AND 3,3,3-TRIFLUORO-2-CHLOROPROPENE

(71) Applicant: ARKEMA FRANCE, Colombes (FR)

(72) Inventors: Philippe Bonnet, Lyons (FR); Bertrand Collier, Saint-Genis-Laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 118 days.

(21) Appl. No.: 15/858,005

(22) Filed: Dec. 29, 2017

(65) Prior Publication Data

US 2018/0126348 A1 May 10, 2018

Related U.S. Application Data

(63) Continuation of application No. 14/773,537, filed as application No. PCT/FR2014/050368 on Feb. 24, 2014, now Pat. No. 9,889,416.

(30) Foreign Application Priority Data

Mar. 20, 2013 (FR) ..................... 13 52484

(51) Int. Cl.
| | | |
|---|---|---|
| *C11D 7/50* | (2006.01) | |
| *B01F 17/00* | (2006.01) | |
| *C07C 21/18* | (2006.01) | |
| *C09K 3/30* | (2006.01) | |
| *C01B 7/19* | (2006.01) | |
| *B01D 53/26* | (2006.01) | |
| *C09G 1/06* | (2006.01) | |
| *C09K 3/00* | (2006.01) | |
| *C09K 5/04* | (2006.01) | |
| *H01B 3/56* | (2006.01) | |

(52) U.S. Cl.
CPC .......... *B01F 17/0085* (2013.01); *B01D 53/26* (2013.01); *C01B 7/191* (2013.01); *C07C 21/18* (2013.01); *C09G 1/06* (2013.01); *C09K 3/00* (2013.01); *C09K 3/30* (2013.01); *C09K 5/04* (2013.01); *H01B 3/56* (2013.01); *C09K 5/044* (2013.01)

(58) Field of Classification Search
CPC ....................................................... C11D 7/505
USPC ....................................................... 510/408
See application file for complete search history.

(56) References Cited

U.S. PATENT DOCUMENTS

| | | | |
|---|---|---|---|
| 2009/0224207 A1 | 9/2009 | Pham et al. | |
| 2009/0256110 A1* | 10/2009 | Merkel ................ | C07C 21/18 |
| | | | 252/182.12 |
| 2010/0187088 A1 | 7/2010 | Merkel et al. | |
| 2011/0210289 A9 | 9/2011 | Merkel et al. | |
| 2012/0215039 A1* | 8/2012 | Hulse ................... | C07C 17/206 |
| | | | 570/160 |
| 2012/0222448 A1 | 9/2012 | Chaki et al. | |
| 2014/0012052 A1 | 1/2014 | Pham et al. | |
| 2015/0225317 A1 | 8/2015 | Kopkalli et al. | |
| 2015/0247675 A1 | 9/2015 | Nappa et al. | |
| 2016/0214914 A1 | 7/2016 | Merkel et al. | |
| 2017/0057892 A1 | 3/2017 | Wang et al. | |

FOREIGN PATENT DOCUMENTS

| | | |
|---|---|---|
| EP | 2 108 638 A1 | 10/2009 |
| WO | WO 2012/121876 A2 | 9/2012 |

OTHER PUBLICATIONS

International Search Report (PCT/ISA/210) dated Jun. 10, 2014, by the French Patent Office as the International Searching Authority for International Application No. PCT/FR2014/050368.

* cited by examiner

*Primary Examiner* — Gregory E Webb
(74) *Attorney, Agent, or Firm* — Buchanan Ingersoll & Rooney P.C.

(57) ABSTRACT

An azeotropic or quasi-azeotropic composition including hydrogen fluoride, 3,3,3-trifluoro-2-chloropropene and one or more (hydro)halogen-carbon compounds including between 1 and 3 carbon atoms. Also an azeotropic or quasi-azeotropic composition including hydrogen fluoride, 3,3,3-trifluoro-2-chloropropene, and one or more compounds selected from among 1,3,3,3-tetrafluoropropene, 1,1,1,2,2-pentafluoropropane, 2,3,3,3-tetrafluoropropene, 3,3,3-trifluoropropene, E-3,3,3-trifluoro-1-chloropropene, trifluoropropyne, 1,1,3,3-pentafluoropropane, 1,1,1,3,3-pentafluoropropane, 1,1,1,3,3-pentafluoropropene, 1,1,1,2,3-pentafluoropropene and 2-chloro,1,1,1,2-1 tetrafluoropropane.

16 Claims, No Drawings

COMPOSITION COMPRISING HF AND 3,3,3-TRIFLUORO-2-CHLOROPROPENE

CROSS REFERENCE TO RELATED APPLICATIONS

The present application is a continuation of U.S. application Ser. No. 14/773,537, filed on Sep. 8, 2015, which is a U.S. national stage of International Application No. PCT/FR2014/050368, filed on Feb. 24, 2014, which claims the benefit of French Application No. 13.52484, filed on Mar. 20, 2013. The entire contents of each of U.S. application Ser. No. 14/773,537, International Application No. PCT/FR2014/050368, and French Application No. 13.52484 are hereby incorporated herein by reference in their entirety.

TECHNICAL FIELD

The present invention relates to azeotropic or quasi-azeotropic compositions comprising 3,3,3-trifluoro-2-chloropropene and hydrogen fluoride. These compositions may originate from intermediate compositions in the production of 3,3,3-trifluoro-2-chloropropene and are generally useful in processes for recycling hydrogen fluoride.

SUMMARY

The manufacture of 3,3,3-trifluoro-2-chloropropene accompanied by a multitude of by-products, having a boiling point close to HCFO-1233xf, leads to relatively complex and expensive purification steps. The difficulty encountered during the purification of HCFO-1233xf generally implies an appreciable loss of desired product. Furthermore, these by-products may form azeotropic compositions with 3,3,3-trifluoro-2-chloropropene, making separation by distillation simple, very difficult, or even impossible.

Fluids comprising 3,3,3-trifluoro-2-chloropropene are promising for numerous applications in varied industrial fields, especially as reaction intermediate, heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

The subject of the present invention is an azeotropic or quasi-azeotropic composition comprising hydrogen fluoride, 3,3,3-trifluoro-2-chloropropene and one or more (hydro) halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2=CF-CF_3$
HFC-245cb: 1,1,1,2,2-pentafluoropropane or $CF_3-CF_2-CH_3$
HFO-1234zeE: E-1,3,3,3-tetrafluoropropene or $E-CF_3-CH=CHF$
HFO-1234zeZ: Z-1,3,3,3-tetrafluoropropene or $Z-CF_3-CH=CHF$
HFO-1243zf: 3,3,3-trifluoropropene or $CF_3-CH=CH_2$
HCFO-1233xf: 3,3,3-trifluoro-2-chloropropene or $CF_3-CCl=CH_2$
HCFO-1233zdE: E-3,3,3-trifluoro-1-chloropropene or $E-CF_3-CH=CHCl$
HCFO-1233zdZ: Z-3,3,3-trifluoro-1-chloropropene or $Z-CF_3-CH=CHCl$
HFO-1225yeZ: Z-1,1,1,2,3-pentafluoropropene or $Z-CHF=CF-CF_3$
HFO-1225yeE: E-1,1,1,2,3-pentafluoropropene or $E-CHF=CF-CF_3$
HFO-1225zc: 1,1,3,3,3-pentafluoropropene or $CF_2=CH-CF_3$
HFO-1225yc: 1,1,2,3,3-pentafluoropropene or $CF_2=CF-CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F-CCl=CF_2$
HCFO-1233xe: 1,3,3-trifluoro-2-chloropropene or $CHF_2-CCl=CHF$
HCFO-1233yb: 1,2,3-trifluoro-1-chloropropene or $CH_2F-CF=CFCl$
HCFO-1233yc: 1,1,2-trifluoro-3-chloropropene or $CH_2Cl-CF=CF_2$
HCFO-1233yd: 2,3,3-trifluoro-1-chloropropene or $CHF_2-CF=CHCl$
HCFO-1233ye: 1,2,3-trifluoro-3-chloropropene or $CHClF-CF=CHF$ HCFO-1233yf: 2,3,3-trifluoro-3-chloropropene or $CClF_2—CF=CH_2$ HCFO-1233zb: 1,3,3-trifluoro-1-chloropropene or $CHF_2—CH=CFCl$ HCFO-1233zc: 1,1,3-trifluoro-3-chloropropene or $CHClF—CH=CF_2$ HCFO-1233ze: 1,3,3-trifluoro-3-chloropropene or $CClF_2—CH=CHF$ HFO-1234yc: 1,1,2,3-tetrafluoropropene or $CF_2=CF—CH_2F$ HFO-1234ye: 1,2,3,3-tetrafluoropropene or $CHF=CF—CHF_2$ HFO-1234zc: 1,1,3,3-tetrafluoropropene or $CF_2=CH—CHF_2$ HCFO-1242: chlorodifluoropropene, or $C_3H_3F_2Cl$ HFO-1243yc: 1,1,2-trifluoropropene or $CH_3—CF=CF_2$ HFO-1243ye: 1,2,3-trifluoropropene or $CH_2F—CF=CHF$ HFO-1243yf: 2,3,3-trifluoropropene or $CHF_2—CF=CH_2$ HFO-1243zc: 1,1,3-trifluoropropene or $CH_2F—CH=CF_2$ HFO-1243ze: 1,3,3-trifluoropropene or $CHF_2—CH=CHF$ HCFO-1251: chlorofluoropropene, or $C_3H_4FCl$ HFO-1252: difluoropropene, or $C_3H_4F_2$ HFO-216: hexafluoropropene, or $C_3F_6Cl_2$ HCFO-217: chloroheptafluoropropane, or $C_3F_7Cl$ HFC-218: octafluoropropane, or $C_3F_8$ HCFC-225: dichloropentafluoropropane, or $C_3HF_5Cl_2$ HCFC-226: chlorohexafluoropropane, or $C_3HF_6Cl$ HFC-227: heptafluoropropane, or $C_3HF_7$ HCFC-234: dichlorotetrafluoropropane, or $C_3H_2F_4Cl_2$ HCFC-235: chloropentafluoropropane, or $C_3H_2F_5Cl$ HFC-236: hexafluoropropane, or $C_3H_2F_6$ HCFC-243: dichlorotrifluoropropane, or $C_3H_3F_3Cl_2$ HCFC-244: chlorotetrafluoropropane, or $C_3H_3F_4Cl$ HCFC-244bb: 2-chloro,1,1,1,2-tetrafluoropropane or $CF_3—CFCl—CH_3$ HFC-245fa: 1,1,1,3,3-pentafluoropropane or $CF_3—CH_2—CHF_2$ HFC-245ea: 1,1,2,3,3-pentafluoropropane or $CHF_2—CHF—CHF_2$ HFC-245eb: 1,1,1,2,3-pentafluoropropane or $CF_3—CHF—CH_2F$ HFC-245ca: 1,1,2,2,3-pentafluoropropane or $CHF_2—CF_2—CH_2F$ HCFC-253: chlorotrifluoropropane, or $C_3H_4F_3Cl$ HFC-254: tetrafluoropropane, or $C_3H_4F_4$ HCFC-262: Chlorodifluoropropane, or $C_3H_5F_2Cl$ HFC-263: trifluoropropane, or $C_3H_5F_3$ Trifluoropropyne: $CF_3—C≡CH$

DETAILED DESCRIPTION

The composition according to the invention may optionally be a mixture of one or more azeotropes and/or heteroazeotropes of ternary, quaternary, penternary systems, systems with six compounds, systems with seven compounds, systems with eight or more compounds.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,1,2-tetrafluoropropane, 1-chloro-1,1,2,3-tetrafluoropropane, 3-chloro-1,1,1,3-tetrafluoropropane, 1-chloro-1,3,3,3-tetrafluoropropane, pentafluoropropane, 1,1,1,2,2-pentafluoropropane, 1,1,2,2,3-pentafluoropropane, 1,1,2,3,3-pentafluoropropane, 1,1,1,2,3-pentafluoropropane, 1,1,1,3,3-pentafluoropentane, chlorotrifluoropropane, 2-chloro-1,2,3-trifluoropropane, 2-chloro-1,1,2-trifluoropropane, 1-chloro- 2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 2,3,3,3-tetrafluoropropene, 1,1,2,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

Preferably, the ternary compositions consisting essentially of HF—HFCO-1233xf-HFC-245fcb, HF—HFCO-1233xf-HCFC-244bb and HF—HCFO-1233xf-HFO-1230xa (1,1,2,3-tetrachloropropene) are excluded from the present invention.

A subject of the present invention is also an azeotropic or quasi-azeotropic composition comprising hydrogen fluoride, 3,3,3-trifluoro-2-chloropropene, and one or more compounds chosen from E-1,3,3,3-tetrafluoropropene, Z-1,3,3,3-tetrafluoropropene, 3,3,3-trifluoropropene, 2,3,3,3-tetrafluoropropene, E-3,3,3-trifluoro-1-chloropropene, trifluoropropyne, 1,1,1,3,3-pentafluoropropane, 1,1,1,3,3-pentafluoropropene, 1,1,1,2,2-pentafluoropropane, 2-chloro-1,1,1,2-tetrafluoropropane and 1,1,1,2,3-pentafluoropropene.

A subject of the present invention is also a composition comprising hydrogen fluoride, 3,3,3-trifluoro-2-chloropropene and at least one or more organic compounds chosen from E-3,3,3-trifluoro-1-chloropropene, E-1,3,3,3-tetrafluoropropene, Z-1,3,3,3-tetrafluoropropene, 3,3,3-trifluoropropene, 1,1,1,2,2-pentafluoropropane and 2,3,3,3-tetrafluoropropene.

According to one embodiment, the composition according to the invention comprises hydrogen fluoride, 3,3,3-trifluoro-2-chloropropene, E-1,3,3,3-tetrafluoropropene and optionally one or more compounds chosen from Z-1,3,3,3-tetrafluoropropene, 3,3,3-trifluoropropene, 2,3,3,3-tetrafluoropropene, E-3,3,3-trifluoro-1-chloropropene, trifluoropropyne, 1,1,1,3,3-pentafluoropropane, 1,1,1,3,3-pentafluoropropene, 1,1,1,2,2-pentafluoropropane, 2-chloro-1,1,1,2-tetrafluoropropane and 1,1,1,2,3-pentafluoropropene.

According to another embodiment, the composition according to the invention comprises hydrogen fluoride, 3,3,3-trifluoro-2-chloropropene, Z-1,3,3,3-tetrafluoropropene and optionally one or more compounds chosen from 3,3,3-trifluoropropene, 2,3,3,3-tetrafluoropropene, E-3,3,3-trifluoro-1-chloropropene, trifluoropropyne, 1,1,1,3,3-pentafluoropropane, 1,1,1,3,3-pentafluoropropene, 1,1,1,2,2-pentafluoropropane, 2-chloro-1,1,1,2-tetrafluoropropane and 1,1,1,2,3-pentafluoropropene.

According to one embodiment, the composition according to the invention comprises hydrogen fluoride, 3,3,3-trifluoro-2-chloropropene, 3,3,3-trifluoropropene and optionally one or more compounds chosen from 2,3,3,3-tetrafluoropropene, E-3,3,3-trifluoro-1-chloropropene, trifluoropropyne, 1,1,1,3,3-pentafluoropropane, 1,1,1,3,3-pentafluoropropene, 1,1,1,2,2-pentafluoropropane, 2-chloro-1,1,1,2-tetrafluoropropane and 1,1,1,2,3-pentafluoropropene.

According to another embodiment, the composition according to the invention comprises hydrogen fluoride, 3,3,3-trifluoro-2-chloropropene, 2,3,3,3-tetrafluoropropene and optionally one or more compounds chosen from E-3,3,3-trifluoro-1-chloropropene, trifluoropropyne, 1,1,1,3,3-pentafluoropropane, 1,1,1,3,3-pentafluoropropene, 1,1,1,2, 2-pentafluoropropane, 2-chloro,1,1,1,2-tetrafluoropropane and 1,1,1,2,3-pentafluoropropene.

According to another embodiment, the composition according to the invention comprises hydrogen fluoride, 3,3,3-trifluoro-2-chloropropene, E-3,3,3-trifluoro-1-chloropropene and optionally one or more compounds chosen from trifluoropropyne, 1,1,1,3,3-pentafluoropropane, 1,1,1,3,3-pentafluoropropene, 1,1,1,2,2-pentafluoropropane, 2-chloro-1,1,1,2-tetrafluoropropane and 1,1,1,2,3-pentafluoropropene.

According to one embodiment, the composition according to the invention comprises hydrogen fluoride, 3,3,3-trifluoro-2-chloropropene, trifluoropropyne and optionally one or more compounds chosen from 1,1,1,3,3-pentafluoropropane, 1,1,1,3,3-pentafluoropropene, 1,1,1,2,2-pentafluoropropane, 2-chloro,1,1,1,2-tetrafluoropropane and 1,1,1,2,3-pentafluoropropene.

According to another embodiment, the composition according to the invention comprises hydrogen fluoride, 3,3,3-trifluoro-2-chloropropene, 1,1,1,3,3-pentafluoropropane and optionally one or more compounds chosen from 1,1,1,3,3-pentafluoropropene, 1,1,1,2,2-pentafluoropropane, 2-chloro,1,1,1,2-tetrafluoropropane and 1,1,1,2,3-pentafluoropropene.

According to one embodiment, the composition according to the invention comprises hydrogen fluoride, 3,3,3-trifluoro-2-chloropropene, 1,1,1,3,3-pentafluoropropene and optionally one or more compounds chosen from 1,1,1,2,2-pentafluoropropane, 2-chloro,1,1,1,2-tetrafluoropropane and 1,1,1,2,3-pentafluoropropene.

According to one embodiment, the composition according to the invention comprises hydrogen fluoride, 3,3,3-trifluoro-2-chloropropene, 1,1,1,2,2-pentafluoropropane and optionally one or more compounds chosen from 2-chloro-1,1,1,2-tetrafluoropropane and 1,1,1,2,3-pentafluoropropene.

According to another embodiment according to the invention, the composition comprises hydrogen fluoride, 3,3,3-trifluoro-2-chloropropene, 2-chloro-1,1,1,2-tetrafluoropropane and optionally 1,1,1,2,3-pentafluoropropene.

According to one embodiment, the composition according to the invention comprises hydrogen fluoride, 3,3,3-trifluoro-2-chloropropene and 1,1,1,2,3-pentafluoropropene.

According to one embodiment, the composition according to the invention comprises hydrogen fluoride, 3,3,3-trifluoro-2-chloropropene, E-3,3,3-trifluoro-1-chloropropene and optionally one or more organic compounds chosen from E-1,3,3,3-tetrafluoropropene, Z-1,3,3,3-tetrafluoropropene, 3,3,3-trifluoropropene, 1,1,1,2,2-pentafluoropropane, 2,3,3,3-tetrafluoropropene, trifluoropropyne, 1,1,1,3,3-pentafluoropropene, 2-chloro-1,1,1,2-tetrafluoropropane, 1,1,1,3,3-pentafluoropropane and 1,1,1,2,3-pentafluoropropene.

According to one embodiment, the composition according to the invention comprises hydrogen fluoride, 3,3,3-trifluoro-2-chloropropene, E-1,3,3,3-tetrafluoropropene and optionally one or more compounds chosen from Z-1,3,3,3-tetrafluoropropene, 3,3,3-trifluoropropene, 1,1,1,2,2-pentafluoropropane, 2,3,3,3-tetrafluoropropene, trifluoropropyne, 1,1,1,3,3-pentafluoropropene, 2-chloro-1,1,1,2-tetrafluoropropane, 1,1,1,3,3-pentafluoropropane and 1,1,1,2,3-pentafluoropropene.

According to another embodiment, the composition according to the invention comprises hydrogen fluoride, 3,3,3-trifluoro-2-chloropropene, Z-1,3,3,3-tetrafluoropropene and optionally one or more organic compounds chosen from 3,3,3-trifluoropropene, 1,1,1,2,2-pentafluoropropane, 2,3,3,3-tetrafluoropropene, trifluoropropyne, 1,1,1,3,3-pentafluoropropene, 2-chloro-1,1,1,2-tetrafluoropropane, 1,1,1,3,3-pentafluoropropane and 1,1,1,2,3-pentafluoropropene.

According to one embodiment according to the invention, the composition comprises hydrogen fluoride, 3,3,3-trifluoro-2-chloropropene, 3,3,3-trifluoropropene and optionally one or more organic compounds chosen from 1,1,1,2,2-pentafluoropropane, 2,3,3,3-tetrafluoropropene, trifluoropropyne, 1,1,1,3,3-pentafluoropropene, 2-chloro-1, 1,1,2-tetrafluoropropane, 1,1,1,3,3-pentafluoropropane and 1,1,1,2,3-pentafluoropropene.

According to another embodiment, the composition according to the invention comprises hydrogen fluoride, 3,3,3-trifluoro-2-chloropropene, 1,1,1,2,2-pentafluoropropane and one or more organic compounds chosen from 2,3,3,3-tetrafluoropropene, trifluoropropyne, 1,1,1,3,3-pentafluoropropene, 2-chloro-1,1,1,2-tetrafluoropropane, 1,1,1,3,3-pentafluoropropane and 1,1,1,2,3-pentafluoropropene.

According to one embodiment, the composition according to the invention comprises hydrogen fluoride, 3,3,3-trifluoro-2-chloropropene, 2,3,3,3-tetrafluoropropene and one or more organic compounds chosen from trifluoropropyne, 1,1,1,3,3-pentafluoropropene, 2-chloro-1,1,1,2-tetrafluoropropane, 1,1,1,3,3-pentafluoropropane and 1,1,1,2,3-pentafluoropropene.

Irrespective of the embodiment, the composition preferably comprises from 1% to 85% and advantageously from 5% to 80% by weight of hydrogen fluoride and from 99% to 15% and advantageously from 20% to 95% by weight of the sum of the organic compounds; more particularly, the composition comprises from 1% to 85% by weight of hydrogen fluoride and from 99% to 15% by weight of the sum of the organic compounds (HCFO-1233xf and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, 3,3,3-trifluoro-2-chloropropene and a compound chosen from 2,3,3,3-tetrafluoropropene, 3,3,3-trifluoropropene, 1,3,3,3-tetrafluoropropene, 1,1,1,2,2-pentafluoropropane and E-3,3,3-trifluoro-1-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, 3,3,3-trifluoro-2-chloropropene and a compound chosen from trifluoropropyne, 1,1,1,3,3-pentafluoropropene, 2-chloro-1,1,1,2-tetrafluoropropane, 1,1,1,3,3-pentafluoropentane and Z-1,1,1,2,3-pentafluoropropene are characterized by a phase depleted in HF and a phase enriched in HF for at least isotherms at 0° C., 25° C. and 40° C.

The Applicant has observed the same phenomenon for compositions of hydrogen fluoride, 3,3,3-trifluoro-2-chloropropene comprising several compounds chosen from 2,3,3,3-tetrafluoropropene, 3,3,3-trifluoropropene, E-3,3,3-trifluoro-1-chloropropene, trifluoropropyne, 1,1,1,3,3-pentafluoropropene, 2-chloro-1,1,1,2-tetrafluoropropane and 1,1,1,2,3-pentafluoropropene.

An azeotropic or quasi-azeotropic composition that is preferred according to the invention comprises from 1% to 80% by weight of hydrogen fluoride and from 99% to 20% by weight of the sum of HCFO-1233xf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HCFO-1233xf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 1% to 80% by weight of hydrogen fluoride and from 99% to 20% by weight of the sum of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HCFO-1233xf, of HCFO-1233zdE and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HCFO-1233xf, of HCFO-1233zdE and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HCFO-1233xf, of HFO-1243zf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HCFO-1233xf, of HFO-1243zf and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HCFO-1233xf, of HCFO-1233zdE and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HCFO-1233xf, of HCFO-1233zdE and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HCFO-1233xf, of HFC-245cb and of HCFC-244bb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HCFO-1233xf, of HFC-245cb and of HCFC-244bb, the boiling point of this preferred composition is between 0 and 40° C. at a pressure of between 0.7 and 8.6 bar absolute.

An azeotropic or quasi-azeotropic composition that is preferred according to the invention comprises from 1% to 85% by weight of hydrogen fluoride and from 99% to 15% by weight of the sum of HCFO-1233xf, of HFC-245cb, of HFO-1243zf and of HFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HCFO-1233xf, of HFC-245cb, of HCFO-1233zdE and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HCFO-1233xf, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 80% by weight of hydrogen fluoride and from 95% to 20% by weight of the sum of HCFO-1233xf, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

Examples 2, 5, 8, 11, 14, 17 and 20 represent the boiling points and pressure ranges of the mixtures and Examples 3, 6, 9, 12, 15, 18 and 21 represent the decantation ranges of the mixtures of Examples 1, 4, 7, 10, 13, 16 and 19 as a function of the mass percentage of HF characterized for isotherms at 0° C., 25° C. and 40° C. The decantation ranges of Examples 3, 6, 9, 12, 15, 18 and 21 are calculated for mixtures of organic compounds having equal-mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at the liquid-vapor equilibrium, under azeotropic conditions.

Example 1: Ternary Mixtures, Isotherm at 25° C.

| HF-HCFO-1233xf-HFO-1234zeE ||||||
|---|---|---|---|---|---|
| Organics 0.95 F1234zeE + 0.05 F1233xf || Organics 0.5 F1234zeE + 0.5 F1233xf || Organics 0.05 F1234zeE + 0.95 F1233xf ||
| MASSFRAC HF | TOTAL PRESSURE bar | MASSFRAC HF | TOTAL PRESSURE bar | MASSFRAC HF | TOTAL PRESSURE bar |
| 0 | 4.7 | 0 | 3.3 | 0 | 1.7 |
| 0.05 | 5.7 | 0.05 | 4.3 | 0.05 | 2.8 |
| 0.1 | 5.7 | 0.1 | 4.3 | 0.1 | 2.8 |
| 0.15 | 5.7 | 0.15 | 4.3 | 0.15 | 2.8 |
| 0.2 | 5.7 | 0.2 | 4.3 | 0.2 | 2.8 |
| 0.25 | 5.7 | 0.25 | 4.3 | 0.25 | 2.8 |
| 0.3 | 5.7 | 0.3 | 4.3 | 0.3 | 2.8 |
| 0.35 | 5.7 | 0.35 | 4.3 | 0.35 | 2.8 |
| 0.4 | 5.7 | 0.4 | 4.3 | 0.4 | 2.8 |
| 0.45 | 5.7 | 0.45 | 4.3 | 0.45 | 2.8 |
| 0.5 | 5.6 | 0.5 | 4.3 | 0.5 | 2.8 |
| 0.55 | 5.6 | 0.55 | 4.2 | 0.55 | 2.8 |
| 0.6 | 5.5 | 0.6 | 4.2 | 0.6 | 2.8 |
| 0.65 | 5.4 | 0.65 | 4.2 | 0.65 | 2.8 |
| 0.7 | 5.2 | 0.7 | 4.1 | 0.7 | 2.8 |
| 0.75 | 5.0 | 0.75 | 3.9 | 0.75 | 2.8 |
| 0.8 | 4.7 | 0.8 | 3.7 | 0.8 | 2.6 |
| 0.85 | 4.2 | 0.85 | 3.3 | 0.85 | 2.4 |
| 0.9 | 3.5 | 0.9 | 2.8 | 0.9 | 2.2 |
| 0.95 | 2.5 | 0.95 | 2.1 | 0.95 | 1.7 |
| 1 | 1.2 | 1 | 1.2 | 1 | 1.2 |

| HF-HCFO-1233xf-HFO-1234zeZ ||||||
|---|---|---|---|---|---|
| Organics 0.95 F1234zeZ + 0.05 F1233xf || Organics 0.5 F1234zeZ + 0.5 F1233xf || Organics 0.05 F1234zeZ + 0.95 F1233xf ||
| MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.7 | 0 | 1.6 |
| 0.05 | 2.9 | 0.05 | 2.8 | 0.05 | 2.7 |
| 0.1 | 2.9 | 0.1 | 2.8 | 0.1 | 2.7 |
| 0.15 | 2.9 | 0.15 | 2.8 | 0.15 | 2.7 |
| 0.2 | 2.9 | 0.2 | 2.8 | 0.2 | 2.7 |
| 0.25 | 2.9 | 0.25 | 2.8 | 0.25 | 2.7 |
| 0.3 | 2.9 | 0.3 | 2.8 | 0.3 | 2.7 |
| 0.35 | 2.9 | 0.35 | 2.8 | 0.35 | 2.7 |
| 0.4 | 2.9 | 0.4 | 2.8 | 0.4 | 2.7 |
| 0.45 | 2.9 | 0.45 | 2.8 | 0.45 | 2.7 |
| 0.5 | 2.9 | 0.5 | 2.8 | 0.5 | 2.7 |
| 0.55 | 2.9 | 0.55 | 2.8 | 0.55 | 2.7 |
| 0.6 | 2.9 | 0.6 | 2.8 | 0.6 | 2.7 |
| 0.65 | 2.9 | 0.65 | 2.8 | 0.65 | 2.7 |
| 0.7 | 2.9 | 0.7 | 2.8 | 0.7 | 2.7 |
| 0.75 | 2.9 | 0.75 | 2.8 | 0.75 | 2.7 |
| 0.8 | 2.8 | 0.8 | 2.7 | 0.8 | 2.5 |
| 0.85 | 2.6 | 0.85 | 2.5 | 0.85 | 2.4 |
| 0.9 | 2.3 | 0.9 | 2.2 | 0.9 | 2.1 |
| 0.95 | 1.8 | 0.95 | 1.8 | 0.95 | 1.7 |
| 1 | 1.2 | 1 | 1.2 | 1 | 1.2 |

| HF-HCFO-1233xf-HCFO-1233zdE ||||||
|---|---|---|---|---|---|
| Organics 0.95 F1233zdE + 0.05 F1233xf || Organics 0.5 F1233zdE + 0.5 F1233xf || Organics 0.05 F1233zdE + 0.95 F1233xf ||
| MASSFRAC HF | TOTAL PRESSURE bar | MASSFRAC HF | TOTAL PRESSURE bar | MASSFRAC HF | TOTAL PRESSURE bar |
| 0 | 1.3 | 0 | 1.4 | 0 | 1.5 |
| 0.05 | 2.4 | 0.05 | 2.5 | 0.05 | 2.6 |
| 0.1 | 2.4 | 0.1 | 2.5 | 0.1 | 2.6 |
| 0.15 | 2.4 | 0.15 | 2.5 | 0.15 | 2.6 |

| MASSFRAC | | MASSFRAC | | MASSFRAC | |
|---|---|---|---|---|---|
| 0.2 | 2.4 | 0.2 | 2.5 | 0.2 | 2.6 |
| 0.25 | 2.4 | 0.25 | 2.5 | 0.25 | 2.6 |
| 0.3 | 2.4 | 0.3 | 2.5 | 0.3 | 2.6 |
| 0.35 | 2.4 | 0.35 | 2.5 | 0.35 | 2.6 |
| 0.4 | 2.4 | 0.4 | 2.5 | 0.4 | 2.6 |
| 0.45 | 2.4 | 0.45 | 2.5 | 0.45 | 2.6 |
| 0.5 | 2.4 | 0.5 | 2.5 | 0.5 | 2.6 |
| 0.55 | 2.4 | 0.55 | 2.5 | 0.55 | 2.6 |
| 0.6 | 2.4 | 0.6 | 2.5 | 0.6 | 2.6 |
| 0.65 | 2.4 | 0.65 | 2.5 | 0.65 | 2.6 |
| 0.7 | 2.4 | 0.7 | 2.5 | 0.7 | 2.6 |
| 0.75 | 2.4 | 0.75 | 2.5 | 0.75 | 2.6 |
| 0.8 | 2.3 | 0.8 | 2.4 | 0.8 | 2.5 |
| 0.85 | 2.2 | 0.85 | 2.3 | 0.85 | 2.3 |
| 0.9 | 1.9 | 0.9 | 2.0 | 0.9 | 2.1 |
| 0.95 | 1.6 | 0.95 | 1.7 | 0.95 | 1.7 |
| 1 | 1.2 | 1 | 1.2 | 1 | 1.2 |

HF-HCFO-1233xf-HFO-1243zf

| Organics 0.95 F1243zf + 0.05 F1233xf | | Organics 0.5 F1243zf + 0.5 F1233xf | | Organics 0.05 F1243zf + 0.95 F1233xf | |
|---|---|---|---|---|---|
| MASSFRAC HF | TOTAL PRES bar | MASSFRAC HF | TOTAL PRES bar | MASSFRAC HF | TOTAL PRES bar |
| 0 | 5.7 | 0 | 4.0 | 0 | 1.8 |
| 0.05 | 6.6 | 0.05 | 5.0 | 0.05 | 2.9 |
| 0.1 | 6.7 | 0.1 | 5.0 | 0.1 | 2.9 |
| 0.15 | 6.6 | 0.15 | 5.0 | 0.15 | 2.9 |
| 0.2 | 6.6 | 0.2 | 5.0 | 0.2 | 2.9 |
| 0.25 | 6.6 | 0.25 | 5.0 | 0.25 | 2.9 |
| 0.3 | 6.6 | 0.3 | 5.0 | 0.3 | 2.9 |
| 0.35 | 6.6 | 0.35 | 5.0 | 0.35 | 2.9 |
| 0.4 | 6.6 | 0.4 | 5.0 | 0.4 | 2.9 |
| 0.45 | 6.6 | 0.45 | 5.0 | 0.45 | 2.9 |
| 0.5 | 6.6 | 0.5 | 5.0 | 0.5 | 2.9 |
| 0.55 | 6.6 | 0.55 | 5.0 | 0.55 | 2.9 |
| 0.6 | 6.6 | 0.6 | 5.0 | 0.6 | 2.9 |
| 0.65 | 6.5 | 0.65 | 4.9 | 0.65 | 2.9 |
| 0.7 | 6.4 | 0.7 | 4.9 | 0.7 | 2.9 |
| 0.75 | 6.3 | 0.75 | 4.7 | 0.75 | 2.9 |
| 0.8 | 6.0 | 0.8 | 4.5 | 0.8 | 2.7 |
| 0.85 | 5.5 | 0.85 | 4.1 | 0.85 | 2.5 |
| 0.9 | 4.7 | 0.9 | 3.5 | 0.9 | 2.2 |
| 0.95 | 3.3 | 0.95 | 2.6 | 0.95 | 1.8 |
| 1 | 1.2 | 1 | 1.2 | 1 | 1.2 |

HF-HFO-1234yf-HCFO-1233xf

| Organics 0.95 F1233xf + 0.05 F1234yf | | Organics 0.5 F1233xf + 0.5 F1234yf | | Organics 0.05 F1233xf + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.3 | 0 | 6.6 |
| 0.05 | 3.0 | 0.05 | 5.4 | 0.05 | 7.5 |
| 0.1 | 3.0 | 0.1 | 5.4 | 0.1 | 7.5 |
| 0.15 | 3.0 | 0.15 | 5.4 | 0.15 | 7.5 |
| 0.2 | 3.0 | 0.2 | 5.4 | 0.2 | 7.5 |
| 0.25 | 3.0 | 0.25 | 5.4 | 0.25 | 7.5 |
| 0.3 | 3.0 | 0.3 | 5.4 | 0.3 | 7.5 |
| 0.35 | 3.0 | 0.35 | 5.4 | 0.35 | 7.5 |
| 0.4 | 3.0 | 0.4 | 5.4 | 0.4 | 7.5 |
| 0.45 | 3.0 | 0.45 | 5.4 | 0.45 | 7.5 |
| 0.5 | 3.0 | 0.5 | 5.4 | 0.5 | 7.5 |
| 0.55 | 3.0 | 0.55 | 5.4 | 0.55 | 7.5 |
| 0.6 | 3.0 | 0.6 | 5.4 | 0.6 | 7.5 |
| 0.65 | 2.9 | 0.65 | 5.4 | 0.65 | 7.5 |
| 0.7 | 2.9 | 0.7 | 5.4 | 0.7 | 7.5 |
| 0.75 | 2.9 | 0.75 | 5.3 | 0.75 | 7.4 |
| 0.8 | 2.8 | 0.8 | 5.0 | 0.8 | 7.0 |
| 0.85 | 2.6 | 0.85 | 4.6 | 0.85 | 6.5 |
| 0.9 | 2.3 | 0.9 | 3.9 | 0.9 | 5.4 |

| | | | | | |
|---|---|---|---|---|---|
| 0.95 | 1.8 | 0.95 | 2.8 | 0.95 | 3.8 |
| 1 | 1.2 | 1 | 1.2 | 1 | 1.2 |

Example 2: Temperature and Pressure Range of Ternary Mixtures

| | Boiling point range | |
|---|---|---|
| Ternary | Temperature °C. | Pressure bar abs |
| HF-HFO-1234yf-HCFO-1233xf | 0 to 40 | −1.1 to −11.4 |
| HF-HCFO-1233xf-HFO-1234zeE | 0 to 40 | −1.1 to −8.8 |
| HF-HCFO-1233xf-HFO-1234zeZ | 0 to 40 | −1.0 to −4.8 |
| HF-HCFO-1233xf-HCFO-1233zdE | 0 to 40 | −0.9 to −4.0 |
| HF-HCFO-1233xf-HFO-1243zf | 0 to 40 | −1.1 to −10.2 |

Example 3: Decantation Range of Ternary Mixtures

| | Decantation ranges Mass percentage of HF | | |
|---|---|---|---|
| Ternary | Isotherm 0° C. | Isotherm 25° C. | Isotherm 40° C. |
| HF-HFO-1234yf-HCFO-1233xf | 5-75 | 5-75 | 15-50 |
| HF-HCFO-1233xf-HFO-1234zeE | 5-70 | 5-60 | 10-45 |
| HF-HCFO-1233xf-HFO-1234zeZ | 5-80 | 5-70 | 5-65 |
| HF-HCFO-1233xf-HCFO-1233zdE | 5-80 | 5-75 | 5-65 |
| HF-HCFO-1233xf-HFO-1243zf | 5-75 | 10-65 | 20-40 |

Example 4: Quaternary Mixtures, Isotherm at 25° C.

| HF - HCFO-1233xf - HCFO-1233zdE - HFC-245cb | | | | | | | |
|---|---|---|---|---|---|---|---|
| Organics 0.9 F1233xf + 0.05 F1233zdE + 0.05 F245cb | | Organics 0.4 F1233xf + 0.3 F1233zdE + 0.3 F245cb | | Organics 0.05 F1233xf + 0.9 F1233zdE + 0.05 F245cb | | Organics 0.05 F1233xf + 0.05 F1233zdE + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.4 | 0 | 1.5 | 0 | 4.3 |
| 0.05 | 2.8 | 0.05 | 3.6 | 0.05 | 2.6 | 0.05 | 5.5 |
| 0.1 | 2.8 | 0.1 | 3.6 | 0.1 | 2.6 | 0.1 | 5.5 |
| 0.15 | 2.8 | 0.15 | 3.6 | 0.15 | 2.6 | 0.15 | 5.5 |
| 0.2 | 2.8 | 0.2 | 3.6 | 0.2 | 2.6 | 0.2 | 5.5 |
| 0.25 | 2.8 | 0.25 | 3.6 | 0.25 | 2.6 | 0.25 | 5.5 |
| 0.3 | 2.8 | 0.3 | 3.6 | 0.3 | 2.6 | 0.3 | 5.5 |
| 0.35 | 2.8 | 0.35 | 3.6 | 0.35 | 2.6 | 0.35 | 5.5 |
| 0.4 | 2.8 | 0.4 | 3.6 | 0.4 | 2.6 | 0.4 | 5.5 |
| 0.45 | 2.8 | 0.45 | 3.6 | 0.45 | 2.6 | 0.45 | 5.5 |
| 0.5 | 2.8 | 0.5 | 3.6 | 0.5 | 2.6 | 0.5 | 5.5 |
| 0.55 | 2.8 | 0.55 | 3.6 | 0.55 | 2.6 | 0.55 | 5.5 |
| 0.6 | 2.8 | 0.6 | 3.7 | 0.6 | 2.6 | 0.6 | 5.5 |
| 0.65 | 2.8 | 0.65 | 3.7 | 0.65 | 2.6 | 0.65 | 5.5 |
| 0.7 | 2.8 | 0.7 | 3.7 | 0.7 | 2.6 | 0.7 | 5.6 |
| 0.75 | 2.8 | 0.75 | 3.7 | 0.75 | 2.6 | 0.75 | 5.6 |
| 0.8 | 2.7 | 0.8 | 3.7 | 0.8 | 2.5 | 0.8 | 5.6 |
| 0.85 | 2.5 | 0.85 | 3.4 | 0.85 | 2.4 | 0.85 | 5.5 |
| 0.9 | 2.2 | 0.9 | 2.9 | 0.9 | 2.1 | 0.9 | 4.8 |
| 0.95 | 1.8 | 0.95 | 2.2 | 0.95 | 1.7 | 0.95 | 3.4 |
| 1 | 1.2 | 1 | 1.2 | 1 | 1.2 | 1 | 1.2 |

| HF - HCFO-1233xf- HFO-1234zeE - HFC-245cb | | | | | | | |
|---|---|---|---|---|---|---|---|
| Organics 0.9 F1233xf + 0.05 F1234zeE + 0.05 F245cb | | Organics 0.4 F1233xf + 0.3 F1234zeE + 0.3 F245cb | | Organics 0.05 F1233xf + 0.9 F1234zeE + 0.05 F245cb | | Organics 0.05 F1233xf + 0.05 F1234zeE + 0.9 F245cb | |
| MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 3.2 | 0 | 3.5 | 0 | 4.7 | 0 | 4.5 |
| 0.05 | 4.3 | 0.05 | 4.6 | 0.05 | 5.7 | 0.05 | 5.7 |
| 0.1 | 4.3 | 0.1 | 4.6 | 0.1 | 5.7 | 0.1 | 5.7 |
| 0.15 | 4.3 | 0.15 | 4.6 | 0.15 | 5.7 | 0.15 | 5.7 |
| 0.2 | 4.3 | 0.2 | 4.6 | 0.2 | 5.7 | 0.2 | 5.7 |
| 0.25 | 4.3 | 0.25 | 4.6 | 0.25 | 5.7 | 0.25 | 5.7 |
| 0.3 | 4.3 | 0.3 | 4.6 | 0.3 | 5.7 | 0.3 | 5.7 |

-continued

| | | | | | | | |
|---|---|---|---|---|---|---|---|
| 0.35 | 4.3 | 0.35 | 4.6 | 0.35 | 5.7 | 0.35 | 5.7 |
| 0.4 | 4.4 | 0.4 | 4.6 | 0.4 | 5.7 | 0.4 | 5.7 |
| 0.45 | 4.4 | 0.45 | 4.6 | 0.45 | 5.7 | 0.45 | 5.7 |
| 0.5 | 4.4 | 0.5 | 4.6 | 0.5 | 5.7 | 0.5 | 5.7 |
| 0.55 | 4.4 | 0.55 | 4.6 | 0.55 | 5.6 | 0.55 | 5.7 |
| 0.6 | 4.4 | 0.6 | 4.6 | 0.6 | 5.6 | 0.6 | 5.7 |
| 0.65 | 4.4 | 0.65 | 4.7 | 0.65 | 5.5 | 0.65 | 5.7 |
| 0.7 | 4.5 | 0.7 | 4.7 | 0.7 | 5.3 | 0.7 | 5.7 |
| 0.75 | 4.5 | 0.75 | 4.6 | 0.75 | 5.1 | 0.75 | 5.7 |
| 0.8 | 4.5 | 0.8 | 4.4 | 0.8 | 4.8 | 0.8 | 5.7 |
| 0.85 | 4.2 | 0.85 | 4.0 | 0.85 | 4.3 | 0.85 | 5.6 |
| 0.9 | 3.6 | 0.9 | 3.4 | 0.9 | 3.6 | 0.9 | 4.8 |
| 0.95 | 2.6 | 0.95 | 2.5 | 0.95 | 2.6 | 0.95 | 3.4 |
| 1 | 1.2 | 1 | 1.2 | 1 | 1.2 | 1 | 1.2 |

HF - HCFO-1233xf - HFO-1234zeZ - HFC-245cb

| Organics 0.9 F1233xf + 0.05 F1234zeZ + 0.05 F245cb | | Organics 0.4 F1233xf + 0.3 F1234zeZ + 0.3 F245cb | | Organics 0.05 F1233xf + 0.9 F1234zeZ + 0.05 F245cb | | Organics 0.05 F1233xf + 0.05 F1234zeZ + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.6 | 0 | 1.9 | 0 | 4.3 |
| 0.05 | 2.8 | 0.05 | 3.7 | 0.05 | 3.0 | 0.05 | 5.5 |
| 0.1 | 2.8 | 0.1 | 3.7 | 0.1 | 3.0 | 0.1 | 5.5 |
| 0.15 | 2.8 | 0.15 | 3.7 | 0.15 | 3.0 | 0.15 | 5.5 |
| 0.2 | 2.8 | 0.2 | 3.7 | 0.2 | 3.0 | 0.2 | 5.5 |
| 0.25 | 2.8 | 0.25 | 3.7 | 0.25 | 3.0 | 0.25 | 5.5 |
| 0.3 | 2.8 | 0.3 | 3.7 | 0.3 | 3.0 | 0.3 | 5.5 |
| 0.35 | 2.8 | 0.35 | 3.7 | 0.35 | 3.0 | 0.35 | 5.5 |
| 0.4 | 2.8 | 0.4 | 3.7 | 0.4 | 3.0 | 0.4 | 5.5 |
| 0.45 | 2.8 | 0.45 | 3.7 | 0.45 | 3.1 | 0.45 | 5.5 |
| 0.5 | 2.8 | 0.5 | 3.7 | 0.5 | 3.1 | 0.5 | 5.5 |
| 0.55 | 2.9 | 0.55 | 3.7 | 0.55 | 3.1 | 0.55 | 5.5 |
| 0.6 | 2.9 | 0.6 | 3.8 | 0.6 | 3.1 | 0.6 | 5.5 |
| 0.65 | 2.9 | 0.65 | 3.8 | 0.65 | 3.1 | 0.65 | 5.6 |
| 0.7 | 2.9 | 0.7 | 3.8 | 0.7 | 3.1 | 0.7 | 5.6 |
| 0.75 | 2.9 | 0.75 | 3.8 | 0.75 | 3.1 | 0.75 | 5.6 |
| 0.8 | 2.7 | 0.8 | 3.8 | 0.8 | 2.9 | 0.8 | 5.6 |
| 0.85 | 2.5 | 0.85 | 3.5 | 0.85 | 2.7 | 0.85 | 5.5 |
| 0.9 | 2.2 | 0.9 | 3.0 | 0.9 | 2.4 | 0.9 | 4.8 |
| 0.95 | 1.8 | 0.95 | 2.3 | 0.95 | 1.9 | 0.95 | 3.4 |
| 1 | 1.2 | 1 | 1.2 | 1 | 1.2 | 1 | 1.2 |

HF - HCFO-1233xf - HFO-1243zf - HFC-245cb

| Organics 0.9 F1233xf + 0.05 F1243zf + 0.05 F245cb | | Organics 0.4 F1233xf + 0.3 F1243zf + 0.3 F245cb | | Organics 0.05 F1233xf + 0.9 F1243zf + 0.05 F245cb | | Organics 0.05 F1233xf + 0.05 F1243zf + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.0 | 0 | 5.6 | 0 | 4.6 |
| 0.05 | 3.1 | 0.05 | 5.1 | 0.05 | 6.6 | 0.05 | 5.7 |
| 0.1 | 3.1 | 0.1 | 5.1 | 0.1 | 6.6 | 0.1 | 5.7 |
| 0.15 | 3.1 | 0.15 | 5.1 | 0.15 | 6.6 | 0.15 | 5.7 |
| 0.2 | 3.1 | 0.2 | 5.1 | 0.2 | 6.6 | 0.2 | 5.7 |
| 0.25 | 3.1 | 0.25 | 5.1 | 0.25 | 6.6 | 0.25 | 5.7 |
| 0.3 | 3.1 | 0.3 | 5.1 | 0.3 | 6.6 | 0.3 | 5.7 |
| 0.35 | 3.1 | 0.35 | 5.1 | 0.35 | 6.6 | 0.35 | 5.7 |
| 0.4 | 3.1 | 0.4 | 5.1 | 0.4 | 6.6 | 0.4 | 5.8 |
| 0.45 | 3.1 | 0.45 | 5.1 | 0.45 | 6.6 | 0.45 | 5.8 |
| 0.5 | 3.1 | 0.5 | 5.1 | 0.5 | 6.6 | 0.5 | 5.8 |
| 0.55 | 3.1 | 0.55 | 5.1 | 0.55 | 6.6 | 0.55 | 5.8 |
| 0.6 | 3.1 | 0.6 | 5.1 | 0.6 | 6.5 | 0.6 | 5.8 |
| 0.65 | 3.1 | 0.65 | 5.1 | 0.65 | 6.5 | 0.65 | 5.8 |
| 0.7 | 3.1 | 0.7 | 5.1 | 0.7 | 6.4 | 0.7 | 5.8 |
| 0.75 | 3.1 | 0.75 | 5.1 | 0.75 | 6.3 | 0.75 | 5.8 |
| 0.8 | 2.9 | 0.8 | 4.8 | 0.8 | 6.0 | 0.8 | 5.8 |
| 0.85 | 2.7 | 0.85 | 4.5 | 0.85 | 5.5 | 0.85 | 5.7 |
| 0.9 | 2.4 | 0.9 | 3.8 | 0.9 | 4.7 | 0.9 | 4.9 |
| 0.95 | 1.9 | 0.95 | 2.8 | 0.95 | 3.3 | 0.95 | 3.5 |
| 1 | 1.2 | 1 | 1.2 | 1 | 1.2 | 1 | 1.2 |

-continued

HF - HCFO-1233xf - HCFO-1233zdE - HFO-1234zeE

| Organics 0.9 F1233xf + 0.05 F1233zdE + 0.05 F1234zeE | | Organics 0.05 F1233xf + 0.9 F1233zdE + 0.05 F1234zeE | | Organics 0.05 F1233xf + 0.05 F1233zdE + 0.9 F1234zeE | | Organics 0.4 F1233xf + 0.3 F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.6 | 0 | 2.5 |
| 0.05 | 2.8 | 0.05 | 2.6 | 0.05 | 5.5 | 0.05 | 3.6 |
| 0.1 | 2.8 | 0.1 | 2.6 | 0.1 | 5.5 | 0.1 | 3.6 |
| 0.15 | 2.8 | 0.15 | 2.6 | 0.15 | 5.5 | 0.15 | 3.6 |
| 0.2 | 2.8 | 0.2 | 2.6 | 0.2 | 5.5 | 0.2 | 3.6 |
| 0.25 | 2.8 | 0.25 | 2.6 | 0.25 | 5.5 | 0.25 | 3.6 |
| 0.3 | 2.8 | 0.3 | 2.6 | 0.3 | 5.5 | 0.3 | 3.6 |
| 0.35 | 2.8 | 0.35 | 2.6 | 0.35 | 5.5 | 0.35 | 3.6 |
| 0.4 | 2.8 | 0.4 | 2.6 | 0.4 | 5.5 | 0.4 | 3.6 |
| 0.45 | 2.8 | 0.45 | 2.6 | 0.45 | 5.5 | 0.45 | 3.6 |
| 0.5 | 2.8 | 0.5 | 2.6 | 0.5 | 5.5 | 0.5 | 3.6 |
| 0.55 | 2.8 | 0.55 | 2.6 | 0.55 | 5.4 | 0.55 | 3.5 |
| 0.6 | 2.8 | 0.6 | 2.6 | 0.6 | 5.4 | 0.6 | 3.5 |
| 0.65 | 2.8 | 0.65 | 2.6 | 0.65 | 5.3 | 0.65 | 3.5 |
| 0.7 | 2.8 | 0.7 | 2.6 | 0.7 | 5.1 | 0.7 | 3.5 |
| 0.75 | 2.8 | 0.75 | 2.6 | 0.75 | 4.9 | 0.75 | 3.3 |
| 0.8 | 2.6 | 0.8 | 2.5 | 0.8 | 4.6 | 0.8 | 3.2 |
| 0.85 | 2.4 | 0.85 | 2.3 | 0.85 | 4.1 | 0.85 | 2.9 |
| 0.9 | 2.2 | 0.9 | 2.0 | 0.9 | 3.4 | 0.9 | 2.5 |
| 0.95 | 1.7 | 0.95 | 1.7 | 0.95 | 2.5 | 0.95 | 1.9 |
| 1 | 1.2 | 1 | 1.2 | 1 | 1.2 | 1 | 1.2 |

HF - HCFO-1233xf - HCFO-1233zdE - HFO-1234zeZ

| Organics 0.9 F1233xf + 0.05 F1233zdE + 0.05 F1234zeZ | | Organics 0.05 F1233xf + 0.9 F1233zdE + 0.05 F1234zeZ | | Organics 0.05 F1233xf + 0.05 F1233zdE + 0.9 F1234zeZ | | Organics 0.4 F1233xf + 0.3 F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.4 | 0 | 1.8 | 0 | 1.6 |
| 0.05 | 2.7 | 0.05 | 2.5 | 0.05 | 2.9 | 0.05 | 2.7 |
| 0.1 | 2.7 | 0.1 | 2.5 | 0.1 | 2.9 | 0.1 | 2.7 |
| 0.15 | 2.7 | 0.15 | 2.5 | 0.15 | 2.9 | 0.15 | 2.7 |
| 0.2 | 2.7 | 0.2 | 2.5 | 0.2 | 2.9 | 0.2 | 2.7 |
| 0.25 | 2.7 | 0.25 | 2.5 | 0.25 | 2.9 | 0.25 | 2.7 |
| 0.3 | 2.7 | 0.3 | 2.5 | 0.3 | 2.9 | 0.3 | 2.7 |
| 0.35 | 2.7 | 0.35 | 2.5 | 0.35 | 2.9 | 0.35 | 2.7 |
| 0.4 | 2.7 | 0.4 | 2.5 | 0.4 | 2.9 | 0.4 | 2.7 |
| 0.45 | 2.7 | 0.45 | 2.5 | 0.45 | 2.9 | 0.45 | 2.7 |
| 0.5 | 2.7 | 0.5 | 2.5 | 0.5 | 2.9 | 0.5 | 2.7 |
| 0.55 | 2.7 | 0.55 | 2.5 | 0.55 | 2.9 | 0.55 | 2.7 |
| 0.6 | 2.7 | 0.6 | 2.5 | 0.6 | 2.9 | 0.6 | 2.7 |
| 0.65 | 2.7 | 0.65 | 2.5 | 0.65 | 2.9 | 0.65 | 2.7 |
| 0.7 | 2.7 | 0.7 | 2.5 | 0.7 | 2.9 | 0.7 | 2.7 |
| 0.75 | 2.7 | 0.75 | 2.5 | 0.75 | 2.9 | 0.75 | 2.7 |
| 0.8 | 2.5 | 0.8 | 2.4 | 0.8 | 2.8 | 0.8 | 2.6 |
| 0.85 | 2.4 | 0.85 | 2.2 | 0.85 | 2.6 | 0.85 | 2.4 |
| 0.9 | 2.1 | 0.9 | 2.0 | 0.9 | 2.3 | 0.9 | 2.1 |
| 0.95 | 1.7 | 0.95 | 1.6 | 0.95 | 1.8 | 0.95 | 1.7 |
| 1 | 1.2 | 1 | 1.2 | 1 | 1.2 | 1 | 1.2 |

HF - HCFO-1233xf - HCFO-1233zdE - HFO-1243zf

| Organics 0.9 F1233xf + 0.05 F1233zdE + 0.05 F1243zf | | Organics 0.05 F1233xf + 0.9 F1233zdE + 0.05 F1243zf | | Organics 0.05 F1233xf + 0.05 F1233zdE + 0.9 F1243zf | | Organics 0.4 F1233xf + 0.3 F1233zdE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 5.5 | 0 | 3.0 |
| 0.05 | 2.9 | 0.05 | 2.7 | 0.05 | 6.4 | 0.05 | 4.1 |
| 0.1 | 2.9 | 0.1 | 2.7 | 0.1 | 6.5 | 0.1 | 4.1 |
| 0.15 | 2.9 | 0.15 | 2.7 | 0.15 | 6.5 | 0.15 | 4.1 |
| 0.2 | 2.9 | 0.2 | 2.7 | 0.2 | 6.5 | 0.2 | 4.1 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0.25 | 2.9 | 0.25 | 2.7 | 0.25 | 6.5 | 0.25 | 4.1 |
| 0.3 | 2.9 | 0.3 | 2.7 | 0.3 | 6.5 | 0.3 | 4.1 |
| 0.35 | 2.9 | 0.35 | 2.7 | 0.35 | 6.5 | 0.35 | 4.1 |
| 0.4 | 2.9 | 0.4 | 2.7 | 0.4 | 6.5 | 0.4 | 4.1 |
| 0.45 | 2.9 | 0.45 | 2.7 | 0.45 | 6.5 | 0.45 | 4.1 |
| 0.5 | 2.9 | 0.5 | 2.7 | 0.5 | 6.4 | 0.5 | 4.1 |
| 0.55 | 2.9 | 0.55 | 2.7 | 0.55 | 6.4 | 0.55 | 4.1 |
| 0.6 | 2.9 | 0.6 | 2.7 | 0.6 | 6.4 | 0.6 | 4.0 |
| 0.65 | 2.9 | 0.65 | 2.7 | 0.65 | 6.4 | 0.65 | 4.0 |
| 0.7 | 2.9 | 0.7 | 2.7 | 0.7 | 6.3 | 0.7 | 4.0 |
| 0.75 | 2.9 | 0.75 | 2.7 | 0.75 | 6.1 | 0.75 | 3.9 |
| 0.8 | 2.7 | 0.8 | 2.6 | 0.8 | 5.8 | 0.8 | 3.7 |
| 0.85 | 2.5 | 0.85 | 2.4 | 0.85 | 5.3 | 0.85 | 3.4 |
| 0.9 | 2.2 | 0.9 | 2.1 | 0.9 | 4.5 | 0.9 | 2.9 |
| 0.95 | 1.8 | 0.95 | 1.7 | 0.95 | 3.2 | 0.95 | 2.2 |
| 1 | 1.2 | 1 | 1.2 | 1 | 1.2 | 1 | 1.2 |

HF - HCFO-1233xf - HFO-1234zeE - HFO-1234zeZ

| Organics 0.9 F1233xf + 0.05 F1234zeE + 0.05 F1234zeZ | | Organics 0.05 F1233xf + 0.9 F1234zeE + 0.05 F1234zeZ | | Organics 0.05 F1233xf + 0.05 F1234zeE + 0.9 F1234zeZ | | Organics 0.4 F1233xf + 0.3 F1234zeE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.9 | 0 | 2.7 |
| 0.05 | 2.8 | 0.05 | 5.5 | 0.05 | 3.1 | 0.05 | 3.7 |
| 0.1 | 2.8 | 0.1 | 5.5 | 0.1 | 3.0 | 0.1 | 3.7 |
| 0.15 | 2.8 | 0.15 | 5.5 | 0.15 | 3.0 | 0.15 | 3.7 |
| 0.2 | 2.8 | 0.2 | 5.5 | 0.2 | 3.0 | 0.2 | 3.7 |
| 0.25 | 2.8 | 0.25 | 5.5 | 0.25 | 3.0 | 0.25 | 3.7 |
| 0.3 | 2.8 | 0.3 | 5.5 | 0.3 | 3.0 | 0.3 | 3.7 |
| 0.35 | 2.8 | 0.35 | 5.5 | 0.35 | 3.0 | 0.35 | 3.7 |
| 0.4 | 2.8 | 0.4 | 5.5 | 0.4 | 3.0 | 0.4 | 3.7 |
| 0.45 | 2.8 | 0.45 | 5.5 | 0.45 | 3.0 | 0.45 | 3.7 |
| 0.5 | 2.8 | 0.5 | 5.5 | 0.5 | 3.0 | 0.5 | 3.7 |
| 0.55 | 2.8 | 0.55 | 5.4 | 0.55 | 3.0 | 0.55 | 3.7 |
| 0.6 | 2.8 | 0.6 | 5.4 | 0.6 | 3.0 | 0.6 | 3.6 |
| 0.65 | 2.8 | 0.65 | 5.3 | 0.65 | 3.0 | 0.65 | 3.6 |
| 0.7 | 2.8 | 0.7 | 5.1 | 0.7 | 3.0 | 0.7 | 3.6 |
| 0.75 | 2.8 | 0.75 | 4.9 | 0.75 | 3.0 | 0.75 | 3.5 |
| 0.8 | 2.7 | 0.8 | 4.6 | 0.8 | 2.9 | 0.8 | 3.3 |
| 0.85 | 2.5 | 0.85 | 4.1 | 0.85 | 2.7 | 0.85 | 3.0 |
| 0.9 | 2.2 | 0.9 | 3.4 | 0.9 | 2.3 | 0.9 | 2.6 |
| 0.95 | 1.8 | 0.95 | 2.5 | 0.95 | 1.9 | 0.95 | 2.0 |
| 1 | 1.2 | 1 | 1.2 | 1 | 1.2 | 1 | 1.2 |

HF - HCFO-1233xf - HFO-1234zeE - HFO-1243zf

| Organics 0.9 F1233xf + 0.05 F1234zeE + 0.05 F1243zf | | Organics 0.05 F1233xf + 0.9 F1234zeE + 0.05 F1243zf | | Organics 0.05 F1233xf + 0.05 F1234zeE + 0.9 F1243zf | | Organics 0.4 F1233xf + 0.3 F1234zeE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 5.6 | 0 | 4.0 |
| 0.05 | 3.1 | 0.05 | 5.7 | 0.05 | 6.6 | 0.05 | 5.1 |
| 0.1 | 3.1 | 0.1 | 5.8 | 0.1 | 6.6 | 0.1 | 5.1 |
| 0.15 | 3.1 | 0.15 | 5.8 | 0.15 | 6.6 | 0.15 | 5.1 |
| 0.2 | 3.1 | 0.2 | 5.8 | 0.2 | 6.6 | 0.2 | 5.1 |
| 0.25 | 3.1 | 0.25 | 5.8 | 0.25 | 6.6 | 0.25 | 5.1 |
| 0.3 | 3.1 | 0.3 | 5.8 | 0.3 | 6.6 | 0.3 | 5.0 |
| 0.35 | 3.1 | 0.35 | 5.7 | 0.35 | 6.6 | 0.35 | 5.0 |
| 0.4 | 3.1 | 0.4 | 5.7 | 0.4 | 6.6 | 0.4 | 5.0 |
| 0.45 | 3.1 | 0.45 | 5.7 | 0.45 | 6.6 | 0.45 | 5.0 |
| 0.5 | 3.1 | 0.5 | 5.7 | 0.5 | 6.6 | 0.5 | 5.0 |
| 0.55 | 3.1 | 0.55 | 5.7 | 0.55 | 6.6 | 0.55 | 5.0 |
| 0.6 | 3.1 | 0.6 | 5.6 | 0.6 | 6.5 | 0.6 | 5.0 |
| 0.65 | 3.1 | 0.65 | 5.5 | 0.65 | 6.5 | 0.65 | 4.9 |
| 0.7 | 3.0 | 0.7 | 5.3 | 0.7 | 6.4 | 0.7 | 4.8 |
| 0.75 | 3.0 | 0.75 | 5.1 | 0.75 | 6.2 | 0.75 | 4.7 |
| 0.8 | 2.9 | 0.8 | 4.8 | 0.8 | 5.9 | 0.8 | 4.4 |
| 0.85 | 2.6 | 0.85 | 4.3 | 0.85 | 5.4 | 0.85 | 4.0 |
| 0.9 | 2.3 | 0.9 | 3.6 | 0.9 | 4.6 | 0.9 | 3.4 |

-continued

| | | | | | | | |
|---|---|---|---|---|---|---|---|
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF - HCFO-1233xf - HFO-1234zeZ - HFO-1243zf

| Organics 0.9 F1233xf + 0.05 F1234zeZ + 0.05 F1243zf | | Organics 0.05 F1233xf + 0.9 F1234zeZ + 0.05 F1243zf | | Organics 0.05 F1233xf + 0.05 F1234zeZ + 0.9 F1243zf | | Organics 0.4 F1233xf + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 5.5 | 0 | 3.1 |
| 0.05 | 2.9 | 0.05 | 3.1 | 0.05 | 6.4 | 0.05 | 4.2 |
| 0.1 | 2.9 | 0.1 | 3.1 | 0.1 | 6.5 | 0.1 | 4.2 |
| 0.15 | 2.9 | 0.15 | 3.1 | 0.15 | 6.5 | 0.15 | 4.2 |
| 0.2 | 2.9 | 0.2 | 3.1 | 0.2 | 6.5 | 0.2 | 4.2 |
| 0.25 | 2.9 | 0.25 | 3.1 | 0.25 | 6.5 | 0.25 | 4.2 |
| 0.3 | 2.9 | 0.3 | 3.1 | 0.3 | 6.5 | 0.3 | 4.2 |
| 0.35 | 2.9 | 0.35 | 3.1 | 0.35 | 6.5 | 0.35 | 4.2 |
| 0.4 | 2.9 | 0.4 | 3.1 | 0.4 | 6.5 | 0.4 | 4.2 |
| 0.45 | 2.9 | 0.45 | 3.1 | 0.45 | 6.5 | 0.45 | 4.2 |
| 0.5 | 2.9 | 0.5 | 3.1 | 0.5 | 6.4 | 0.5 | 4.2 |
| 0.55 | 2.9 | 0.55 | 3.1 | 0.55 | 6.4 | 0.55 | 4.2 |
| 0.6 | 2.9 | 0.6 | 3.1 | 0.6 | 6.4 | 0.6 | 4.1 |
| 0.65 | 2.9 | 0.65 | 3.1 | 0.65 | 6.4 | 0.65 | 4.1 |
| 0.7 | 2.9 | 0.7 | 3.1 | 0.7 | 6.3 | 0.7 | 4.1 |
| 0.75 | 2.9 | 0.75 | 3.1 | 0.75 | 6.1 | 0.75 | 4.0 |
| 0.8 | 2.8 | 0.8 | 3.0 | 0.8 | 5.8 | 0.8 | 3.8 |
| 0.85 | 2.5 | 0.85 | 2.7 | 0.85 | 5.3 | 0.85 | 3.5 |
| 0.9 | 2.2 | 0.9 | 2.4 | 0.9 | 4.5 | 0.9 | 3.0 |
| 0.95 | 1.8 | 0.95 | 1.9 | 0.95 | 3.2 | 0.95 | 2.3 |
| 1 | 1.2 | 1 | 1.2 | 1 | 1.2 | 1 | 1.2 |

HF - HCFO-1233xf - HFO-1234yf - HFC-245cb

| Organics 0.9 F1233xf + 0.05 F1234yf + 0.05 F245cb | | Organics 0.4 F1233xf + 0.3 F1234yf + 0.3 F245cb | | Organics 0.05 F1233xf + 0.9 F1234yf + 0.05 F245cb | | Organics 0.05 F1233xf + 0.05 F1234yf + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.2 | 0 | 6.5 | 0 | 4.6 |
| 0.05 | 3.1 | 0.05 | 5.3 | 0.05 | 7.4 | 0.05 | 5.8 |
| 0.1 | 3.1 | 0.1 | 5.3 | 0.1 | 7.4 | 0.1 | 5.8 |
| 0.15 | 3.1 | 0.15 | 5.3 | 0.15 | 7.4 | 0.15 | 5.8 |
| 0.2 | 3.1 | 0.2 | 5.3 | 0.2 | 7.4 | 0.2 | 5.8 |
| 0.25 | 3.1 | 0.25 | 5.3 | 0.25 | 7.4 | 0.25 | 5.8 |
| 0.3 | 3.1 | 0.3 | 5.3 | 0.3 | 7.4 | 0.3 | 5.8 |
| 0.35 | 3.1 | 0.35 | 5.3 | 0.35 | 7.4 | 0.35 | 5.8 |
| 0.4 | 3.1 | 0.4 | 5.3 | 0.4 | 7.4 | 0.4 | 5.8 |
| 0.45 | 3.1 | 0.45 | 5.3 | 0.45 | 7.4 | 0.45 | 5.8 |
| 0.5 | 3.1 | 0.5 | 5.3 | 0.5 | 7.4 | 0.5 | 5.8 |
| 0.55 | 3.1 | 0.55 | 5.3 | 0.55 | 7.4 | 0.55 | 5.8 |
| 0.6 | 3.1 | 0.6 | 5.3 | 0.6 | 7.4 | 0.6 | 5.8 |
| 0.65 | 3.1 | 0.65 | 5.3 | 0.65 | 7.4 | 0.65 | 5.8 |
| 0.7 | 3.1 | 0.7 | 5.3 | 0.7 | 7.4 | 0.7 | 5.8 |
| 0.75 | 3.1 | 0.75 | 5.4 | 0.75 | 7.3 | 0.75 | 5.8 |
| 0.8 | 3.0 | 0.8 | 5.2 | 0.8 | 7.0 | 0.8 | 5.8 |
| 0.85 | 2.8 | 0.85 | 4.8 | 0.85 | 6.4 | 0.85 | 5.7 |
| 0.9 | 2.4 | 0.9 | 4.1 | 0.9 | 5.4 | 0.9 | 4.9 |
| 0.95 | 1.9 | 0.95 | 2.9 | 0.95 | 3.7 | 0.95 | 3.5 |
| 1 | 1.2 | 1 | 1.2 | 1 | 1.2 | 1 | 1.2 |

HF - HCFO-1233xf - HFO-1234yf - HCFO-1233zdE

| Organics 0.9 F1233xf + 0.05 F1234yf + 0.05 F1233zdE | | Organics 0.05 F1233xf + 0.9 F1234yf + 0.05 F1233zdE | | Organics 0.05 F1233xf + 0.05 F1234yf + 0.9 F1233zdE | | Organics 0.4 F1233xf + 0.3 F1234yf + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.7 | 0 | 3.2 |
| 0.05 | 3.0 | 0.05 | 7.3 | 0.05 | 2.8 | 0.05 | 4.3 |

-continued

| | | | | | | | |
|---|---|---|---|---|---|---|---|
| 0.1 | 3.0 | 0.1 | 7.3 | 0.1 | 2.8 | 0.1 | 4.3 |
| 0.15 | 3.0 | 0.15 | 7.3 | 0.15 | 2.8 | 0.15 | 4.3 |
| 0.2 | 2.9 | 0.2 | 7.3 | 0.2 | 2.8 | 0.2 | 4.3 |
| 0.25 | 2.9 | 0.25 | 7.3 | 0.25 | 2.8 | 0.25 | 4.3 |
| 0.3 | 2.9 | 0.3 | 7.3 | 0.3 | 2.8 | 0.3 | 4.3 |
| 0.35 | 2.9 | 0.35 | 7.3 | 0.35 | 2.8 | 0.35 | 4.3 |
| 0.4 | 2.9 | 0.4 | 7.3 | 0.4 | 2.8 | 0.4 | 4.3 |
| 0.45 | 2.9 | 0.45 | 7.3 | 0.45 | 2.7 | 0.45 | 4.3 |
| 0.5 | 2.9 | 0.5 | 7.3 | 0.5 | 2.7 | 0.5 | 4.3 |
| 0.55 | 2.9 | 0.55 | 7.3 | 0.55 | 2.7 | 0.55 | 4.3 |
| 0.6 | 2.9 | 0.6 | 7.3 | 0.6 | 2.7 | 0.6 | 4.3 |
| 0.65 | 2.9 | 0.65 | 7.3 | 0.65 | 2.7 | 0.65 | 4.3 |
| 0.7 | 2.9 | 0.7 | 7.3 | 0.7 | 2.7 | 0.7 | 4.3 |
| 0.75 | 2.9 | 0.75 | 7.1 | 0.75 | 2.7 | 0.75 | 4.2 |
| 0.8 | 2.8 | 0.8 | 6.8 | 0.8 | 2.6 | 0.8 | 4.0 |
| 0.85 | 2.6 | 0.85 | 6.2 | 0.85 | 2.4 | 0.85 | 3.7 |
| 0.9 | 2.3 | 0.9 | 5.3 | 0.9 | 2.1 | 0.9 | 3.1 |
| 0.95 | 1.8 | 0.95 | 3.7 | 0.95 | 1.7 | 0.95 | 2.3 |
| 1 | 1.2 | 1 | 1.2 | 1 | 1.2 | 1 | 1.2 |

HF - HCFO-1233xf - HFO-1234vf - HFO-1234zeE

| Organics 0.9 F1233xf + 0.05 F1234yf + 0.05 F1234zeE | | Organics 0.05 F1233xf + 0.9 F1234yf + 0.05 F1234zeE | | Organics 0.05 F1233xf + 0.05 F1234yf + 0.9 F1234zeE | | Organics 0.4 F1233xf + 0.3 F1234yf + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.8 | 0 | 4.2 |
| 0.05 | 3.1 | 0.05 | 7.4 | 0.05 | 5.8 | 0.05 | 5.3 |
| 0.1 | 3.1 | 0.1 | 7.4 | 0.1 | 5.8 | 0.1 | 5.3 |
| 0.15 | 3.1 | 0.15 | 7.4 | 0.15 | 5.8 | 0.15 | 5.3 |
| 0.2 | 3.1 | 0.2 | 7.4 | 0.2 | 5.8 | 0.2 | 5.3 |
| 0.25 | 3.1 | 0.25 | 7.4 | 0.25 | 5.8 | 0.25 | 5.3 |
| 0.3 | 3.1 | 0.3 | 7.4 | 0.3 | 5.8 | 0.3 | 5.3 |
| 0.35 | 3.1 | 0.35 | 7.4 | 0.35 | 5.8 | 0.35 | 5.3 |
| 0.4 | 3.1 | 0.4 | 7.4 | 0.4 | 5.8 | 0.4 | 5.3 |
| 0.45 | 3.1 | 0.45 | 7.4 | 0.45 | 5.8 | 0.45 | 5.3 |
| 0.5 | 3.1 | 0.5 | 7.4 | 0.5 | 5.8 | 0.5 | 5.3 |
| 0.55 | 3.1 | 0.55 | 7.4 | 0.55 | 5.7 | 0.55 | 5.3 |
| 0.6 | 3.1 | 0.6 | 7.4 | 0.6 | 5.6 | 0.6 | 5.3 |
| 0.65 | 3.1 | 0.65 | 7.5 | 0.65 | 5.5 | 0.65 | 5.3 |
| 0.7 | 3.1 | 0.7 | 7.4 | 0.7 | 5.4 | 0.7 | 5.2 |
| 0.75 | 3.1 | 0.75 | 7.2 | 0.75 | 5.2 | 0.75 | 5.0 |
| 0.8 | 2.9 | 0.8 | 6.9 | 0.8 | 4.8 | 0.8 | 4.7 |
| 0.85 | 2.7 | 0.85 | 6.3 | 0.85 | 4.3 | 0.85 | 4.3 |
| 0.9 | 2.3 | 0.9 | 5.3 | 0.9 | 3.6 | 0.9 | 3.6 |
| 0.95 | 1.9 | 0.95 | 3.7 | 0.95 | 2.6 | 0.95 | 2.6 |
| 1 | 1.2 | 1 | 1.2 | 1 | 1.2 | 1 | 1.2 |

HF - HCFO-1233xf - HFO-1234yf - HFO-1234zeZ

| Organics 0.9 F1233xf + 0.05 F1234yf + 0.05 F1234zeZ | | Organics 0.05 F1233xf + 0.9 F1234yf + 0.05 F1234zeZ | | Organics 0.05 F1233xf + 0.05 F1234yf + 0.9 F1234zeZ | | Organics 0.4 F1233xf + 0.3 F1234yf + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 6.3 | 0 | 2.1 | 0 | 3.3 |
| 0.05 | 3.0 | 0.05 | 7.3 | 0.05 | 3.2 | 0.05 | 4.4 |
| 0.1 | 3.0 | 0.1 | 7.3 | 0.1 | 3.2 | 0.1 | 4.4 |
| 0.15 | 3.0 | 0.15 | 7.3 | 0.15 | 3.2 | 0.15 | 4.4 |
| 0.2 | 3.0 | 0.2 | 7.3 | 0.2 | 3.2 | 0.2 | 4.4 |
| 0.25 | 3.0 | 0.25 | 7.3 | 0.25 | 3.2 | 0.25 | 4.4 |
| 0.3 | 3.0 | 0.3 | 7.3 | 0.3 | 3.2 | 0.3 | 4.4 |
| 0.35 | 3.0 | 0.35 | 7.3 | 0.35 | 3.2 | 0.35 | 4.4 |
| 0.4 | 3.0 | 0.4 | 7.3 | 0.4 | 3.2 | 0.4 | 4.4 |
| 0.45 | 3.0 | 0.45 | 7.3 | 0.45 | 3.2 | 0.45 | 4.4 |
| 0.5 | 3.0 | 0.5 | 7.3 | 0.5 | 3.2 | 0.5 | 4.4 |
| 0.55 | 3.0 | 0.55 | 7.3 | 0.55 | 3.2 | 0.55 | 4.4 |
| 0.6 | 3.0 | 0.6 | 7.3 | 0.6 | 3.2 | 0.6 | 4.4 |
| 0.65 | 3.0 | 0.65 | 7.3 | 0.65 | 3.2 | 0.65 | 4.4 |
| 0.7 | 3.0 | 0.7 | 7.3 | 0.7 | 3.2 | 0.7 | 4.4 |
| 0.75 | 2.9 | 0.75 | 7.1 | 0.75 | 3.1 | 0.75 | 4.3 |
| 0.8 | 2.8 | 0.8 | 6.8 | 0.8 | 3.0 | 0.8 | 4.1 |

-continued

| | | | | | | | |
|---|---|---|---|---|---|---|---|
| 0.85 | 2.6 | 0.85 | 6.3 | 0.85 | 2.8 | 0.85 | 3.7 |
| 0.9 | 2.3 | 0.9 | 5.3 | 0.9 | 2.4 | 0.9 | 3.2 |
| 0.95 | 1.8 | 0.95 | 3.7 | 0.95 | 1.9 | 0.95 | 2.4 |
| 1 | 1.2 | 1 | 1.2 | 1 | 1.2 | 1 | 1.2 |

HF - HCFO-1233xf - HFO-1234yf - HFO-1243zf

| Organics 0.9 F1233xf + 0.05 F1234yf + 0.05 F1243zf | | Organics 0.05 F1233xf + 0.9 F1234yf + 0.05 F1243zf | | Organics 0.05 F1233xf + 0.05 F1234yf + 0.9 F1243zf | | Organics 0.4 F1233xf + 0.3 F1234yf + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 6.5 | 0 | 5.8 | 0 | 4.6 |
| 0.05 | 3.2 | 0.05 | 7.5 | 0.05 | 6.8 | 0.05 | 5.6 |
| 0.1 | 3.2 | 0.1 | 7.5 | 0.1 | 6.8 | 0.1 | 5.7 |
| 0.15 | 3.2 | 0.15 | 7.5 | 0.15 | 6.8 | 0.15 | 5.6 |
| 0.2 | 3.2 | 0.2 | 7.5 | 0.2 | 6.8 | 0.2 | 5.6 |
| 0.25 | 3.2 | 0.25 | 7.5 | 0.25 | 6.8 | 0.25 | 5.6 |
| 0.3 | 3.2 | 0.3 | 7.5 | 0.3 | 6.8 | 0.3 | 5.6 |
| 0.35 | 3.2 | 0.35 | 7.5 | 0.35 | 6.8 | 0.35 | 5.6 |
| 0.4 | 3.2 | 0.4 | 7.5 | 0.4 | 6.8 | 0.4 | 5.6 |
| 0.45 | 3.2 | 0.45 | 7.5 | 0.45 | 6.8 | 0.45 | 5.6 |
| 0.5 | 3.2 | 0.5 | 7.5 | 0.5 | 6.8 | 0.5 | 5.6 |
| 0.55 | 3.2 | 0.55 | 7.5 | 0.55 | 6.7 | 0.55 | 5.6 |
| 0.6 | 3.2 | 0.6 | 7.5 | 0.6 | 6.7 | 0.6 | 5.6 |
| 0.65 | 3.2 | 0.65 | 7.5 | 0.65 | 6.7 | 0.65 | 5.6 |
| 0.7 | 3.2 | 0.7 | 7.4 | 0.7 | 6.6 | 0.7 | 5.6 |
| 0.75 | 3.2 | 0.75 | 7.3 | 0.75 | 6.4 | 0.75 | 5.4 |
| 0.8 | 3.0 | 0.8 | 7.0 | 0.8 | 6.1 | 0.8 | 5.1 |
| 0.85 | 2.8 | 0.85 | 6.4 | 0.85 | 5.6 | 0.85 | 4.7 |
| 0.9 | 2.4 | 0.9 | 5.4 | 0.9 | 4.8 | 0.9 | 4.0 |
| 0.95 | 1.9 | 0.95 | 3.7 | 0.95 | 3.4 | 0.95 | 2.9 |
| 1 | 1.2 | 1 | 1.2 | 1 | 1.2 | 1 | 1.2 |

HF - HFO-1234yf - HCFO-1233xf - HCFC-244bb

| Organics 0.9 F1233xf + 0.05 F1234yf + 0.05 F244bb | | Organics 0.05 F1233xf + 0.9 F1234yf + 0.05 F244bb | | Organics 0.05 F1233xf + 0.05 F1234yf + 0.9 F244bb | | Organics 0.4 F1233xf + 0.3 F1234yf + 0.3 F244bb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.1 | 0 | 3.1 |
| 0.05 | 2.9 | 0.05 | 7.3 | 0.05 | 2.2 | 0.05 | 4.2 |
| 0.1 | 2.9 | 0.1 | 7.3 | 0.1 | 2.2 | 0.1 | 4.2 |
| 0.15 | 2.9 | 0.15 | 7.3 | 0.15 | 2.2 | 0.15 | 4.2 |
| 0.2 | 2.9 | 0.2 | 7.3 | 0.2 | 2.2 | 0.2 | 4.2 |
| 0.25 | 2.9 | 0.25 | 7.3 | 0.25 | 2.2 | 0.25 | 4.2 |
| 0.3 | 2.9 | 0.3 | 7.3 | 0.3 | 2.2 | 0.3 | 4.2 |
| 0.35 | 2.9 | 0.35 | 7.3 | 0.35 | 2.2 | 0.35 | 4.2 |
| 0.4 | 2.9 | 0.4 | 7.3 | 0.4 | 2.2 | 0.4 | 4.2 |
| 0.45 | 2.9 | 0.45 | 7.3 | 0.45 | 2.2 | 0.45 | 4.2 |
| 0.5 | 2.9 | 0.5 | 7.3 | 0.5 | 2.2 | 0.5 | 4.1 |
| 0.55 | 2.9 | 0.55 | 7.3 | 0.55 | 2.2 | 0.55 | 4.1 |
| 0.6 | 2.9 | 0.6 | 7.3 | 0.6 | 2.2 | 0.6 | 4.1 |
| 0.65 | 2.9 | 0.65 | 7.3 | 0.65 | 2.2 | 0.65 | 4.1 |
| 0.7 | 2.9 | 0.7 | 7.3 | 0.7 | 2.1 | 0.7 | 4.0 |
| 0.75 | 2.9 | 0.75 | 7.1 | 0.75 | 2.1 | 0.75 | 4.0 |
| 0.8 | 2.8 | 0.8 | 6.8 | 0.8 | 2.1 | 0.8 | 3.9 |
| 0.85 | 2.6 | 0.85 | 6.2 | 0.85 | 2.1 | 0.85 | 3.5 |
| 0.9 | 2.2 | 0.9 | 5.2 | 0.9 | 1.9 | 0.9 | 3.1 |

-continued

| 0.95 | 1.8 | 0.95 | 3.6 | 0.95 | 1.6 | 0.95 | 2.3 |
| 1 | 1.2 | 1 | 1.2 | 1 | 1.2 | 1 | 1.2 |

HF - HCFO-1233xf - HFC-245cb - HCFC-244bb

| Organics 0.9 F1233xf + 0.05 F245cb + 0.05 F244bb | | Organics 0.05 F1233xf + 0.9 F245cb + 0.05 F244bb | | Organics 0.05 F1233xf + 0.05 F245cb + 0.9 F244bb | | Organics 0.4 F1233xf + 0.3 F245cb + 0.3 F244bb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.3 | 0 | 0.9 | 0 | 2.3 |
| 0.05 | 2.8 | 0.05 | 5.5 | 0.05 | 2.1 | 0.05 | 3.4 |
| 0.1 | 2.8 | 0.1 | 5.5 | 0.1 | 2.1 | 0.1 | 3.4 |
| 0.15 | 2.8 | 0.15 | 5.5 | 0.15 | 2.1 | 0.15 | 3.4 |
| 0.2 | 2.8 | 0.2 | 5.5 | 0.2 | 2.1 | 0.2 | 3.4 |
| 0.25 | 2.8 | 0.25 | 5.5 | 0.25 | 2.1 | 0.25 | 3.4 |
| 0.3 | 2.8 | 0.3 | 5.5 | 0.3 | 2.1 | 0.3 | 3.4 |
| 0.35 | 2.8 | 0.35 | 5.5 | 0.35 | 2.1 | 0.35 | 3.4 |
| 0.4 | 2.8 | 0.4 | 5.5 | 0.4 | 2.1 | 0.4 | 3.4 |
| 0.45 | 2.8 | 0.45 | 5.5 | 0.45 | 2.1 | 0.45 | 3.4 |
| 0.5 | 2.8 | 0.5 | 5.5 | 0.5 | 2.1 | 0.5 | 3.4 |
| 0.55 | 2.8 | 0.55 | 5.5 | 0.55 | 2.1 | 0.55 | 3.4 |
| 0.6 | 2.8 | 0.6 | 5.5 | 0.6 | 2.0 | 0.6 | 3.4 |
| 0.65 | 2.8 | 0.65 | 5.5 | 0.65 | 2.0 | 0.65 | 3.4 |
| 0.7 | 2.8 | 0.7 | 5.5 | 0.7 | 2.0 | 0.7 | 3.4 |
| 0.75 | 2.8 | 0.75 | 5.5 | 0.75 | 2.0 | 0.75 | 3.4 |
| 0.8 | 2.7 | 0.8 | 5.5 | 0.8 | 2.0 | 0.8 | 3.4 |
| 0.85 | 2.5 | 0.85 | 5.5 | 0.85 | 2.0 | 0.85 | 3.3 |
| 0.9 | 2.2 | 0.9 | 4.7 | 0.9 | 1.9 | 0.9 | 2.9 |
| 0.95 | 1.8 | 0.95 | 3.4 | 0.95 | 1.6 | 0.95 | 2.2 |
| 1 | 1.2 | 1 | 1.2 | 1 | 1.2 | 1 | 1.2 |

Example 5: Temperature and Pressure Range of Quaternary Mixtures

| | Boiling point range | |
|---|---|---|
| Quaternary | Temperature ° C. | Pressure bar abs |
| HF-HCFO-1233xf-HFC-245cb-HCFO-1233zdE | 0 to 40 | ⁻1.0 to ⁻8.7 |
| HF-HCFO-1233xf-HFC-245cb-HFO-1234zeE | 0 to 40 | ⁻1.1 to ⁻8.8 |
| HF-HCFO-1233xf-HFC-245cb-HFO-1234zeZ | 0 to 40 | ⁻1.1 to ⁻8.8 |
| HF-HCFO-1233xf-HFC-245cb-HFO-1243zf | 0 to 40 | ⁻1.2 to ⁻10.1 |
| HF-HCFO-1233xf-HCFO-1233zdE-HFO-1234zeE | 0 to 40 | ⁻1.0 to ⁻8.6 |
| HF-HCFO-1233xf-HCFO-1233zdE-HFO-1234zeZ | 0 to 40 | ⁻0.9 to ⁻4.8 |
| HF-HCFO-1233xf-HCFO-1233zdE-HFO-1243zf | 0 to 40 | ⁻1.0 to ⁻9.9 |
| HF-HCFO-1233xf-HFO-1234zeE-HFO-1234zeZ | 0 to 40 | ⁻1.1 to ⁻8.6 |
| HF-HCFO-1233xf-HFO-1234zeE-HFO-1243zf | 0 to 40 | ⁻1.2 to ⁻10.1 |
| HF-HCFO-1233xf-HFO-1234zeZ-HFO-1243zf | 0 to 40 | ⁻1.1 to ⁻9.9 |
| HF-HCFO-1233xf-HFC-245cb-HFO-1234yf | 0 to 40 | ⁻1.2 to ⁻10.0 |
| HF-HCFO-1233xf-HFO-1234yf-HCFO-1233zdE | 0 to 40 | ⁻1.0 to ⁻11.1 |
| HF-HCFO-1233xf-HFO-1234yf-HFO-1234zeE | 0 to 40 | ⁻1.2 to ⁻11.3 |
| HF-HCFO-1233xf-HFO-1234yf-HFO-1234zeZ | 0 to 40 | ⁻1.0 to ⁻11.0 |
| HF-HCFO-1233xf-HFO-1234yf-HFO-1243zf | 0 to 40 | ⁻1.3 to ⁻11.3 |
| HF-HFO-1234yf-HCFO-1233xf-HCFC-244bb | 0 to 40 | ⁻0.8 to ⁻11.0 |
| HF-HCFO-1233xf-HFC-245cb-HCFC-244bb | 0 to 40 | ⁻0.7 to ⁻8.6 |

Example 6: Decantation Range of Quaternary Mixtures

| Quaternary HF-Orga1 Orga2 Orga3 | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HFO-1234yf | 5-75 | 5-75 | 15-70 |
| HF-HCFO-1233xf-HFC-245cb-HCFO-1233zdE | 5-80 | 5-75 | 5-70 |
| HF-HCFO-1233xf-HFC-245cb-HFO-1234zeE | 5-75 | 5-70 | 15-60 |
| HF-HCFO-1233xf-HFC-245cb-HFO-1234zeZ | 5-80 | 5-75 | 5-70 |
| HF-HCFO-1233xf-HFC-245cb-HFO-1243zf | 5-75 | 5-70 | 15-60 |
| HF-HCFO-1233xf-HFO-1234yf-HCFO-1233zdE | 5-75 | 5-70 | 10-60 |
| HF-HCFO-1233xf-HFO-1234yf-HFO-1234zeE | 5-70 | 10-60 | * |
| HF-HCFO-1233xf-HFO-1234yf-HFO-1234zeZ | 5-75 | 5-70 | 10-60 |
| HF-HCFO-1233xf-HFO-1234yf-HFO-1243zf | 5-75 | 10-65 | * |
| HF-HCFO-1233xf-HCFO-1233zdE-HFO-1234zeE | 5-75 | 5-65 | 5-55 |
| HF-HCFO-1233xf-HCFO-1233zdE-HFO-1234zeZ | 5-80 | 5-75 | 5-65 |
| HF-HCFO-1233xf-HCFO-1233zdE-HFO-1243zf | 5-75 | 5-70 | 10-60 |
| HF-HCFO-1233xf-HFO-1234zeE-HFO-1234zeZ | 5-75 | 5-65 | 10-55 |
| HF-HCFO-1233xf-HFO-1234zeE-HFO-1243zf | 5-70 | 10-60 | * |
| HF-HCFO-1233xf-HFO-1234zeZ-HFO-1243zf | 5-75 | 5-70 | 10-55 |
| HF-HFO-1234yf-HCFO-1233xf-HCFC-244bb | 1-80 | 20-99 | 5-75 |
| HF-HCFO-1233xf-HFC-245cb-HCFC-244bb | 1-85 | 15-99 | 5-80 |

Example 7: Pentenary Mixtures, Isotherm at 25° C.

| HF - HCFO-1233xf- HFC-245cb - HCFO-1233zdE - HFO-1234zeE | | | | | | | | | |
|---|---|---|---|---|---|---|---|---|---|
| Organics 0.9 F1233xf + 0.033 F1233zdE + 0.033 F245cb + 0.034 F1234zeE | | Organics 0.033 F1233xf + 0.9 F1233zdE + 0.033 F245cb + 0.034 F1234zeE | | Organics 0.033 F1233xf + 0.033 F1233zdE + 0.9 245cb + 0.034 F1234zeE | | Organics 0.034 F1233xf + 0.033 F1233zdE + 0.033 F245cb + 0.9 F1234zeE | | Organics 0.25 F1233xf + 0.25 F1233zdE + 0.25 F245cb + 0.25 F1234zeE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.4 | 0 | 4.7 | 0 | 3.2 |
| 0.05 | 2.9 | 0.05 | 2.7 | 0.05 | 5.6 | 0.05 | 5.6 | 0.05 | 4.3 |
| 0.1 | 2.9 | 0.1 | 2.7 | 0.1 | 5.6 | 0.1 | 5.6 | 0.1 | 4.3 |
| 0.15 | 2.9 | 0.15 | 2.7 | 0.15 | 5.6 | 0.15 | 5.6 | 0.15 | 4.3 |
| 0.2 | 2.9 | 0.2 | 2.7 | 0.2 | 5.6 | 0.2 | 5.6 | 0.2 | 4.3 |
| 0.25 | 2.9 | 0.25 | 2.7 | 0.25 | 5.6 | 0.25 | 5.6 | 0.25 | 4.3 |
| 0.3 | 2.9 | 0.3 | 2.7 | 0.3 | 5.6 | 0.3 | 5.6 | 0.3 | 4.3 |
| 0.35 | 2.9 | 0.35 | 2.7 | 0.35 | 5.6 | 0.35 | 5.6 | 0.35 | 4.3 |
| 0.4 | 2.9 | 0.4 | 2.7 | 0.4 | 5.6 | 0.4 | 5.6 | 0.4 | 4.3 |
| 0.45 | 2.9 | 0.45 | 2.7 | 0.45 | 5.6 | 0.45 | 5.6 | 0.45 | 4.3 |
| 0.5 | 2.9 | 0.5 | 2.7 | 0.5 | 5.6 | 0.5 | 5.6 | 0.5 | 4.3 |
| 0.55 | 2.9 | 0.55 | 2.7 | 0.55 | 5.6 | 0.55 | 5.6 | 0.55 | 4.3 |
| 0.6 | 2.9 | 0.6 | 2.7 | 0.6 | 5.6 | 0.6 | 5.5 | 0.6 | 4.3 |
| 0.65 | 2.9 | 0.65 | 2.7 | 0.65 | 5.6 | 0.65 | 5.4 | 0.65 | 4.3 |
| 0.7 | 2.9 | 0.7 | 2.7 | 0.7 | 5.7 | 0.7 | 5.2 | 0.7 | 4.3 |
| 0.75 | 2.9 | 0.75 | 2.7 | 0.75 | 5.7 | 0.75 | 5.0 | 0.75 | 4.2 |
| 0.8 | 2.7 | 0.8 | 2.6 | 0.8 | 5.7 | 0.8 | 4.7 | 0.8 | 4.0 |
| 0.85 | 2.5 | 0.85 | 2.4 | 0.85 | 5.6 | 0.85 | 4.2 | 0.85 | 3.7 |
| 0.9 | 2.2 | 0.9 | 2.1 | 0.9 | 4.8 | 0.9 | 3.5 | 0.9 | 3.2 |
| 0.95 | 1.8 | 0.95 | 1.7 | 0.95 | 3.4 | 0.95 | 2.5 | 0.95 | 2.4 |
| 1 | 1.2 | 1 | 1.2 | 1 | 1.2 | 1 | 1.2 | 1 | 1.2 |

| HF - HCFO-1233xf - HFC-245cb - HCFO-1233zdE - HFO-1234zeZ | | | | | | | | | |
|---|---|---|---|---|---|---|---|---|---|
| Organics 0.9 F1233xf + 0.033 F1233zdE + 0.033 F245cb + 0.034 F1234zeZ | | Organics 0.033 F1233xf + 0.9 F1233zdE + 0.033 F245cb + 0.034 F1234zeZ | | Organics 0.033 F1233xf + 0.033 F1233zdE + 0.9 F245cb + 0.034 F1234zeZ | | Organics 0.034 F1233xf + 0.033 F1233zdE + 0.033 F245cb + 0.9 F1234zeZ | | Organics 0.25 F1233xf + 0.25 F1233zdE + 0.25 F245cb + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.3 | 0 | 1.9 | 0 | 2.3 |
| 0.05 | 2.8 | 0.05 | 2.6 | 0.05 | 5.5 | 0.05 | 3.0 | 0.05 | 3.5 |
| 0.1 | 2.8 | 0.1 | 2.6 | 0.1 | 5.5 | 0.1 | 3.0 | 0.1 | 3.5 |
| 0.15 | 2.8 | 0.15 | 2.6 | 0.15 | 5.5 | 0.15 | 3.0 | 0.15 | 3.5 |

-continued

| MASSFRAC | PRESSURE bar | MASSFRAC | PRESSURE bar | MASSFRAC | PRESSURE bar | MASSFRAC | PRESSURE bar | MASSFRAC | PRESSURE bar |
|---|---|---|---|---|---|---|---|---|---|
| 0.2 | 2.8 | 0.2 | 2.6 | 0.2 | 5.5 | 0.2 | 3.0 | 0.2 | 3.5 |
| 0.25 | 2.8 | 0.25 | 2.6 | 0.25 | 5.5 | 0.25 | 3.0 | 0.25 | 3.5 |
| 0.3 | 2.8 | 0.3 | 2.6 | 0.3 | 5.5 | 0.3 | 3.0 | 0.3 | 3.5 |
| 0.35 | 2.8 | 0.35 | 2.6 | 0.35 | 5.5 | 0.35 | 3.0 | 0.35 | 3.5 |
| 0.4 | 2.8 | 0.4 | 2.6 | 0.4 | 5.5 | 0.4 | 3.0 | 0.4 | 3.5 |
| 0.45 | 2.8 | 0.45 | 2.6 | 0.45 | 5.5 | 0.45 | 3.0 | 0.45 | 3.5 |
| 0.5 | 2.8 | 0.5 | 2.6 | 0.5 | 5.5 | 0.5 | 3.0 | 0.5 | 3.5 |
| 0.55 | 2.8 | 0.55 | 2.6 | 0.55 | 5.5 | 0.55 | 3.0 | 0.55 | 3.5 |
| 0.6 | 2.8 | 0.6 | 2.6 | 0.6 | 5.5 | 0.6 | 3.0 | 0.6 | 3.5 |
| 0.65 | 2.8 | 0.65 | 2.6 | 0.65 | 5.5 | 0.65 | 3.0 | 0.65 | 3.6 |
| 0.7 | 2.8 | 0.7 | 2.6 | 0.7 | 5.6 | 0.7 | 3.0 | 0.7 | 3.6 |
| 0.75 | 2.8 | 0.75 | 2.6 | 0.75 | 5.6 | 0.75 | 3.0 | 0.75 | 3.6 |
| 0.8 | 2.7 | 0.8 | 2.5 | 0.8 | 5.6 | 0.8 | 2.9 | 0.8 | 3.5 |
| 0.85 | 2.5 | 0.85 | 2.3 | 0.85 | 5.5 | 0.85 | 2.7 | 0.85 | 3.3 |
| 0.9 | 2.2 | 0.9 | 2.1 | 0.9 | 4.8 | 0.9 | 2.4 | 0.9 | 2.8 |
| 0.95 | 1.8 | 0.95 | 1.7 | 0.95 | 3.4 | 0.95 | 1.9 | 0.95 | 2.2 |
| 1 | 1.2 | 1 | 1.2 | 1 | 1.2 | 1 | 1.2 | 1 | 1.2 |

HF - HCFO-1233xf - HFC-245cb - HCFO-1233zdE - HFO-1243zf

| Organics 0.9 F1233xf + 0.033 F1233zdE + 0.033 F245cb + 0.034 F1243zf | | Organics 0.033 F1233xf + 0.9 F1233zdE + 0.033 F245cb + 0.034 F1243zf | | Organics 0.033 F1233xf + 0.033 F1233zdE + 0.9 F245cb + 0.034 F1243zf | | Organics 0.034 F1233xf + 0.033 F1233zdE + 0.033 F245cb + 0.9 F1243zf | | Organics 0.25 F1233xf + 0.25 F1233zdE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.5 | 0 | 5.6 | 0 | 3.5 |
| 0.05 | 3.0 | 0.05 | 2.8 | 0.05 | 5.7 | 0.05 | 6.5 | 0.05 | 4.6 |
| 0.1 | 3.0 | 0.1 | 2.8 | 0.1 | 5.7 | 0.1 | 6.6 | 0.1 | 4.6 |
| 0.15 | 3.0 | 0.15 | 2.8 | 0.15 | 5.7 | 0.15 | 6.6 | 0.15 | 4.6 |
| 0.2 | 3.0 | 0.2 | 2.8 | 0.2 | 5.7 | 0.2 | 6.5 | 0.2 | 4.6 |
| 0.25 | 3.0 | 0.25 | 2.8 | 0.25 | 5.7 | 0.25 | 6.5 | 0.25 | 4.6 |
| 0.3 | 3.0 | 0.3 | 2.8 | 0.3 | 5.7 | 0.3 | 6.5 | 0.3 | 4.6 |
| 0.35 | 2.9 | 0.35 | 2.8 | 0.35 | 5.7 | 0.35 | 6.5 | 0.35 | 4.6 |
| 0.4 | 2.9 | 0.4 | 2.8 | 0.4 | 5.7 | 0.4 | 6.5 | 0.4 | 4.6 |
| 0.45 | 2.9 | 0.45 | 2.7 | 0.45 | 5.7 | 0.45 | 6.5 | 0.45 | 4.6 |
| 0.5 | 2.9 | 0.5 | 2.7 | 0.5 | 5.7 | 0.5 | 6.5 | 0.5 | 4.6 |
| 0.55 | 2.9 | 0.55 | 2.7 | 0.55 | 5.7 | 0.55 | 6.5 | 0.55 | 4.6 |
| 0.6 | 2.9 | 0.6 | 2.7 | 0.6 | 5.7 | 0.6 | 6.5 | 0.6 | 4.6 |
| 0.65 | 2.9 | 0.65 | 2.7 | 0.65 | 5.7 | 0.65 | 6.4 | 0.65 | 4.6 |
| 0.7 | 2.9 | 0.7 | 2.7 | 0.7 | 5.7 | 0.7 | 6.4 | 0.7 | 4.7 |
| 0.75 | 2.9 | 0.75 | 2.7 | 0.75 | 5.7 | 0.75 | 6.2 | 0.75 | 4.6 |
| 0.8 | 2.8 | 0.8 | 2.6 | 0.8 | 5.7 | 0.8 | 5.9 | 0.8 | 4.4 |
| 0.85 | 2.6 | 0.85 | 2.4 | 0.85 | 5.6 | 0.85 | 5.4 | 0.85 | 4.1 |
| 0.9 | 2.3 | 0.9 | 2.2 | 0.9 | 4.8 | 0.9 | 4.6 | 0.9 | 3.5 |
| 0.95 | 1.8 | 0.95 | 1.8 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF - HCFO-1233xf - HFC-245cb - HFO-1234zeE - HFO-1234zeZ

| Organics 0.9 F1233xf + 0.033 F1234zeE + 0.033 F245cb + 0.034 F1234zeZ | | Organics 0.033 F1233xf + 0.9 1234zeE + 0.033 F245cb + 0.034 F1234zeZ | | Organics 0.033 F1233xf + 0.033 F1234zeE + 0.9 F245cb + 0.034 F1234zeZ | | Organics 0.034 F1233xf + 0.033 F1234zeE + 0.033 F245cb + 0.9 F1234zeZ | | Organics 0.25 F1233xf + 0.25 F1234zeE + 0.25 F245cb + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 4.7 | 0 | 4.5 | 0 | 2.0 | 0 | 3.2 |
| 0.05 | 2.9 | 0.05 | 5.6 | 0.05 | 5.6 | 0.05 | 3.1 | 0.05 | 4.3 |
| 0.1 | 2.9 | 0.1 | 5.7 | 0.1 | 5.6 | 0.1 | 3.1 | 0.1 | 4.3 |
| 0.15 | 2.9 | 0.15 | 5.6 | 0.15 | 5.6 | 0.15 | 3.1 | 0.15 | 4.3 |
| 0.2 | 2.9 | 0.2 | 5.6 | 0.2 | 5.6 | 0.2 | 3.1 | 0.2 | 4.3 |
| 0.25 | 2.9 | 0.25 | 5.6 | 0.25 | 5.6 | 0.25 | 3.1 | 0.25 | 4.3 |
| 0.3 | 2.9 | 0.3 | 5.6 | 0.3 | 5.6 | 0.3 | 3.1 | 0.3 | 4.3 |
| 0.35 | 2.9 | 0.35 | 5.6 | 0.35 | 5.6 | 0.35 | 3.1 | 0.35 | 4.3 |
| 0.4 | 2.9 | 0.4 | 5.6 | 0.4 | 5.6 | 0.4 | 3.1 | 0.4 | 4.3 |
| 0.45 | 2.9 | 0.45 | 5.6 | 0.45 | 5.6 | 0.45 | 3.1 | 0.45 | 4.3 |
| 0.5 | 2.9 | 0.5 | 5.6 | 0.5 | 5.6 | 0.5 | 3.1 | 0.5 | 4.3 |
| 0.55 | 2.9 | 0.55 | 5.6 | 0.55 | 5.6 | 0.55 | 3.1 | 0.55 | 4.3 |
| 0.6 | 2.9 | 0.6 | 5.5 | 0.6 | 5.6 | 0.6 | 3.1 | 0.6 | 4.3 |
| 0.65 | 2.9 | 0.65 | 5.4 | 0.65 | 5.7 | 0.65 | 3.1 | 0.65 | 4.4 |
| 0.7 | 2.9 | 0.7 | 5.2 | 0.7 | 5.7 | 0.7 | 3.1 | 0.7 | 4.4 |
| 0.75 | 2.9 | 0.75 | 5.0 | 0.75 | 5.7 | 0.75 | 3.1 | 0.75 | 4.3 |
| 0.8 | 2.7 | 0.8 | 4.7 | 0.8 | 5.7 | 0.8 | 3.0 | 0.8 | 4.1 |

-continued

| | | | | | | | | | |
|---|---|---|---|---|---|---|---|---|---|
| 0.85 | 2.5 | 0.85 | 4.2 | 0.85 | 5.6 | 0.85 | 2.7 | 0.85 | 3.8 |
| 0.9 | 2.2 | 0.9 | 3.5 | 0.9 | 4.8 | 0.9 | 2.4 | 0.9 | 3.3 |
| 0.95 | 1.8 | 0.95 | 2.6 | 0.95 | 3.4 | 0.95 | 1.9 | 0.95 | 2.4 |
| 1 | 1.2 | 1 | 1.2 | 1 | 1.2 | 1 | 1.2 | 1 | 1.2 |

HF - HCFO-1233xf - HFC-245cb - HFO-1234zeE - HFO-1243zf

| Organics 0.9 F1233xf + 0.033 F1234zeE + 0.033 F245cb + 0.034 F1243zf | | Organics 0.033 F1233xf + 0.9 F1234zeE + 0.033 F245cb + 0.034 F1243zf | | Organics 0.033 F1233xf + 0.033 F1234zeE + 0.9 F245cb + 0.034 F1243zf | | Organics 0.034 F1233xf + 0.033 F1234zeE + 0.033 F245cb + 0.9 F1243zf | | Organics 0.25 F1233xf + 0.25 F1234zeE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 5.7 | 0 | 4.4 |
| 0.05 | 3.1 | 0.05 | 5.8 | 0.05 | 5.8 | 0.05 | 6.6 | 0.05 | 5.4 |
| 0.1 | 3.1 | 0.1 | 5.8 | 0.1 | 5.8 | 0.1 | 6.7 | 0.1 | 5.4 |
| 0.15 | 3.1 | 0.15 | 5.8 | 0.15 | 5.8 | 0.15 | 6.6 | 0.15 | 5.4 |
| 0.2 | 3.1 | 0.2 | 5.8 | 0.2 | 5.8 | 0.2 | 6.6 | 0.2 | 5.4 |
| 0.25 | 3.1 | 0.25 | 5.8 | 0.25 | 5.8 | 0.25 | 6.6 | 0.25 | 5.4 |
| 0.3 | 3.1 | 0.3 | 5.8 | 0.3 | 5.8 | 0.3 | 6.6 | 0.3 | 5.4 |
| 0.35 | 3.1 | 0.35 | 5.8 | 0.35 | 5.8 | 0.35 | 6.6 | 0.35 | 5.4 |
| 0.4 | 3.1 | 0.4 | 5.8 | 0.4 | 5.8 | 0.4 | 6.6 | 0.4 | 5.4 |
| 0.45 | 3.1 | 0.45 | 5.8 | 0.45 | 5.8 | 0.45 | 6.6 | 0.45 | 5.4 |
| 0.5 | 3.1 | 0.5 | 5.7 | 0.5 | 5.8 | 0.5 | 6.6 | 0.5 | 5.4 |
| 0.55 | 3.1 | 0.55 | 5.7 | 0.55 | 5.8 | 0.55 | 6.6 | 0.55 | 5.4 |
| 0.6 | 3.1 | 0.6 | 5.6 | 0.6 | 5.8 | 0.6 | 6.6 | 0.6 | 5.4 |
| 0.65 | 3.1 | 0.65 | 5.5 | 0.65 | 5.8 | 0.65 | 6.5 | 0.65 | 5.4 |
| 0.7 | 3.1 | 0.7 | 5.4 | 0.7 | 5.8 | 0.7 | 6.4 | 0.7 | 5.4 |
| 0.75 | 3.0 | 0.75 | 5.2 | 0.75 | 5.8 | 0.75 | 6.3 | 0.75 | 5.3 |
| 0.8 | 2.9 | 0.8 | 4.8 | 0.8 | 5.8 | 0.8 | 6.0 | 0.8 | 5.0 |
| 0.85 | 2.7 | 0.85 | 4.3 | 0.85 | 5.7 | 0.85 | 5.5 | 0.85 | 4.6 |
| 0.9 | 2.3 | 0.9 | 3.6 | 0.9 | 4.9 | 0.9 | 4.7 | 0.9 | 3.9 |
| 0.95 | 1.9 | 0.95 | 2.6 | 0.95 | 3.5 | 0.95 | 3.3 | 0.95 | 2.8 |
| 1 | 1.2 | 1 | 1.2 | 1 | 1.2 | 1 | 1.2 | 1 | 1.2 |

HF - HCFO-1233xf - HFC-245cb - HFO-1234zeZ - HFO-1243zf

| Organics 0.9 F1233xf + 0.033 F1234zeZ + 0.033 F245cb + 0.034 F1243zf | | Organics 0.033 F1233xf + 0.9 F1234zeZ + 0.033 F245cb + 0.034 F1243zf | | Organics 0.033 F1233xf + 0.033 F1234zeZ + 0.9 F245cb + 0.034 F1243zf | | Organics 0.034 F1233xf + 0.033 F1234zeZ + 0.033 F245cb + 0.9 F1243zf | | Organics 0.25 F1233xf + 0.25 F1234zeZ + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 5.6 | 0 | 3.6 |
| 0.05 | 3.0 | 0.05 | 3.2 | 0.05 | 5.7 | 0.05 | 6.5 | 0.05 | 4.7 |
| 0.1 | 3.0 | 0.1 | 3.2 | 0.1 | 5.7 | 0.1 | 6.6 | 0.1 | 4.7 |
| 0.15 | 3.0 | 0.15 | 3.2 | 0.15 | 5.7 | 0.15 | 6.6 | 0.15 | 4.7 |
| 0.2 | 3.0 | 0.2 | 3.2 | 0.2 | 5.7 | 0.2 | 6.6 | 0.2 | 4.7 |
| 0.25 | 3.0 | 0.25 | 3.2 | 0.25 | 5.7 | 0.25 | 6.5 | 0.25 | 4.7 |
| 0.3 | 3.0 | 0.3 | 3.2 | 0.3 | 5.7 | 0.3 | 6.5 | 0.3 | 4.7 |
| 0.35 | 3.0 | 0.35 | 3.2 | 0.35 | 5.7 | 0.35 | 6.5 | 0.35 | 4.7 |
| 0.4 | 3.0 | 0.4 | 3.2 | 0.4 | 5.7 | 0.4 | 6.5 | 0.4 | 4.7 |
| 0.45 | 3.0 | 0.45 | 3.2 | 0.45 | 5.7 | 0.45 | 6.5 | 0.45 | 4.7 |
| 0.5 | 3.0 | 0.5 | 3.2 | 0.5 | 5.7 | 0.5 | 6.5 | 0.5 | 4.7 |
| 0.55 | 3.0 | 0.55 | 3.2 | 0.55 | 5.7 | 0.55 | 6.5 | 0.55 | 4.7 |
| 0.6 | 3.0 | 0.6 | 3.2 | 0.6 | 5.7 | 0.6 | 6.5 | 0.6 | 4.7 |
| 0.65 | 3.0 | 0.65 | 3.2 | 0.65 | 5.7 | 0.65 | 6.5 | 0.65 | 4.7 |
| 0.7 | 3.0 | 0.7 | 3.2 | 0.7 | 5.7 | 0.7 | 6.4 | 0.7 | 4.7 |
| 0.75 | 3.0 | 0.75 | 3.2 | 0.75 | 5.7 | 0.75 | 6.2 | 0.75 | 4.7 |
| 0.8 | 2.8 | 0.8 | 3.0 | 0.8 | 5.7 | 0.8 | 5.9 | 0.8 | 4.5 |
| 0.85 | 2.6 | 0.85 | 2.8 | 0.85 | 5.6 | 0.85 | 5.4 | 0.85 | 4.2 |
| 0.9 | 2.3 | 0.9 | 2.5 | 0.9 | 4.8 | 0.9 | 4.6 | 0.9 | 3.6 |
| 0.95 | 1.8 | 0.95 | 1.9 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF - HCFO-1233xf - HCFO-1233zdE - HFO-1234zeE 5 - HFO-1234zeZ

| Organics 0.9 F1233xf + 0.033 F1234zeE + 0.033 F1233zdE + 0.034 F1234zeZ | | Organics 0.033 F1233xf + 0.9 F1234zeE + 0.033 F1233zdE + 0.034 F1234zeZ | | Organics 0.033 F1233xf + 0.033 F1233zdE + 0.9 F1234zeE + 0.034 F1234zeZ | | Organics 0.034 F1233xf + 0.033 F1234zeE + 0.9 F1233zdE + 0.034 F1234zeZ | | Organics 0.25 F1233xf + 0.25 F1234zeE + 0.25 F1233zdE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.5 | 0 | 1.9 | 0 | 2.4 |
| 0.05 | 2.8 | 0.05 | 5.5 | 0.05 | 2.6 | 0.05 | 3.0 | 0.05 | 3.5 |
| 0.1 | 2.8 | 0.1 | 5.5 | 0.1 | 2.6 | 0.1 | 3.0 | 0.1 | 3.5 |
| 0.15 | 2.8 | 0.15 | 5.5 | 0.15 | 2.6 | 0.15 | 3.0 | 0.15 | 3.5 |
| 0.2 | 2.8 | 0.2 | 5.5 | 0.2 | 2.6 | 0.2 | 3.0 | 0.2 | 3.5 |
| 0.25 | 2.8 | 0.25 | 5.5 | 0.25 | 2.6 | 0.25 | 3.0 | 0.25 | 3.5 |
| 0.3 | 2.8 | 0.3 | 5.5 | 0.3 | 2.6 | 0.3 | 3.0 | 0.3 | 3.5 |
| 0.35 | 2.8 | 0.35 | 5.5 | 0.35 | 2.6 | 0.35 | 3.0 | 0.35 | 3.5 |
| 0.4 | 2.8 | 0.4 | 5.5 | 0.4 | 2.6 | 0.4 | 3.0 | 0.4 | 3.5 |
| 0.45 | 2.8 | 0.45 | 5.5 | 0.45 | 2.6 | 0.45 | 3.0 | 0.45 | 3.5 |
| 0.5 | 2.8 | 0.5 | 5.5 | 0.5 | 2.6 | 0.5 | 3.0 | 0.5 | 3.5 |
| 0.55 | 2.8 | 0.55 | 5.4 | 0.55 | 2.6 | 0.55 | 3.0 | 0.55 | 3.4 |
| 0.6 | 2.8 | 0.6 | 5.4 | 0.6 | 2.6 | 0.6 | 3.0 | 0.6 | 3.4 |
| 0.65 | 2.8 | 0.65 | 5.3 | 0.65 | 2.6 | 0.65 | 3.0 | 0.65 | 3.4 |
| 0.7 | 2.8 | 0.7 | 5.1 | 0.7 | 2.5 | 0.7 | 3.0 | 0.7 | 3.4 |
| 0.75 | 2.7 | 0.75 | 4.9 | 0.75 | 2.5 | 0.75 | 3.0 | 0.75 | 3.3 |
| 0.8 | 2.6 | 0.8 | 4.6 | 0.8 | 2.4 | 0.8 | 2.8 | 0.8 | 3.1 |
| 0.85 | 2.4 | 0.85 | 4.1 | 0.85 | 2.3 | 0.85 | 2.6 | 0.85 | 2.9 |
| 0.9 | 2.1 | 0.9 | 3.4 | 0.9 | 2.0 | 0.9 | 2.3 | 0.9 | 2.5 |
| 0.95 | 1.7 | 0.95 | 2.5 | 0.95 | 1.7 | 0.95 | 1.9 | 0.95 | 1.9 |
| 1 | 1.2 | 1 | 1.2 | 1 | 1.2 | 1 | 1.2 | 1 | 1.2 |

HF - HCFO-1233xf - HCFO-1233zdE - HFO-1234zeE - HFO-1243zf

| Organics 0.9 F1233xf + 0.033 F1234zeE + 0.033 F1233zdE + 0.034 F1243zf | | Organics 0.033 F1233xf + 0.9 F1234zeE + 0.033 F1233zdE + 0.034 F1243zf | | Organics 0.033 F1233xf + 0.033 F1234zeE + 0.9 F1233zdE + 0.034 F1243zf | | Organics 0.034 F1233xf + 0.033 F1234zeE + 0.9 F1233zdE + 0.034 F1243zf | | Organics 0.25 F1233xf + 0.25 1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.6 | 0.1 | 4.7 |
| 0.15 | 3.0 | 0.15 | 5.7 | 0.15 | 2.8 | 0.15 | 6.6 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.8 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |

HF - HCFO-1233xf - HCFO-1233zdE - HFO-1234zeZ - HFO-1243zf

| Organics 0.9 F1233xf + 0.033 F1234zeZ + 0.033 F1233zdE + 0.034 F1243zf | | Organics 0.033 F1233xf + 0.9 F1234zeZ + 0.033 F1233zdE + 0.034 F1243zf | | Organics 0.033 F1233xf + 0.033 F1234zeZ + 0.9 F1233zdE + 0.034 F1243zf | | Organics 0.034 F1233xf + 0.033 F1234zeZ + 0.9 F1233zdE + 0.034 F1243zf | | Organics 0.25 F1233xf + 0.25 F1234zeZ + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |

-continued

| MASSFRAC | PRESSURE | MASSFRAC | PRESSURE | MASSFRAC | PRESSURE | MASSFRAC | PRESSURE | MASSFRAC | PRESSURE |
|---|---|---|---|---|---|---|---|---|---|
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

HF - HCFO-1233xf - HFO-1234zeE - HFO-1234zeZ - HFO-1243zf

| Organics 0.9 F1233xf + 0.033 F1234zeE + 0.033 F1234zeZ + 0.034 F1243zf | | Organics 0.033 F1233xf + 0.9 F1234zeE + 0.033 F1234zeZ + 0.034 F1243zf | | Organics 0.033 F1233xf + 0.033 F1234zeE + 0.9 F1234zeZ + 0.034 F1243zf | | Organics 0.034 F1233xf + 0.033 F1234zeE + 0.033 F1234zeZ + 0.9 F1243zf | | Organics 0.25 F1233xf + 0.25 F1234zeE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 5.6 | 0 | 3.7 |
| 0.05 | 3.0 | 0.05 | 5.7 | 0.05 | 3.2 | 0.05 | 6.5 | 0.05 | 4.7 |
| 0.1 | 3.0 | 0.1 | 5.7 | 0.1 | 3.2 | 0.1 | 6.6 | 0.1 | 4.7 |
| 0.15 | 3.0 | 0.15 | 5.7 | 0.15 | 3.2 | 0.15 | 6.6 | 0.15 | 4.7 |
| 0.2 | 3.0 | 0.2 | 5.7 | 0.2 | 3.2 | 0.2 | 6.5 | 0.2 | 4.7 |
| 0.25 | 3.0 | 0.25 | 5.7 | 0.25 | 3.2 | 0.25 | 6.5 | 0.25 | 4.7 |
| 0.3 | 3.0 | 0.3 | 5.7 | 0.3 | 3.2 | 0.3 | 6.5 | 0.3 | 4.7 |
| 0.35 | 3.0 | 0.35 | 5.7 | 0.35 | 3.2 | 0.35 | 6.5 | 0.35 | 4.7 |
| 0.4 | 3.0 | 0.4 | 5.7 | 0.4 | 3.2 | 0.4 | 6.5 | 0.4 | 4.7 |
| 0.45 | 3.0 | 0.45 | 5.7 | 0.45 | 3.2 | 0.45 | 6.5 | 0.45 | 4.7 |
| 0.5 | 3.0 | 0.5 | 5.6 | 0.5 | 3.2 | 0.5 | 6.5 | 0.5 | 4.7 |
| 0.55 | 2.9 | 0.55 | 5.6 | 0.55 | 3.1 | 0.55 | 6.5 | 0.55 | 4.6 |
| 0.6 | 2.9 | 0.6 | 5.5 | 0.6 | 3.1 | 0.6 | 6.5 | 0.6 | 4.6 |
| 0.65 | 2.9 | 0.65 | 5.4 | 0.65 | 3.1 | 0.65 | 6.4 | 0.65 | 4.6 |
| 0.7 | 2.9 | 0.7 | 5.3 | 0.7 | 3.1 | 0.7 | 6.3 | 0.7 | 4.5 |
| 0.75 | 2.9 | 0.75 | 5.0 | 0.75 | 3.1 | 0.75 | 6.2 | 0.75 | 4.4 |
| 0.8 | 2.8 | 0.8 | 4.7 | 0.8 | 3.0 | 0.8 | 5.9 | 0.8 | 4.1 |
| 0.85 | 2.6 | 0.85 | 4.2 | 0.85 | 2.7 | 0.85 | 5.4 | 0.85 | 3.8 |
| 0.9 | 2.2 | 0.9 | 3.5 | 0.9 | 2.4 | 0.9 | 4.6 | 0.9 | 3.2 |
| 0.95 | 1.8 | 0.95 | 2.5 | 0.95 | 1.9 | 0.95 | 3.3 | 0.95 | 2.4 |
| 1 | 1.2 | 1 | 1.2 | 1 | 1.2 | 1 | 1.2 | 1 | 1.2 |

HF- HCFO-1233xf- HFC-245cb - HFO-1234yf- HFO-1243zf

| Organics 0.9 F1233xf + 0.033 F1234yf + 0.033 F245cb + 0.034 F1243zf | | Organics 0.033 F1233xf + 0.9 F1234yf + 0.033 F245cb + 0.034 F1243zf | | Organics 0.033 F1233xf + 0.033 F1234yf + 0.9 F245cb + 0.034 F1243zf | | Organics 0.034 F1233xf + 0.033 F1234yf + 0.033 F245cb + 0.9 F1243zf | | Organics 0.25 F1233xf + 0.25 F1234yf + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.7 | 0 | 5.7 | 0 | 4.8 |
| 0.05 | 3.2 | 0.05 | 7.5 | 0.05 | 5.8 | 0.05 | 6.7 | 0.05 | 5.9 |
| 0.1 | 3.2 | 0.1 | 7.5 | 0.1 | 5.9 | 0.1 | 6.7 | 0.1 | 5.9 |
| 0.15 | 3.2 | 0.15 | 7.5 | 0.15 | 5.9 | 0.15 | 6.7 | 0.15 | 5.9 |
| 0.2 | 3.2 | 0.2 | 7.5 | 0.2 | 5.9 | 0.2 | 6.7 | 0.2 | 5.9 |
| 0.25 | 3.2 | 0.25 | 7.5 | 0.25 | 5.9 | 0.25 | 6.7 | 0.25 | 5.9 |
| 0.3 | 3.2 | 0.3 | 7.5 | 0.3 | 5.9 | 0.3 | 6.7 | 0.3 | 5.9 |
| 0.35 | 3.2 | 0.35 | 7.5 | 0.35 | 5.9 | 0.35 | 6.7 | 0.35 | 5.9 |
| 0.4 | 3.2 | 0.4 | 7.5 | 0.4 | 5.9 | 0.4 | 6.7 | 0.4 | 5.9 |
| 0.45 | 3.2 | 0.45 | 7.5 | 0.45 | 5.9 | 0.45 | 6.7 | 0.45 | 5.9 |
| 0.5 | 3.1 | 0.5 | 7.5 | 0.5 | 5.9 | 0.5 | 6.7 | 0.5 | 5.9 |
| 0.55 | 3.1 | 0.55 | 7.5 | 0.55 | 5.9 | 0.55 | 6.7 | 0.55 | 5.9 |
| 0.6 | 3.1 | 0.6 | 7.5 | 0.6 | 5.9 | 0.6 | 6.6 | 0.6 | 5.9 |
| 0.65 | 3.1 | 0.65 | 7.5 | 0.65 | 5.9 | 0.65 | 6.6 | 0.65 | 5.9 |
| 0.7 | 3.1 | 0.7 | 7.5 | 0.7 | 5.9 | 0.7 | 6.5 | 0.7 | 5.9 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|
| 0.75 | 3.1 | 0.75 | 7.4 | 0.75 | 5.9 | 0.75 | 6.3 | 0.75 | 5.9 |
| 0.8 | 3.0 | 0.8 | 7.0 | 0.8 | 5.9 | 0.8 | 6.1 | 0.8 | 5.6 |
| 0.85 | 2.7 | 0.85 | 6.5 | 0.85 | 5.8 | 0.85 | 5.6 | 0.85 | 5.2 |
| 0.9 | 2.4 | 0.9 | 5.4 | 0.9 | 5.0 | 0.9 | 4.7 | 0.9 | 4.4 |
| 0.95 | 1.9 | 0.95 | 3.8 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

HF - HCFO-1233xf-HFO-1234vf- HFO-1234zeE - HFO-1234zeZ

| Organics 0.9 F1233xf + 0.033 F1234zeE + 0.033 F1234zeZ + 0.034 F1234yf | | Organics 0.033 F1233xf + 0.9 F1234zeE + 0.033 F1234zeZ + 0.034 F1234yf | | Organics 0.033 F1233xf + 0.033 F1234zeE + 0.9 F1234zeZ + 0.034 F1234yf | | Organics 0.034 F1233xf + 0.033 F1234zeE + 0.033 F1234zeZ + 0.9 F1234yf | | Organics 0.25 F1233xf + 0.25 F1234zeE + 0.25 F1234zeZ + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 6.4 | 0 | 3.8 |
| 0.05 | 3.0 | 0.05 | 5.7 | 0.05 | 3.2 | 0.05 | 7.4 | 0.05 | 4.9 |
| 0.1 | 3.0 | 0.1 | 5.7 | 0.1 | 3.2 | 0.1 | 7.4 | 0.1 | 4.9 |
| 0.15 | 3.0 | 0.15 | 5.7 | 0.15 | 3.2 | 0.15 | 7.4 | 0.15 | 4.9 |
| 0.2 | 3.0 | 0.2 | 5.7 | 0.2 | 3.2 | 0.2 | 7.4 | 0.2 | 4.9 |
| 0.25 | 3.0 | 0.25 | 5.7 | 0.25 | 3.2 | 0.25 | 7.4 | 0.25 | 4.9 |
| 0.3 | 3.0 | 0.3 | 5.7 | 0.3 | 3.2 | 0.3 | 7.4 | 0.3 | 4.9 |
| 0.35 | 3.0 | 0.35 | 5.7 | 0.35 | 3.2 | 0.35 | 7.4 | 0.35 | 4.9 |
| 0.4 | 3.0 | 0.4 | 5.7 | 0.4 | 3.2 | 0.4 | 7.4 | 0.4 | 4.9 |
| 0.45 | 3.0 | 0.45 | 5.7 | 0.45 | 3.2 | 0.45 | 7.4 | 0.45 | 4.9 |
| 0.5 | 3.0 | 0.5 | 5.7 | 0.5 | 3.2 | 0.5 | 7.4 | 0.5 | 4.9 |
| 0.55 | 3.0 | 0.55 | 5.6 | 0.55 | 3.2 | 0.55 | 7.4 | 0.55 | 4.9 |
| 0.6 | 3.0 | 0.6 | 5.6 | 0.6 | 3.2 | 0.6 | 7.4 | 0.6 | 4.8 |
| 0.65 | 3.0 | 0.65 | 5.5 | 0.65 | 3.2 | 0.65 | 7.4 | 0.65 | 4.8 |
| 0.7 | 3.0 | 0.7 | 5.3 | 0.7 | 3.2 | 0.7 | 7.4 | 0.7 | 4.8 |
| 0.75 | 2.9 | 0.75 | 5.1 | 0.75 | 3.1 | 0.75 | 7.2 | 0.75 | 4.6 |
| 0.8 | 2.8 | 0.8 | 4.7 | 0.8 | 3.0 | 0.8 | 6.9 | 0.8 | 4.4 |
| 0.85 | 2.6 | 0.85 | 4.3 | 0.85 | 2.8 | 0.85 | 6.3 | 0.85 | 4.0 |
| 0.9 | 2.3 | 0.9 | 3.6 | 0.9 | 2.4 | 0.9 | 5.3 | 0.9 | 3.4 |
| 0.95 | 1.8 | 0.95 | 2.6 | 0.95 | 1.9 | 0.95 | 3.7 | 0.95 | 2.5 |
| 1 | 1.2 | 1 | 1.2 | 1 | 1.2 | 1 | 1.2 | 1 | 1.2 |

HF - HCFO-1233xf - HFO-1234yf - HFO-1234zeE - HFO-1243zf

| Organics 0.9 F1233xf + 0.033 F1234zeE + 0.033 F1243zf + 0.034 F1234yf | | Organics 0.033 F1233xf + 0.9 F1234zeE + 0.033 F1243zf + 0.034 F1234yf | | Organics 0.033 F1233xf + 0.033 F1234zeE + 0.9 F1243zf + 0.034 F1234yf | | Organics 0.034 F1233xf + 0.033 F1234zeE + 0.033 F1243zf + 0.9 F1234yf | | Organics 0.25 F1233xf + 0.25 F1234zeE + 0.25 F1243zf + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.9 | 0 | 5.7 | 0 | 6.5 | 0 | 4.9 |
| 0.05 | 3.2 | 0.05 | 5.8 | 0.05 | 6.7 | 0.05 | 7.5 | 0.05 | 5.9 |
| 0.1 | 3.2 | 0.1 | 5.9 | 0.1 | 6.7 | 0.1 | 7.5 | 0.1 | 5.9 |
| 0.15 | 3.2 | 0.15 | 5.9 | 0.15 | 6.7 | 0.15 | 7.5 | 0.15 | 5.9 |
| 0.2 | 3.2 | 0.2 | 5.9 | 0.2 | 6.7 | 0.2 | 7.5 | 0.2 | 5.9 |
| 0.25 | 3.2 | 0.25 | 5.9 | 0.25 | 6.7 | 0.25 | 7.5 | 0.25 | 5.9 |
| 0.3 | 3.2 | 0.3 | 5.9 | 0.3 | 6.7 | 0.3 | 7.5 | 0.3 | 5.9 |
| 0.35 | 3.2 | 0.35 | 5.9 | 0.35 | 6.7 | 0.35 | 7.5 | 0.35 | 5.9 |
| 0.4 | 3.1 | 0.4 | 5.8 | 0.4 | 6.7 | 0.4 | 7.5 | 0.4 | 5.9 |
| 0.45 | 3.1 | 0.45 | 5.8 | 0.45 | 6.7 | 0.45 | 7.5 | 0.45 | 5.9 |
| 0.5 | 3.1 | 0.5 | 5.8 | 0.5 | 6.7 | 0.5 | 7.5 | 0.5 | 5.9 |
| 0.55 | 3.1 | 0.55 | 5.8 | 0.55 | 6.7 | 0.55 | 7.5 | 0.55 | 5.9 |
| 0.6 | 3.1 | 0.6 | 5.7 | 0.6 | 6.6 | 0.6 | 7.5 | 0.6 | 5.9 |
| 0.65 | 3.1 | 0.65 | 5.6 | 0.65 | 6.6 | 0.65 | 7.5 | 0.65 | 5.8 |
| 0.7 | 3.1 | 0.7 | 5.4 | 0.7 | 6.5 | 0.7 | 7.5 | 0.7 | 5.7 |
| 0.75 | 3.1 | 0.75 | 5.2 | 0.75 | 6.3 | 0.75 | 7.3 | 0.75 | 5.6 |
| 0.8 | 2.9 | 0.8 | 4.9 | 0.8 | 6.0 | 0.8 | 7.0 | 0.8 | 5.3 |
| 0.85 | 2.7 | 0.85 | 4.4 | 0.85 | 5.5 | 0.85 | 6.4 | 0.85 | 4.8 |
| 0.9 | 2.4 | 0.9 | 3.6 | 0.9 | 4.7 | 0.9 | 5.4 | 0.9 | 4.0 |
| 0.95 | 1.9 | 0.95 | 2.6 | 0.95 | 3.3 | 0.95 | 3.7 | 0.95 | 2.9 |
| 1 | 1.2 | 1 | 1.2 | 1 | 1.2 | 1 | 1.2 | 1 | 1.2 |

HF - HCFO-1233xf- HFO-1234yf- HFO-1234zeE - HCFO-1233zdE

| Organics 0.9 F1233xf + 0.033 F1234zeE + 0.033 F1233zdE + 0.034 F1234yf | | Organics 0.033 F1233xf + 0.9 F1234zeE + 0.033 F1233zdE + 0.034 F1234yf | | Organics 0.033 F1233xf + 0.033 F1234zeE + 0.9 F1233zdE + 0.034 F1234yf | | Organics 0.034 F1233xf + 0.033 F1234zeE + 0.033 F1233zdE + 0.9 F1234yf | | Organics 0.25 F1233xf + 0.25 F1234zeE + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 7.4 | 0.05 | 4.8 |
| 0.1 | 3.0 | 0.1 | 5.7 | 0.1 | 2.8 | 0.1 | 7.4 | 0.1 | 4.8 |
| 0.15 | 3.0 | 0.15 | 5.7 | 0.15 | 2.8 | 0.15 | 7.4 | 0.15 | 4.8 |
| 0.2 | 3.0 | 0.2 | 5.7 | 0.2 | 2.8 | 0.2 | 7.4 | 0.2 | 4.8 |
| 0.25 | 3.0 | 0.25 | 5.7 | 0.25 | 2.8 | 0.25 | 7.4 | 0.25 | 4.8 |
| 0.3 | 3.0 | 0.3 | 5.7 | 0.3 | 2.8 | 0.3 | 7.4 | 0.3 | 4.8 |
| 0.35 | 3.0 | 0.35 | 5.7 | 0.35 | 2.8 | 0.35 | 7.4 | 0.35 | 4.8 |
| 0.4 | 3.0 | 0.4 | 5.7 | 0.4 | 2.8 | 0.4 | 7.4 | 0.4 | 4.8 |
| 0.45 | 3.0 | 0.45 | 5.7 | 0.45 | 2.8 | 0.45 | 7.4 | 0.45 | 4.8 |
| 0.5 | 3.0 | 0.5 | 5.7 | 0.5 | 2.8 | 0.5 | 7.4 | 0.5 | 4.8 |
| 0.55 | 3.0 | 0.55 | 5.6 | 0.55 | 2.8 | 0.55 | 7.4 | 0.55 | 4.8 |
| 0.6 | 3.0 | 0.6 | 5.5 | 0.6 | 2.8 | 0.6 | 7.4 | 0.6 | 4.8 |
| 0.65 | 2.9 | 0.65 | 5.4 | 0.65 | 2.7 | 0.65 | 7.4 | 0.65 | 4.8 |
| 0.7 | 2.9 | 0.7 | 5.3 | 0.7 | 2.7 | 0.7 | 7.4 | 0.7 | 4.7 |
| 0.75 | 2.9 | 0.75 | 5.1 | 0.75 | 2.7 | 0.75 | 7.2 | 0.75 | 4.6 |
| 0.8 | 2.8 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

HF- HCFO-1233xf- HFO-1234yf- HFO-1234zeZ- HFO-1243zf

| Organics 0.9 F1233xf + 0.033 F1234zeZ + 0.033 F1243zf + 0.034 F1234yf | | Organics 0.033 F1233xf + 0.9 F1234zeZ + 0.033 F1243zf + 0.034 F1234yf | | Organics 0.033 F1233xf + 0.033 F1234zeZ + 0.9 F1243zf + 0.034 F1234yf | | Organics 0.034 F1233xf + 0.033 F1234zeZ + 0.033 F1243zf + 0.9 F1234yf | | Organics 0.25 F1233xf + 0.25 F1234zeZ + 0.25 F1243zf + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 5.6 | 0 | 6.4 | 0 | 4.1 |
| 0.05 | 3.1 | 0.05 | 3.2 | 0.05 | 6.6 | 0.05 | 7.4 | 0.05 | 5.2 |
| 0.1 | 3.1 | 0.1 | 3.2 | 0.1 | 6.6 | 0.1 | 7.4 | 0.1 | 5.2 |
| 0.15 | 3.1 | 0.15 | 3.2 | 0.15 | 6.6 | 0.15 | 7.4 | 0.15 | 5.2 |
| 0.2 | 3.1 | 0.2 | 3.2 | 0.2 | 6.6 | 0.2 | 7.4 | 0.2 | 5.2 |
| 0.25 | 3.1 | 0.25 | 3.2 | 0.25 | 6.6 | 0.25 | 7.4 | 0.25 | 5.2 |
| 0.3 | 3.1 | 0.3 | 3.2 | 0.3 | 6.6 | 0.3 | 7.4 | 0.3 | 5.2 |
| 0.35 | 3.0 | 0.35 | 3.2 | 0.35 | 6.6 | 0.35 | 7.4 | 0.35 | 5.2 |
| 0.4 | 3.0 | 0.4 | 3.2 | 0.4 | 6.6 | 0.4 | 7.4 | 0.4 | 5.2 |
| 0.45 | 3.0 | 0.45 | 3.2 | 0.45 | 6.6 | 0.45 | 7.4 | 0.45 | 5.2 |
| 0.5 | 3.0 | 0.5 | 3.2 | 0.5 | 6.6 | 0.5 | 7.4 | 0.5 | 5.2 |
| 0.55 | 3.0 | 0.55 | 3.2 | 0.55 | 6.6 | 0.55 | 7.4 | 0.55 | 5.2 |
| 0.6 | 3.0 | 0.6 | 3.2 | 0.6 | 6.5 | 0.6 | 7.4 | 0.6 | 5.2 |
| 0.65 | 3.0 | 0.65 | 3.2 | 0.65 | 6.5 | 0.65 | 7.4 | 0.65 | 5.2 |
| 0.7 | 3.0 | 0.7 | 3.2 | 0.7 | 6.4 | 0.7 | 7.4 | 0.7 | 5.1 |
| 0.75 | 3.0 | 0.75 | 3.2 | 0.75 | 6.2 | 0.75 | 7.2 | 0.75 | 5.0 |
| 0.8 | 2.9 | 0.8 | 3.1 | 0.8 | 6.0 | 0.8 | 6.9 | 0.8 | 4.8 |
| 0.85 | 2.6 | 0.85 | 2.8 | 0.85 | 5.5 | 0.85 | 6.3 | 0.85 | 4.4 |
| 0.9 | 2.3 | 0.9 | 2.5 | 0.9 | 4.6 | 0.9 | 5.3 | 0.9 | 3.7 |
| 0.95 | 1.8 | 0.95 | 2.0 | 0.95 | 3.3 | 0.95 | 3.7 | 0.95 | 2.7 |
| 1 | 1.2 | 1 | 1.2 | 1 | 1.2 | 1 | 1.2 | 1 | 1.2 |

HF - HCFO-1233xf - HFO-1234yf - HFO-1234zeZ - HCFO-1233zdE

| Organics 0.9 F1233xf + 0.033 F1234zeZ + 0.033 F1233zdE + 0.034 F1234yf | | Organics 0.033 F1233xf + 0.9 F1234zeZ + 0.033 F1233zdE + 0.034 F1234yf | | Organics 0.033 F1233xf + 0.033 F1234zeZ + 0.9 F1233zdE + 0.034 F1234yf | | Organics 0.034 F1233xf + 0.033 F1234zeZ + 0.033 F1233zdE + 0.9 F1234yf | | Organics 0.25 F1233xf + 0.25 F1234zeZ + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |

-continued

| MASSFRAC | PRESSURE | MASSFRAC | PRESSURE | MASSFRAC | PRESSURE | MASSFRAC | PRESSURE | MASSFRAC | PRESSURE |
|---|---|---|---|---|---|---|---|---|---|
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.8 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

HF-HCFO-1233xf-HFO-1234yf-HCFO-1233zdE-HFO-1243zf

| Organics 0.9 F1233xf + 0.033 F1243zf + 0.033 F1233zdE + 0.034 F1234yf | | Organics 0.033 F1233xf + 0.9 F1243zf + 0.033 F1233zdE + 0.034 F1234yf | | Organics 0.033 F1233xf + 0.033 F1243zf + 0.9 F1233zdE + 0.034 F1234yf | | Organics 0.034 F1233xf + 0.033 F1243zf + 0.033 F1233zdE + 0.9 F1234yf | | Organics 0.25 F1233xf + 0.25 F1243zf + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 5.6 | 0 | 1.7 | 0 | 6.4 | 0 | 4.1 |
| 0.05 | 3.0 | 0.05 | 6.6 | 0.05 | 2.8 | 0.05 | 7.4 | 0.05 | 5.2 |
| 0.1 | 3.0 | 0.1 | 6.6 | 0.1 | 2.8 | 0.1 | 7.4 | 0.1 | 5.2 |
| 0.15 | 3.0 | 0.15 | 6.6 | 0.15 | 2.8 | 0.15 | 7.4 | 0.15 | 5.2 |
| 0.2 | 3.0 | 0.2 | 6.6 | 0.2 | 2.8 | 0.2 | 7.4 | 0.2 | 5.2 |
| 0.25 | 3.0 | 0.25 | 6.6 | 0.25 | 2.8 | 0.25 | 7.4 | 0.25 | 5.2 |
| 0.3 | 3.0 | 0.3 | 6.6 | 0.3 | 2.8 | 0.3 | 7.4 | 0.3 | 5.2 |
| 0.35 | 3.0 | 0.35 | 6.6 | 0.35 | 2.8 | 0.35 | 7.4 | 0.35 | 5.2 |
| 0.4 | 3.0 | 0.4 | 6.6 | 0.4 | 2.8 | 0.4 | 7.4 | 0.4 | 5.2 |
| 0.45 | 3.0 | 0.45 | 6.6 | 0.45 | 2.8 | 0.45 | 7.4 | 0.45 | 5.2 |
| 0.5 | 3.0 | 0.5 | 6.6 | 0.5 | 2.8 | 0.5 | 7.4 | 0.5 | 5.1 |
| 0.55 | 3.0 | 0.55 | 6.6 | 0.55 | 2.8 | 0.55 | 7.4 | 0.55 | 5.1 |
| 0.6 | 3.0 | 0.6 | 6.5 | 0.6 | 2.8 | 0.6 | 7.4 | 0.6 | 5.1 |
| 0.65 | 3.0 | 0.65 | 6.5 | 0.65 | 2.8 | 0.65 | 7.4 | 0.65 | 5.1 |
| 0.7 | 3.0 | 0.7 | 6.4 | 0.7 | 2.8 | 0.7 | 7.4 | 0.7 | 5.1 |
| 0.75 | 3.0 | 0.75 | 6.2 | 0.75 | 2.8 | 0.75 | 7.2 | 0.75 | 4.9 |
| 0.8 | 2.8 | 0.8 | 6.0 | 0.8 | 2.7 | 0.8 | 6.9 | 0.8 | 4.7 |
| 0.85 | 2.6 | 0.85 | 5.5 | 0.85 | 2.5 | 0.85 | 6.3 | 0.85 | 4.3 |
| 0.9 | 2.3 | 0.9 | 4.6 | 0.9 | 2.2 | 0.9 | 5.3 | 0.9 | 3.7 |
| 0.95 | 1.8 | 0.95 | 3.3 | 0.95 | 1.8 | 0.95 | 3.7 | 0.95 | 2.7 |
| 1 | 1.2 | 1 | 1.2 | 1 | 1.2 | 1 | 1.2 | 1 | 1.2 |

HF - HCFO-1233xf - HFC-245cb - HFO-1234zeE - HFO-1234yf

| Organics 0.9 F1233xf + 0.033 F1234zeE + 0.033 F245cb + 0.034 F1234yf | | Organics 0.033 F1233xf + 0.9 F1234zeE + 0.033 F245cb + 0.034 F1234yf | | Organics 0.033 F1233xf + 0.033 F1234zeE + 0.9 F245cb + 0.034 F1234yf | | Organics 0.034 F1233xf + 0.033 F1234zeE + 0.033 F245cb + 0.9 F1234yf | | Organics 0.25 F1233xf + 0.25 F1234zeE + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 6.5 | 0 | 4.6 |
| 0.05 | 3.1 | 0.05 | 5.8 | 0.05 | 5.8 | 0.05 | 7.5 | 0.05 | 5.6 |
| 0.1 | 3.1 | 0.1 | 5.8 | 0.1 | 5.8 | 0.1 | 7.5 | 0.1 | 5.6 |
| 0.15 | 3.1 | 0.15 | 5.8 | 0.15 | 5.8 | 0.15 | 7.5 | 0.15 | 5.6 |
| 0.2 | 3.1 | 0.2 | 5.8 | 0.2 | 5.8 | 0.2 | 7.5 | 0.2 | 5.6 |
| 0.25 | 3.1 | 0.25 | 5.8 | 0.25 | 5.8 | 0.25 | 7.5 | 0.25 | 5.6 |
| 0.3 | 3.1 | 0.3 | 5.8 | 0.3 | 5.8 | 0.3 | 7.5 | 0.3 | 5.6 |
| 0.35 | 3.1 | 0.35 | 5.8 | 0.35 | 5.8 | 0.35 | 7.5 | 0.35 | 5.6 |
| 0.4 | 3.1 | 0.4 | 5.8 | 0.4 | 5.8 | 0.4 | 7.5 | 0.4 | 5.6 |
| 0.45 | 3.1 | 0.45 | 5.8 | 0.45 | 5.8 | 0.45 | 7.5 | 0.45 | 5.6 |
| 0.5 | 3.1 | 0.5 | 5.8 | 0.5 | 5.8 | 0.5 | 7.5 | 0.5 | 5.6 |
| 0.55 | 3.1 | 0.55 | 5.7 | 0.55 | 5.8 | 0.55 | 7.5 | 0.55 | 5.6 |
| 0.6 | 3.1 | 0.6 | 5.7 | 0.6 | 5.8 | 0.6 | 7.5 | 0.6 | 5.6 |
| 0.65 | 3.1 | 0.65 | 5.6 | 0.65 | 5.8 | 0.65 | 7.5 | 0.65 | 5.7 |
| 0.7 | 3.1 | 0.7 | 5.4 | 0.7 | 5.8 | 0.7 | 7.5 | 0.7 | 5.7 |

-continued

| MASSFRAC | TOTAL PRESSURE bar | MASSFRAC | TOTAL PRESSURE bar | MASSFRAC | TOTAL PRESSURE bar | MASSFRAC | TOTAL PRESSURE bar | MASSFRAC | TOTAL PRESSURE bar |
|---|---|---|---|---|---|---|---|---|---|
| 0.75 | 3.1 | 0.75 | 5.2 | 0.75 | 5.8 | 0.75 | 7.3 | 0.75 | 5.5 |
| 0.8 | 2.9 | 0.8 | 4.9 | 0.8 | 5.8 | 0.8 | 7.0 | 0.8 | 5.3 |
| 0.85 | 2.7 | 0.85 | 4.4 | 0.85 | 5.7 | 0.85 | 6.4 | 0.85 | 4.8 |
| 0.9 | 2.4 | 0.9 | 3.7 | 0.9 | 4.9 | 0.9 | 5.4 | 0.9 | 4.1 |
| 0.95 | 1.9 | 0.95 | 2.6 | 0.95 | 3.5 | 0.95 | 3.7 | 0.95 | 2.9 |
| 1 | 1.2 | 1 | 1.2 | 1 | 1.2 | 1 | 1.2 | 1 | 1.2 |

HF - HCFO-1233xf - HFC-245cb - HCFO-1233zdE - HFO-1234yf

| Organics 0.9 F1233xf + 0.033 F1233zdE + 0.033 F245cb + 0.034 F1234yf | | Organics 0.033 F1233xf + 0.9 F1233zdE + 0.033 F245cb + 0.034 F1234yf | | Organics 0.033 F1233xf + 0.033 F1233zdE + 0.9 F245cb + 0.034 F1234yf | | Organics 0.034 F1233xf + 0.033 F1233zdE + 0.033 F245cb + 0.9 F1234yf | | Organics 0.25 F1233xf + 0.25 F1233zdE + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 1.7 | 0 | 4.5 | 0 | 6.4 | 0 | 3.7 |
| 0.05 | 3.0 | 0.05 | 2.8 | 0.05 | 5.7 | 0.05 | 7.4 | 0.05 | 4.8 |
| 0.1 | 3.0 | 0.1 | 2.8 | 0.1 | 5.7 | 0.1 | 7.4 | 0.1 | 4.8 |
| 0.15 | 3.0 | 0.15 | 2.8 | 0.15 | 5.7 | 0.15 | 7.4 | 0.15 | 4.8 |
| 0.2 | 3.0 | 0.2 | 2.8 | 0.2 | 5.7 | 0.2 | 7.4 | 0.2 | 4.8 |
| 0.25 | 3.0 | 0.25 | 2.8 | 0.25 | 5.7 | 0.25 | 7.4 | 0.25 | 4.8 |
| 0.3 | 3.0 | 0.3 | 2.8 | 0.3 | 5.7 | 0.3 | 7.4 | 0.3 | 4.8 |
| 0.35 | 3.0 | 0.35 | 2.8 | 0.35 | 5.7 | 0.35 | 7.4 | 0.35 | 4.8 |
| 0.4 | 3.0 | 0.4 | 2.8 | 0.4 | 5.7 | 0.4 | 7.4 | 0.4 | 4.8 |
| 0.45 | 3.0 | 0.45 | 2.8 | 0.45 | 5.7 | 0.45 | 7.4 | 0.45 | 4.8 |
| 0.5 | 3.0 | 0.5 | 2.8 | 0.5 | 5.7 | 0.5 | 7.4 | 0.5 | 4.8 |
| 0.55 | 3.0 | 0.55 | 2.8 | 0.55 | 5.7 | 0.55 | 7.4 | 0.55 | 4.8 |
| 0.6 | 3.0 | 0.6 | 2.8 | 0.6 | 5.7 | 0.6 | 7.4 | 0.6 | 4.8 |
| 0.65 | 3.0 | 0.65 | 2.8 | 0.65 | 5.7 | 0.65 | 7.4 | 0.65 | 4.9 |
| 0.7 | 3.0 | 0.7 | 2.8 | 0.7 | 5.7 | 0.7 | 7.4 | 0.7 | 4.9 |
| 0.75 | 3.0 | 0.75 | 2.8 | 0.75 | 5.7 | 0.75 | 7.2 | 0.75 | 4.9 |
| 0.8 | 2.8 | 0.8 | 2.7 | 0.8 | 5.7 | 0.8 | 6.9 | 0.8 | 4.7 |
| 0.85 | 2.6 | 0.85 | 2.5 | 0.85 | 5.7 | 0.85 | 6.4 | 0.85 | 4.3 |
| 0.9 | 2.3 | 0.9 | 2.2 | 0.9 | 4.9 | 0.9 | 5.4 | 0.9 | 3.7 |
| 0.95 | 1.8 | 0.95 | 1.8 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

HF- HCFO-1233xf- HFC-245cb - HFO-1234zeZ- HFO-1234yf

| Organics 0.9 F1233xf + 0.033 F1234zeZ + 0.033 F245cb + 0.034 F1234yf | | Organics 0.033 F1233xf + 0.9 F1234zeZ + 0.033 F245cb + 0.034 F1234yf | | Organics 0.033 F1233xf + 0.033 F1234zeZ + 0.9 F245cb + 0.034 F1234yf | | Organics 0.034 F1233xf + 0.033 F1234zeZ + 0.033 F245cb + 0.9 F1234yf | | Organics 0.25 F1233xf + 0.25 F1234zeZ + 0.25 F245cb + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 6.4 | 0 | 3.7 |
| 0.05 | 3.0 | 0.05 | 3.2 | 0.05 | 5.7 | 0.05 | 7.4 | 0.05 | 4.9 |
| 0.1 | 3.0 | 0.1 | 3.2 | 0.1 | 5.7 | 0.1 | 7.4 | 0.1 | 4.9 |
| 0.15 | 3.0 | 0.15 | 3.2 | 0.15 | 5.7 | 0.15 | 7.4 | 0.15 | 4.9 |
| 0.2 | 3.0 | 0.2 | 3.2 | 0.2 | 5.7 | 0.2 | 7.4 | 0.2 | 4.9 |
| 0.25 | 3.0 | 0.25 | 3.2 | 0.25 | 5.7 | 0.25 | 7.4 | 0.25 | 4.9 |
| 0.3 | 3.0 | 0.3 | 3.2 | 0.3 | 5.7 | 0.3 | 7.4 | 0.3 | 4.9 |
| 0.35 | 3.0 | 0.35 | 3.2 | 0.35 | 5.7 | 0.35 | 7.4 | 0.35 | 4.9 |
| 0.4 | 3.0 | 0.4 | 3.2 | 0.4 | 5.7 | 0.4 | 7.4 | 0.4 | 4.9 |
| 0.45 | 3.0 | 0.45 | 3.2 | 0.45 | 5.7 | 0.45 | 7.4 | 0.45 | 4.9 |
| 0.5 | 3.0 | 0.5 | 3.2 | 0.5 | 5.7 | 0.5 | 7.4 | 0.5 | 4.9 |
| 0.55 | 3.0 | 0.55 | 3.2 | 0.55 | 5.7 | 0.55 | 7.4 | 0.55 | 4.9 |
| 0.6 | 3.0 | 0.6 | 3.2 | 0.6 | 5.7 | 0.6 | 7.4 | 0.6 | 4.9 |
| 0.65 | 3.0 | 0.65 | 3.2 | 0.65 | 5.7 | 0.65 | 7.4 | 0.65 | 4.9 |
| 0.7 | 3.0 | 0.7 | 3.2 | 0.7 | 5.7 | 0.7 | 7.4 | 0.7 | 4.9 |
| 0.75 | 3.0 | 0.75 | 3.2 | 0.75 | 5.7 | 0.75 | 7.2 | 0.75 | 5.0 |
| 0.8 | 2.8 | 0.8 | 3.0 | 0.8 | 5.7 | 0.8 | 6.9 | 0.8 | 4.8 |
| 0.85 | 2.6 | 0.85 | 2.8 | 0.85 | 5.7 | 0.85 | 6.4 | 0.85 | 4.4 |
| 0.9 | 2.3 | 0.9 | 2.5 | 0.9 | 4.9 | 0.9 | 5.4 | 0.9 | 3.8 |
| 0.95 | 1.8 | 0.95 | 2.0 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

Example 8: Temperature and Pressure Range of Penternary Mixtures

|  | Boiling point range | |
|---|---|---|
| System with 5 compounds | Temperature ° C. | Pressure bar abs |
| HF-HCFO-1233xf-HFC-245cb-HCFO-1233zdE-HFO-1234zeE | 0 to 40 | ⁻1.0⁻8.9 |
| HF-HCFO-1233xf-HFC-245cb-HCFO-1233zdE-HFO-1234zeZ | 0 to 40 | ⁻1.0 to ⁻8.8 |
| HF-HCFO-1233xf-HFC-245cb-HCFO-1233zdE-HFO-1243zf | 0 to 40 | ⁻1.0 to ⁻10.0 |
| HF-HCFO-1233xf-HFC-245cb-HCFO-1233zdE-HFO-1234yf | 0 to 40 | ⁻1.0 to ⁻11.2 |
| HF-HCFO-1233xf-HFC-245cb-HFO-1234zeE-HFO-1234zeZ | 0 to 40 | ⁻1.1 to ⁻8.8 |
| HF-HCFO-1233xf-HFC-245cb-HFO-1234zeE-HFO-1243zf | 0 to 40 | ⁻1.0 to ⁻10.2 |
| HF-HCFO-1233xf-HFC-245cb-HFO-1234zeE-HFO-1234yf | 0 to 40 | ⁻1.0 to ⁻11.4 |
| HF-HCFO-1233xf-HFC-245cb-HFO-1234zeZ-HFO-1243zf | 0 to 40 | ⁻1.1 to ⁻10.1 |
| HF-HCFO-1233xf-HFC-245cb-HFO-1234zeZ-HFO-1234yf | 0 to 40 | ⁻1.1 to ⁻11.2 |
| HF-HCFO-1233xf-HFC-245cb-HFO-1234yf-HFO-1243zf | 0 to 40 | ⁻1.2 to ⁻11.4 |
| HF-HCFO-1233xf-HFO-1234yf-HFO-1234zeE-HFO-1234zeZ | 0 to 40 | ⁻1.1 to ⁻11.2 |
| HF-HCFO-1233xf-HFO-1234yf-HFO-1234zeE-HFO-1243zf | 0 to 40 | ⁻1.2 to ⁻11.4 |
| HF-HCFO-1233xf-HFO-1234yf-HFO-1234zeE-HCFO-1233zdE | 0 to 40 | ⁻1.0 to ⁻11.2 |
| HF-HCFO-1233xf-HFO-1234yf-HFO-1234zeZ-HFO-1243zf | 0 to 40 | ⁻1.2 to ⁻11.2 |
| HF-HCFO-1233xf-HFO-1234yf-HFO-1234zeZ-HCFO-1233zdE | 0 to 40 | ⁻1.0⁻11.1 |
| HF-HCFO-1233xf-HFO-1234yf-HCFO-1233zdE-HFO-1243zf | 0 to 40 | ⁻1.0⁻11.2 |
| HF-HCFO-1233xf-HCFO-1233zdE-HFO-1234zeE-HFO-1234zeZ | 0 to 40 | ⁻0.9 to ⁻8.6 |
| HF-HCFO-1233xf-HCFO-1233zdE-HFO-1234zeE-HFO-1243zf | 0 to 40 | ⁻1.0 to ⁻10.1 |
| HF-HCFO-1233xf-HCFO-1233zdE-HFO-1234zeZ-HFO-1243zf | 0 to 40 | ⁻1.0 to ⁻9.9 |
| HF-HCFO-1233xf-HFO-1234zeE-HFO-1234zeZ-HFO-1243zf | 0 to 40 | ⁻1.0 to ⁻10.1 |

Example 9: Decantation Range of Penternary Mixtures

|  | Decantation ranges Mass percentage of HF | | |
|---|---|---|---|
| System with 5 compounds | Isotherm 0° C. | Isotherm 25° C. | Isotherm 40° C. |
| HF-HCFO-1233xf-HFC-245cb-HCFO-1233zdE-HFO-1234zeE | 5-75 | 5-70 | 10-60 |
| HF-HCFO-1233xf-HFC-245cb-HCFO-1233zdE-HFO-1234zeZ | 5-80 | 5-75 | 5-70 |
| HF-HCFO-1233xf-HFC-245cb-HCFO-1233zdE-HFO-1243zf | 5-75 | 5-70 | 5-65 |
| HF-HCFO-1233xf-HFC-245cb-HCFO-1233zdE-HFO-1234yf | 5-75 | 5-75 | 10-65 |
| HF-HCFO-1233xf-HFC-245cb-HFO-1234zeE-HFO-1234zeZ | 5-75 | 5-70 | 10-60 |
| HF-HCFO-1233xf-HFC-245cb-HFO-1234zeE-HFO-1243zf | 10-75 | 10-65 | * |
| HF-HCFO-1233xf-HFC-245cb-HFO-1234zeE-HFO-1234yf | 5-75 | 10-70 | * |
| HF-HCFO-1233xf-HFC-245cb-HFO-1234zeZ-HFO-1243zf | 5-75 | 5-70 | 10-60 |
| HF-HCFO-1233xf-HFC-245cb-HFO-1234zeZ-HFO-1234yf | 5-75 | 5-75 | 10-65 |
| HF-HCFO-1233xf-HFC-245cb-HFO-1234yf-HFO-1243zf | 5-75 | 10-70 | * |

-continued

|  | Decantation ranges Mass percentage of HF | | |
|---|---|---|---|
| System with 5 compounds | Isotherm 0° C. | Isotherm 25° C. | Isotherm 40° C. |
| HF-HCFO-1233xf-HFO-1234yf-HFO-1234zeE-HFO-1234zeZ | 5-75 | 5-65 | 15-45 |
| HF-HCFO-1233xf-HFO-1234yf-HFO-1234zeE-HFO-1243zf | 5-70 | 10-60 | * |
| HF-HCFO-1233xf-HFO-1234yf-HFO-1234zeE-HCFO-1233zdE | 5-75 | 5-65 | 10-50 |
| HF-HCFO-1233xf-HFO-1234yf-HFO-1234zeZ-HFO-1243zf | 5-75 | 10-65 | 20-40 |
| HF-HCFO-1233xf-HFO-1234yf-HFO-1234zeZ-HCFO-1233zdE | 5-75 | 5-70 | 10-60 |
| HF-HCFO-1233xf-HFO-1234yf-HCFO-1233zdE-HFO-1243zf | 5-75 | 5-65 | 15-45 |
| HF-HCFO-1233xf-HCFO-1233zdE-HFO-1234zeE-HFO-1234zeZ | 5-75 | 5-70 | 5-60 |
| HF-HCFO-1233xf-HCFO-1233zdE-HFO-1234zeE-HFO-1243zf | 5-75 | 5-65 | 15-45 |
| HF-HCFO-1233xf-HCFO-1233zdE-HFO-1234zeZ-HFO-1243zf | 5-75 | 5-70 | 10-60 |
| HF-HCFO-1233xf-HFO-1234zeE-HFO-1234zeZ-HFO-1243zf | 5-75 | 10-65 | 15-40 |

Example 10: Systems with Six Compounds, Isotherm at 25° C.

| HF - HCFO-1233xf - HFO-1234yf - HFC-245cb - HFO-1234zeE- HFO-1234zeZ | | | | | |
|---|---|---|---|---|---|
| Organics 0.2 F1233xf + 0.2 F1234yf + 0.2 F245cb 0.2 F1234zeE + 0.2 F1234zeZ | | Organics 0.96 F1233xf + 0.01 F1234yf + 0.01 F245cb + 0.01 F1234zeE + 0.01 F1234zeZ | | Organics 0.01 F1233xf + 0.96 F1234yf + 0.01 F245cb + 0.01 F1234zeE + 0.01 F1234zeZ | |
| MASSFRAC HF | TOTAL PRESSURE bar | MASSFRAC HF | TOTAL PRESSURE bar | MASSFRAC HF | TOTAL PRESSURE bar |
| 0 | 4.0 | 0 | 1.7 | 0 | 6.7 |
| 0.05 | 5.1 | 0.05 | 2.8 | 0.05 | 7.6 |
| 0.1 | 5.1 | 0.1 | 2.8 | 0.1 | 7.6 |
| 0.15 | 5.1 | 0.15 | 2.8 | 0.15 | 7.6 |
| 0.2 | 5.1 | 0.2 | 2.8 | 0.2 | 7.6 |
| 0.25 | 5.1 | 0.25 | 2.8 | 0.25 | 7.6 |
| 0.3 | 5.1 | 0.3 | 2.8 | 0.3 | 7.6 |
| 0.35 | 5.1 | 0.35 | 2.8 | 0.35 | 7.6 |
| 0.4 | 5.1 | 0.4 | 2.8 | 0.4 | 7.6 |
| 0.45 | 5.1 | 0.45 | 2.8 | 0.45 | 7.6 |
| 0.5 | 5.1 | 0.5 | 2.8 | 0.5 | 7.6 |
| 0.55 | 5.1 | 0.55 | 2.8 | 0.55 | 7.6 |
| 0.6 | 5.1 | 0.6 | 2.8 | 0.6 | 7.6 |
| 0.65 | 5.1 | 0.65 | 2.8 | 0.65 | 7.6 |
| 0.7 | 5.1 | 0.7 | 2.8 | 0.7 | 7.6 |
| 0.75 | 5.0 | 0.75 | 2.8 | 0.75 | 7.5 |
| 0.8 | 4.8 | 0.8 | 2.6 | 0.8 | 7.1 |
| 0.85 | 4.4 | 0.85 | 2.5 | 0.85 | 6.5 |
| 0.9 | 3.7 | 0.9 | 2.2 | 0.9 | 5.5 |
| 0.95 | 2.7 | 0.95 | 1.8 | 0.95 | 3.8 |
| 1 | 1.2 | 1 | 1.2 | 1 | 1.2 |

-continued

| Organics 0.01 F1233xf + 0.01 F1234yf + 0.96 F245cb + 0.01 F1234zeE + 0.01 F1234zeZ | | Organics 0.01 F1233xf + 0.01 F1234yf + 0.01 F245cb + 0.96 F1234zeE + 0.01 F1234zeZ | | Organics 0.01 F1233xf + 0.01 F1234yf + 0.01 F245cb + 0.01 F1234zeE + 0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.9 |
| 0.05 | 5.8 | 0.05 | 5.8 | 0.05 | 3.0 |
| 0.1 | 5.8 | 0.1 | 5.8 | 0.1 | 3.0 |
| 0.15 | 5.8 | 0.15 | 5.8 | 0.15 | 3.0 |
| 0.2 | 5.8 | 0.2 | 5.8 | 0.2 | 3.0 |
| 0.25 | 5.8 | 0.25 | 5.8 | 0.25 | 3.0 |
| 0.3 | 5.8 | 0.3 | 5.8 | 0.3 | 3.0 |
| 0.35 | 5.8 | 0.35 | 5.8 | 0.35 | 3.0 |
| 0.4 | 5.8 | 0.4 | 5.8 | 0.4 | 3.0 |
| 0.45 | 5.8 | 0.45 | 5.8 | 0.45 | 3.0 |
| 0.5 | 5.8 | 0.5 | 5.7 | 0.5 | 3.0 |
| 0.55 | 5.8 | 0.55 | 5.7 | 0.55 | 3.0 |
| 0.6 | 5.8 | 0.6 | 5.6 | 0.6 | 3.0 |
| 0.65 | 5.8 | 0.65 | 5.5 | 0.65 | 3.0 |
| 0.7 | 5.8 | 0.7 | 5.4 | 0.7 | 3.0 |
| 0.75 | 5.8 | 0.75 | 5.1 | 0.75 | 3.0 |
| 0.8 | 5.8 | 0.8 | 4.8 | 0.8 | 2.9 |
| 0.85 | 5.8 | 0.85 | 4.3 | 0.85 | 2.7 |
| 0.9 | 5.0 | 0.9 | 3.6 | 0.9 | 2.4 |
| 0.95 | 3.5 | 0.95 | 2.6 | 0.95 | 1.9 |
| 1 | 1.2 | 1 | 1.2 | 1 | 1.2 |

HF - HCFO-1233xf - HFO-1234yf - HFC-245cb - HFO-1234zeE - HCFO-1233zdE

| Organics 0.2 F1233xf + 0.2 F1234yf + 0.2 F245cb 0.2 F1234zeE + 0.2 F1233zdE | | Organics 0.96 F1233xf + 0.01 F1234yf + 0.01 F245cb + 0.01 F1234zeE + 0.01 F1233zdE | | Organics 0.01 F1233xf + 0.96 F1234yf + 0.01 F245cb + 0.01 F1234zeE + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.9 | 0 | 1.7 | 0 | 6.7 |
| 0.05 | 5.0 | 0.05 | 2.8 | 0.05 | 7.6 |
| 0.1 | 5.0 | 0.1 | 2.8 | 0.1 | 7.6 |
| 0.15 | 5.0 | 0.15 | 2.8 | 0.15 | 7.6 |
| 0.2 | 5.0 | 0.2 | 2.8 | 0.2 | 7.6 |
| 0.25 | 5.0 | 0.25 | 2.8 | 0.25 | 7.6 |
| 0.3 | 5.0 | 0.3 | 2.8 | 0.3 | 7.6 |
| 0.35 | 5.0 | 0.35 | 2.8 | 0.35 | 7.6 |
| 0.4 | 5.0 | 0.4 | 2.8 | 0.4 | 7.6 |
| 0.45 | 5.0 | 0.45 | 2.8 | 0.45 | 7.6 |
| 0.5 | 5.0 | 0.5 | 2.8 | 0.5 | 7.6 |
| 0.55 | 5.0 | 0.55 | 2.8 | 0.55 | 7.6 |
| 0.6 | 5.0 | 0.6 | 2.8 | 0.6 | 7.6 |
| 0.65 | 5.0 | 0.65 | 2.8 | 0.65 | 7.6 |
| 0.7 | 5.1 | 0.7 | 2.8 | 0.7 | 7.6 |
| 0.75 | 5.0 | 0.75 | 2.8 | 0.75 | 7.5 |
| 0.8 | 4.7 | 0.8 | 2.6 | 0.8 | 7.1 |
| 0.85 | 4.3 | 0.85 | 2.5 | 0.85 | 6.5 |
| 0.9 | 3.7 | 0.9 | 2.2 | 0.9 | 5.5 |
| 0.95 | 2.7 | 0.95 | 1.8 | 0.95 | 3.8 |
| 1 | 1.2 | 1 | 1.2 | 1 | 1.2 |

-continued

| Organics<br>0.01 F1233xf +<br>0.01 F1234yf +<br>0.96 F245cb +<br>0.01 F1234zeE +<br>0.01 F1233zdE | | Organics<br>0.01 F1233xf +<br>0.01 F1234yf +<br>0.01 F245cb +<br>0.96 F1234zeE +<br>0.01 F1233zdE | | Organics<br>0.01 F1233xf +<br>0.01 F1234yf +<br>0.01 F245cb +<br>0.01 F1234zeE +<br>0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.5 |
| 0.05 | 5.8 | 0.05 | 5.8 | 0.05 | 2.6 |
| 0.1 | 5.8 | 0.1 | 5.8 | 0.1 | 2.6 |
| 0.15 | 5.8 | 0.15 | 5.8 | 0.15 | 2.6 |
| 0.2 | 5.8 | 0.2 | 5.8 | 0.2 | 2.6 |
| 0.25 | 5.8 | 0.25 | 5.8 | 0.25 | 2.6 |
| 0.3 | 5.8 | 0.3 | 5.8 | 0.3 | 2.6 |
| 0.35 | 5.8 | 0.35 | 5.8 | 0.35 | 2.6 |
| 0.4 | 5.8 | 0.4 | 5.8 | 0.4 | 2.6 |
| 0.45 | 5.8 | 0.45 | 5.8 | 0.45 | 2.6 |
| 0.5 | 5.8 | 0.5 | 5.7 | 0.5 | 2.6 |
| 0.55 | 5.8 | 0.55 | 5.7 | 0.55 | 2.6 |
| 0.6 | 5.8 | 0.6 | 5.6 | 0.6 | 2.6 |
| 0.65 | 5.8 | 0.65 | 5.5 | 0.65 | 2.6 |
| 0.7 | 5.8 | 0.7 | 5.4 | 0.7 | 2.6 |
| 0.75 | 5.8 | 0.75 | 5.1 | 0.75 | 2.6 |
| 0.8 | 5.8 | 0.8 | 4.8 | 0.8 | 2.4 |
| 0.85 | 5.8 | 0.85 | 4.3 | 0.85 | 2.3 |
| 0.9 | 5.0 | 0.9 | 3.6 | 0.9 | 2.0 |
| 0.95 | 3.5 | 0.95 | 2.6 | 0.95 | 1.7 |
| 1 | 1.2 | 1 | 1.2 | 1 | 1.2 |

HF - HCFO-1233xf - HFO-1234yf- HFC-245cb - HFO-1234zeE- HFO-1243zf

| Organics<br>0.2 F1233xf +<br>0.2 F1234yf +<br>0.2 F245cb<br>0.2 F1234zeE +<br>0.2 F1243zf | | Organics<br>0.96 F1233xf +<br>0.01 F1234yf +<br>0.01 F245cb +<br>0.01 F1234zeE +<br>0.01 F1243zf | | Organics<br>0.01 F1233xf +<br>0.96 F1234yf +<br>0.01 F245cb +<br>0.01 F1234zeE +<br>0.01 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.9 | 0 | 1.7 | 0 | 6.7 |
| 0.05 | 5.9 | 0.05 | 2.8 | 0.05 | 7.7 |
| 0.1 | 5.9 | 0.1 | 2.8 | 0.1 | 7.7 |
| 0.15 | 5.9 | 0.15 | 2.8 | 0.15 | 7.7 |
| 0.2 | 5.9 | 0.2 | 2.8 | 0.2 | 7.7 |
| 0.25 | 5.9 | 0.25 | 2.8 | 0.25 | 7.7 |
| 0.3 | 5.9 | 0.3 | 2.8 | 0.3 | 7.7 |
| 0.35 | 5.9 | 0.35 | 2.8 | 0.35 | 7.7 |
| 0.4 | 5.9 | 0.4 | 2.8 | 0.4 | 7.7 |
| 0.45 | 5.9 | 0.45 | 2.8 | 0.45 | 7.7 |
| 0.5 | 5.9 | 0.5 | 2.8 | 0.5 | 7.7 |
| 0.55 | 5.9 | 0.55 | 2.8 | 0.55 | 7.7 |
| 0.6 | 5.9 | 0.6 | 2.8 | 0.6 | 7.7 |
| 0.65 | 5.9 | 0.65 | 2.8 | 0.65 | 7.7 |
| 0.7 | 5.9 | 0.7 | 2.8 | 0.7 | 7.6 |
| 0.75 | 5.7 | 0.75 | 2.8 | 0.75 | 7.5 |
| 0.8 | 5.5 | 0.8 | 2.7 | 0.8 | 7.2 |
| 0.85 | 5.0 | 0.85 | 2.5 | 0.85 | 6.6 |
| 0.9 | 4.2 | 0.9 | 2.2 | 0.9 | 5.5 |
| 0.95 | 3.0 | 0.95 | 1.8 | 0.95 | 3.8 |
| 1 | 1.2 | 1 | 1.2 | 1 | 1.2 |

-continued

| Organics 0.01 F1233xf + 0.01 F1234yf + 0.96 F245cb + 0.01 F1234zeE + 0.01 F1243zf | | Organics 0.01 F1233xf + 0.01 F1234yf + 0.01 F245cb + 0.96 F1234zeE + 0.01 F1243zf | | Organics 0.01 F1233xf + 0.01 F1234yf + 0.01 F245cb + 0.01 F1234zeE + 0.96 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.7 | 0 | 4.9 | 0 | 5.8 |
| 0.05 | 5.8 | 0.05 | 5.8 | 0.05 | 6.7 |
| 0.1 | 5.8 | 0.1 | 5.9 | 0.1 | 6.8 |
| 0.15 | 5.8 | 0.15 | 5.8 | 0.15 | 6.8 |
| 0.2 | 5.8 | 0.2 | 5.8 | 0.2 | 6.8 |
| 0.25 | 5.8 | 0.25 | 5.8 | 0.25 | 6.8 |
| 0.3 | 5.8 | 0.3 | 5.8 | 0.3 | 6.8 |
| 0.35 | 5.8 | 0.35 | 5.8 | 0.35 | 6.8 |
| 0.4 | 5.8 | 0.4 | 5.8 | 0.4 | 6.8 |
| 0.45 | 5.8 | 0.45 | 5.8 | 0.45 | 6.7 |
| 0.5 | 5.8 | 0.5 | 5.8 | 0.5 | 6.7 |
| 0.55 | 5.8 | 0.55 | 5.7 | 0.55 | 6.7 |
| 0.6 | 5.8 | 0.6 | 5.7 | 0.6 | 6.7 |
| 0.65 | 5.8 | 0.65 | 5.6 | 0.65 | 6.6 |
| 0.7 | 5.8 | 0.7 | 5.4 | 0.7 | 6.5 |
| 0.75 | 5.8 | 0.75 | 5.2 | 0.75 | 6.4 |
| 0.8 | 5.8 | 0.8 | 4.8 | 0.8 | 6.1 |
| 0.85 | 5.8 | 0.85 | 4.3 | 0.85 | 5.6 |
| 0.9 | 5.0 | 0.9 | 3.6 | 0.9 | 4.8 |
| 0.95 | 3.5 | 0.95 | 2.6 | 0.95 | 3.4 |
| 1 | 1.2 | 1 | 1.2 | 1 | 1.2 |

HF - HCFO-1233xf - HFO-1234yf - HFC-245cb - HFO-1234zeZ- HCFO-1233zdE

| Organics 0.2 F1233xf + 0.2 F1234yf + 0.2 F245cb 0.2 F1234zeZ + 0.2 F1233zdE | | Organics 0.96 F1233xf + 0.01 F1234yf + 0.01 F245cb + 0.01 F1234zeZ + 0.01 F1233zdE | | Organics 0.01 F1233xf + 0.96 F1234yf + 0.01 F245cb + 0.01 F1234zeZ + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.3 | 0 | 1.6 | 0 | 6.6 |
| 0.05 | 4.4 | 0.05 | 2.8 | 0.05 | 7.6 |
| 0.1 | 4.4 | 0.1 | 2.8 | 0.1 | 7.6 |
| 0.15 | 4.4 | 0.15 | 2.8 | 0.15 | 7.6 |
| 0.2 | 4.4 | 0.2 | 2.8 | 0.2 | 7.6 |
| 0.25 | 4.4 | 0.25 | 2.8 | 0.25 | 7.6 |
| 0.3 | 4.4 | 0.3 | 2.8 | 0.3 | 7.6 |
| 0.35 | 4.4 | 0.35 | 2.8 | 0.35 | 7.6 |
| 0.4 | 4.4 | 0.4 | 2.8 | 0.4 | 7.6 |
| 0.45 | 4.4 | 0.45 | 2.8 | 0.45 | 7.6 |
| 0.5 | 4.4 | 0.5 | 2.8 | 0.5 | 7.6 |
| 0.55 | 4.4 | 0.55 | 2.8 | 0.55 | 7.6 |
| 0.6 | 4.4 | 0.6 | 2.8 | 0.6 | 7.6 |
| 0.65 | 4.5 | 0.65 | 2.8 | 0.65 | 7.6 |
| 0.7 | 4.5 | 0.7 | 2.8 | 0.7 | 7.6 |
| 0.75 | 4.5 | 0.75 | 2.8 | 0.75 | 7.4 |
| 0.8 | 4.3 | 0.8 | 2.6 | 0.8 | 7.1 |
| 0.85 | 4.0 | 0.85 | 2.4 | 0.85 | 6.5 |
| 0.9 | 3.4 | 0.9 | 2.2 | 0.9 | 5.5 |
| 0.95 | 2.5 | 0.95 | 1.7 | 0.95 | 3.8 |
| 1 | 1.2 | 1 | 1.2 | 1 | 1.2 |

| Organics<br>0.01 F1233xf +<br>0.01 F1234yf +<br>0.96 F245cb +<br>0.01 F1234zeZ +<br>0.01 F1233zdE | | Organics<br>0.01 F1233xf +<br>0.01 F1234yf +<br>0.01 F245cb +<br>0.96 F1234zeZ +<br>0.01 F1233zdE | | Organics<br>0.01 F1233xf +<br>0.01 F1234yf +<br>0.01 F245cb +<br>0.01 F1234zeZ +<br>0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.9 | 0 | 1.4 |
| 0.05 | 5.8 | 0.05 | 3.0 | 0.05 | 2.5 |
| 0.1 | 5.8 | 0.1 | 3.0 | 0.1 | 2.5 |
| 0.15 | 5.8 | 0.15 | 3.0 | 0.15 | 2.5 |
| 0.2 | 5.8 | 0.2 | 3.0 | 0.2 | 2.5 |
| 0.25 | 5.8 | 0.25 | 3.0 | 0.25 | 2.5 |
| 0.3 | 5.8 | 0.3 | 3.0 | 0.3 | 2.5 |
| 0.35 | 5.8 | 0.35 | 3.0 | 0.35 | 2.5 |
| 0.4 | 5.8 | 0.4 | 3.0 | 0.4 | 2.5 |
| 0.45 | 5.8 | 0.45 | 3.0 | 0.45 | 2.5 |
| 0.5 | 5.8 | 0.5 | 3.0 | 0.5 | 2.5 |
| 0.55 | 5.8 | 0.55 | 3.0 | 0.55 | 2.5 |
| 0.6 | 5.8 | 0.6 | 3.0 | 0.6 | 2.5 |
| 0.65 | 5.8 | 0.65 | 3.0 | 0.65 | 2.5 |
| 0.7 | 5.8 | 0.7 | 3.0 | 0.7 | 2.5 |
| 0.75 | 5.8 | 0.75 | 3.0 | 0.75 | 2.5 |
| 0.8 | 5.8 | 0.8 | 2.9 | 0.8 | 2.4 |
| 0.85 | 5.8 | 0.85 | 2.7 | 0.85 | 2.3 |
| 0.9 | 5.0 | 0.9 | 2.3 | 0.9 | 2.0 |
| 0.95 | 3.5 | 0.95 | 1.9 | 0.95 | 1.7 |
| 1 | 1.2 | 1 | 1.2 | 1 | 1.2 |

HF - HCFO-1233xf - HFO-1234yf - HFC-245cb - HFO-1234zeZ- HFO-1243zf

| Organics<br>0.2 F1233xf +<br>0.2 F1234yf +<br>0.2 F245cb<br>0.2 F1234zeZ +<br>0.2 F1243zf | | Organics<br>0.96 F1233xf +<br>0.01 F1234yf +<br>0.01 F245cb +<br>0.01 F1234zeZ +<br>0.01 F1243zf | | Organics<br>0.01 F1233xf +<br>0.96 F1234yf +<br>0.01 F245cb +<br>0.01 F1234zeZ +<br>0.01 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.2 | 0 | 1.7 | 0 | 6.7 |
| 0.05 | 5.3 | 0.05 | 2.8 | 0.05 | 7.6 |
| 0.1 | 5.3 | 0.1 | 2.8 | 0.1 | 7.7 |
| 0.15 | 5.3 | 0.15 | 2.8 | 0.15 | 7.6 |
| 0.2 | 5.3 | 0.2 | 2.8 | 0.2 | 7.6 |
| 0.25 | 5.3 | 0.25 | 2.8 | 0.25 | 7.6 |
| 0.3 | 5.3 | 0.3 | 2.8 | 0.3 | 7.6 |
| 0.35 | 5.3 | 0.35 | 2.8 | 0.35 | 7.6 |
| 0.4 | 5.3 | 0.4 | 2.8 | 0.4 | 7.6 |
| 0.45 | 5.3 | 0.45 | 2.8 | 0.45 | 7.6 |
| 0.5 | 5.3 | 0.5 | 2.8 | 0.5 | 7.6 |
| 0.55 | 5.3 | 0.55 | 2.8 | 0.55 | 7.6 |
| 0.6 | 5.3 | 0.6 | 2.8 | 0.6 | 7.6 |
| 0.65 | 5.3 | 0.65 | 2.8 | 0.65 | 7.6 |
| 0.7 | 5.3 | 0.7 | 2.8 | 0.7 | 7.6 |
| 0.75 | 5.3 | 0.75 | 2.8 | 0.75 | 7.5 |
| 0.8 | 5.1 | 0.8 | 2.7 | 0.8 | 7.2 |
| 0.85 | 4.7 | 0.85 | 2.5 | 0.85 | 6.6 |
| 0.9 | 4.0 | 0.9 | 2.2 | 0.9 | 5.5 |
| 0.95 | 2.9 | 0.95 | 1.8 | 0.95 | 3.8 |
| 1 | 1.2 | 1 | 1.2 | 1 | 1.2 |

-continued

| Organics 0.01 F1233xf + 0.01 F1234yf + 0.96 F245cb + 0.01 F1234zeZ + 0.01 F1243zf | | Organics 0.01 F1233xf + 0.01 F1234yf + 0.01 F245cb + 0.96 F1234zeZ + 0.01 F1243zf | | Organics 0.01 F1233xf + 0.01 F1234yf + 0.01 F245cb + 0.01 F1234zeZ + 0.96 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.9 | 0 | 5.8 |
| 0.05 | 5.8 | 0.05 | 3.0 | 0.05 | 6.7 |
| 0.1 | 5.8 | 0.1 | 3.0 | 0.1 | 6.8 |
| 0.15 | 5.8 | 0.15 | 3.0 | 0.15 | 6.7 |
| 0.2 | 5.8 | 0.2 | 3.0 | 0.2 | 6.7 |
| 0.25 | 5.8 | 0.25 | 3.0 | 0.25 | 6.7 |
| 0.3 | 5.8 | 0.3 | 3.0 | 0.3 | 6.7 |
| 0.35 | 5.8 | 0.35 | 3.0 | 0.35 | 6.7 |
| 0.4 | 5.8 | 0.4 | 3.0 | 0.4 | 6.7 |
| 0.45 | 5.8 | 0.45 | 3.0 | 0.45 | 6.7 |
| 0.5 | 5.8 | 0.5 | 3.0 | 0.5 | 6.7 |
| 0.55 | 5.8 | 0.55 | 3.0 | 0.55 | 6.7 |
| 0.6 | 5.8 | 0.6 | 3.0 | 0.6 | 6.7 |
| 0.65 | 5.8 | 0.65 | 3.0 | 0.65 | 6.6 |
| 0.7 | 5.8 | 0.7 | 3.0 | 0.7 | 6.5 |
| 0.75 | 5.8 | 0.75 | 3.0 | 0.75 | 6.4 |
| 0.8 | 5.8 | 0.8 | 2.9 | 0.8 | 6.1 |
| 0.85 | 5.8 | 0.85 | 2.7 | 0.85 | 5.6 |
| 0.9 | 5.0 | 0.9 | 2.4 | 0.9 | 4.7 |
| 0.95 | 3.5 | 0.95 | 1.9 | 0.95 | 3.4 |
| 1 | 1.2 | 1 | 1.2 | 1 | 1.2 |

HF - HCFO-1233xf - HFO-1234yf - HFC-245cb - HCFO-1233zdE- HFO-1243zf

| Organics 0.2 F1233xf + 0.2 F1234yf + 0.2 F245cb 0.2 F1233zdE + 0.2 F1243zf | | Organics 0.96 F1233xf + 0.01 F1234yf + 0.01 F245cb + 0.01 F1233zdE + 0.01 F1243zf | | Organics 0.01 F1233xf + 0.96 F1234yf 0.01 F245cb + 0.01 F1233zdE + 0.01 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.2 | 0 | 1.7 | 0 | 6.7 |
| 0.05 | 5.3 | 0.05 | 2.8 | 0.05 | 7.6 |
| 0.1 | 5.3 | 0.1 | 2.8 | 0.1 | 7.7 |
| 0.15 | 5.3 | 0.15 | 2.8 | 0.15 | 7.6 |
| 0.2 | 5.3 | 0.2 | 2.8 | 0.2 | 7.6 |
| 0.25 | 5.3 | 0.25 | 2.8 | 0.25 | 7.6 |
| 0.3 | 5.3 | 0.3 | 2.8 | 0.3 | 7.6 |
| 0.35 | 5.3 | 0.35 | 2.8 | 0.35 | 7.6 |
| 0.4 | 5.3 | 0.4 | 2.8 | 0.4 | 7.6 |
| 0.45 | 5.3 | 0.45 | 2.8 | 0.45 | 7.6 |
| 0.5 | 5.3 | 0.5 | 2.8 | 0.5 | 7.6 |
| 0.55 | 5.3 | 0.55 | 2.8 | 0.55 | 7.6 |
| 0.6 | 5.3 | 0.6 | 2.8 | 0.6 | 7.6 |
| 0.65 | 5.3 | 0.65 | 2.8 | 0.65 | 7.6 |
| 0.7 | 5.3 | 0.7 | 2.8 | 0.7 | 7.6 |
| 0.75 | 5.2 | 0.75 | 2.8 | 0.75 | 7.5 |
| 0.8 | 5.0 | 0.8 | 2.7 | 0.8 | 7.2 |
| 0.85 | 4.6 | 0.85 | 2.5 | 0.85 | 6.6 |
| 0.9 | 3.9 | 0.9 | 2.2 | 0.9 | 5.5 |
| 0.95 | 2.8 | 0.95 | 1.8 | 0.95 | 3.8 |
| 1 | 1.2 | 1 | 1.2 | 1 | 1.2 |

-continued

| Organics 0.01 F1233xf + 0.01 F1234yf + 0.96 F245cb + 0.01 F1233zdE + 0.01 F1243zf | | Organics 0.01 F1233xf + 0.01 F1234yf + 0.01 F245cb + 0.96 F1233zdE + 0.01 F1243zf | | Organics 0.01 F1233xf + 0.01 F1234yf + 0.01 F245cb + 0.01 F1233zdE + 0.96 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.5 | 0 | 5.8 |
| 0.05 | 5.8 | 0.05 | 2.6 | 0.05 | 6.7 |
| 0.1 | 5.8 | 0.1 | 2.6 | 0.1 | 6.8 |
| 0.15 | 5.8 | 0.15 | 2.6 | 0.15 | 6.7 |
| 0.2 | 5.8 | 0.2 | 2.6 | 0.2 | 6.7 |
| 0.25 | 5.8 | 0.25 | 2.6 | 0.25 | 6.7 |
| 0.3 | 5.8 | 0.3 | 2.6 | 0.3 | 6.7 |
| 0.35 | 5.8 | 0.35 | 2.6 | 0.35 | 6.7 |
| 0.4 | 5.8 | 0.4 | 2.6 | 0.4 | 6.7 |
| 0.45 | 5.8 | 0.45 | 2.6 | 0.45 | 6.7 |
| 0.5 | 5.8 | 0.5 | 2.6 | 0.5 | 6.7 |
| 0.55 | 5.8 | 0.55 | 2.6 | 0.55 | 6.7 |
| 0.6 | 5.8 | 0.6 | 2.6 | 0.6 | 6.7 |
| 0.65 | 5.8 | 0.65 | 2.6 | 0.65 | 6.6 |
| 0.7 | 5.8 | 0.7 | 2.6 | 0.7 | 6.5 |
| 0.75 | 5.8 | 0.75 | 2.6 | 0.75 | 6.4 |
| 0.8 | 5.8 | 0.8 | 2.5 | 0.8 | 6.1 |
| 0.85 | 5.8 | 0.85 | 2.3 | 0.85 | 5.6 |
| 0.9 | 5.0 | 0.9 | 2.0 | 0.9 | 4.7 |
| 0.95 | 3.5 | 0.95 | 1.7 | 0.95 | 3.4 |
| 1 | 1.2 | 1 | 1.2 | 1 | 1.2 |

HF - HCFO-1233xf - HFO-1234yf - HFO-1234zeE - HFO-1234zeZ - HCFO-1233zdE

| Organics 0.2 F1233xf + 0.2 F1234yf + 0.2 F1233zdE + 0.2 F1234zeE + 0.2 F1234zeZ | | Organics 0.96 F1233xf + 0.01 F1234yf + 0.01 F1233zdE + 0.01 F1234zeE + 0.01 F1234zeZ | | Organics 0.01 F1233xf + 0.96 F1234yf + 0.01 F1233zdE + 0.01 F1234zeE + 0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.4 | 0 | 1.6 | 0 | 6.6 |
| 0.05 | 4.4 | 0.05 | 2.8 | 0.05 | 7.6 |
| 0.1 | 4.4 | 0.1 | 2.8 | 0.1 | 7.6 |
| 0.15 | 4.4 | 0.15 | 2.8 | 0.15 | 7.6 |
| 0.2 | 4.4 | 0.2 | 2.8 | 0.2 | 7.6 |
| 0.25 | 4.4 | 0.25 | 2.8 | 0.25 | 7.6 |
| 0.3 | 4.4 | 0.3 | 2.8 | 0.3 | 7.6 |
| 0.35 | 4.4 | 0.35 | 2.8 | 0.35 | 7.6 |
| 0.4 | 4.4 | 0.4 | 2.8 | 0.4 | 7.6 |
| 0.45 | 4.4 | 0.45 | 2.7 | 0.45 | 7.6 |
| 0.5 | 4.4 | 0.5 | 2.7 | 0.5 | 7.6 |
| 0.55 | 4.4 | 0.55 | 2.7 | 0.55 | 7.6 |
| 0.6 | 4.4 | 0.6 | 2.7 | 0.6 | 7.6 |
| 0.65 | 4.4 | 0.65 | 2.7 | 0.65 | 7.6 |
| 0.7 | 4.4 | 0.7 | 2.7 | 0.7 | 7.6 |
| 0.75 | 4.2 | 0.75 | 2.7 | 0.75 | 7.4 |
| 0.8 | 4.0 | 0.8 | 2.6 | 0.8 | 7.1 |
| 0.85 | 3.6 | 0.85 | 2.4 | 0.85 | 6.5 |
| 0.9 | 3.1 | 0.9 | 2.1 | 0.9 | 5.5 |
| 0.95 | 2.3 | 0.95 | 1.7 | 0.95 | 3.8 |
| 1 | 1.2 | 1 | 1.2 | 1 | 1.2 |

-continued

| Organics 0.01 F1233xf + 0.01 F1234yf + 0.96 F1233zdE + 0.01 F1234zeE + 0.01 F1234zeZ | | Organics 0.01 F1233xf + 0.01 F1234yf + 0.01 F1233zdE + 0.96 F1234zeE + 0.01 F1234zeZ | | Organics 0.01 F1233xf + 0.01 F1234yf + 0.01 F1233zdE + 0.01 F1234zeE + 0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.4 | 0 | 4.8 | 0 | 1.9 |
| 0.05 | 2.5 | 0.05 | 5.8 | 0.05 | 3.0 |
| 0.1 | 2.5 | 0.1 | 5.8 | 0.1 | 3.0 |
| 0.15 | 2.5 | 0.15 | 5.8 | 0.15 | 3.0 |
| 0.2 | 2.5 | 0.2 | 5.8 | 0.2 | 3.0 |
| 0.25 | 2.5 | 0.25 | 5.8 | 0.25 | 3.0 |
| 0.3 | 2.5 | 0.3 | 5.8 | 0.3 | 3.0 |
| 0.35 | 2.5 | 0.35 | 5.8 | 0.35 | 3.0 |
| 0.4 | 2.5 | 0.4 | 5.8 | 0.4 | 3.0 |
| 0.45 | 2.5 | 0.45 | 5.7 | 0.45 | 3.0 |
| 0.5 | 2.5 | 0.5 | 5.7 | 0.5 | 3.0 |
| 0.55 | 2.5 | 0.55 | 5.7 | 0.55 | 3.0 |
| 0.6 | 2.5 | 0.6 | 5.6 | 0.6 | 3.0 |
| 0.65 | 2.5 | 0.65 | 5.5 | 0.65 | 3.0 |
| 0.7 | 2.5 | 0.7 | 5.3 | 0.7 | 3.0 |
| 0.75 | 2.5 | 0.75 | 5.1 | 0.75 | 3.0 |
| 0.8 | 2.4 | 0.8 | 4.8 | 0.8 | 2.8 |
| 0.85 | 2.2 | 0.85 | 4.3 | 0.85 | 2.6 |
| 0.9 | 2.0 | 0.9 | 3.6 | 0.9 | 2.3 |
| 0.95 | 1.7 | 0.95 | 2.6 | 0.95 | 1.9 |
| 1 | 1.2 | 1 | 1.2 | 1 | 1.2 |

HF - HCFO-1233xf - HFO-1234yf - HFO-1234zeE - HFO-1234zeZ - HFO-1243zf

| Organics 0.2 F1233xf + 0.2 F1234yf + 0.2 F1243zf + 0.2 F1234zeE + 0.2 F1234zeZ | | Organics 0.96 F1233xf + 0.01 F1234yf + 0.01 F1243zf + 0.01 F1234zeE + 0.01 F1234zeZ | | Organics 0.01 F1233xf + 0.96 F1234yf + 0.01 F1243zf + 0.01 F1234zeE + 0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 |
| 0.05 | 5.3 | 0.05 | 2.8 | 0.05 | 7.6 |
| 0.1 | 5.3 | 0.1 | 2.8 | 0.1 | 7.6 |
| 0.15 | 5.3 | 0.15 | 2.8 | 0.15 | 7.6 |
| 0.2 | 5.3 | 0.2 | 2.8 | 0.2 | 7.6 |
| 0.25 | 5.3 | 0.25 | 2.8 | 0.25 | 7.6 |
| 0.3 | 5.3 | 0.3 | 2.8 | 0.3 | 7.6 |
| 0.35 | 5.3 | 0.35 | 2.8 | 0.35 | 7.6 |
| 0.4 | 5.3 | 0.4 | 2.8 | 0.4 | 7.6 |
| 0.45 | 5.3 | 0.45 | 2.8 | 0.45 | 7.6 |
| 0.5 | 5.3 | 0.5 | 2.8 | 0.5 | 7.6 |
| 0.55 | 5.3 | 0.55 | 2.8 | 0.55 | 7.6 |
| 0.6 | 5.3 | 0.6 | 2.8 | 0.6 | 7.6 |
| 0.65 | 5.3 | 0.65 | 2.8 | 0.65 | 7.6 |
| 0.7 | 5.2 | 0.7 | 2.8 | 0.7 | 7.6 |
| 0.75 | 5.0 | 0.75 | 2.8 | 0.75 | 7.5 |
| 0.8 | 4.8 | 0.8 | 2.7 | 0.8 | 7.1 |
| 0.85 | 4.3 | 0.85 | 2.5 | 0.85 | 6.5 |
| 0.9 | 3.7 | 0.9 | 2.2 | 0.9 | 5.5 |
| 0.95 | 2.7 | 0.95 | 1.8 | 0.95 | 3.8 |
| 1 | 1.2 | 1 | 1.2 | 1 | 1.2 |

-continued

| Organics<br>0.01 F1233xf +<br>0.01 F1234yf +<br>0.96 F1243zf +<br>0.01 F1234zeE +<br>0.01 F1234zeZ | | Organics<br>0.01 F1233xf +<br>0.01 F1234yf +<br>0.01 F1243zf +<br>0.96 F1234zeE +<br>0.01 F1234zeZ | | Organics<br>0.01 F1233xf +<br>0.01 F1234yf +<br>0.01 F1243zf +<br>0.01 F1234zeE +<br>0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.8 | 0 | 4.8 | 0 | 1.9 |
| 0.05 | 6.7 | 0.05 | 5.8 | 0.05 | 3.0 |
| 0.1 | 6.7 | 0.1 | 5.8 | 0.1 | 3.0 |
| 0.15 | 6.7 | 0.15 | 5.8 | 0.15 | 3.0 |
| 0.2 | 6.7 | 0.2 | 5.8 | 0.2 | 3.0 |
| 0.25 | 6.7 | 0.25 | 5.8 | 0.25 | 3.0 |
| 0.3 | 6.7 | 0.3 | 5.8 | 0.3 | 3.0 |
| 0.35 | 6.7 | 0.35 | 5.8 | 0.35 | 3.0 |
| 0.4 | 6.7 | 0.4 | 5.8 | 0.4 | 3.0 |
| 0.45 | 6.7 | 0.45 | 5.8 | 0.45 | 3.0 |
| 0.5 | 6.7 | 0.5 | 5.8 | 0.5 | 3.0 |
| 0.55 | 6.7 | 0.55 | 5.7 | 0.55 | 3.0 |
| 0.6 | 6.7 | 0.6 | 5.6 | 0.6 | 3.0 |
| 0.65 | 6.6 | 0.65 | 5.5 | 0.65 | 3.0 |
| 0.7 | 6.5 | 0.7 | 5.4 | 0.7 | 3.0 |
| 0.75 | 6.3 | 0.75 | 5.1 | 0.75 | 3.0 |
| 0.8 | 6.1 | 0.8 | 4.8 | 0.8 | 2.9 |
| 0.85 | 5.6 | 0.85 | 4.3 | 0.85 | 2.7 |
| 0.9 | 4.7 | 0.9 | 3.6 | 0.9 | 2.4 |
| 0.95 | 3.4 | 0.95 | 2.6 | 0.95 | 1.9 |
| 1 | 1.2 | 1 | 1.2 | 1 | 1.2 |

HF - HCFO-1233xf - HFO-1234yf - HFO-1234zeE - HCFO-1233zdE - HFO-1243zf

| Organics<br>0.2 F1233xf +<br>0.2 F1234yf +<br>0.2 F1243zf +<br>0.2 F1234zeE +<br>0.2 F1233zdE | | Organics<br>0.96 F1233xf +<br>0.01 F1234yf +<br>0.01 F1243zf +<br>0.01 F1234zeE +<br>0.01 F1233zdE | | Organics<br>0.01 F1233xf +<br>0.96 F1234yf +<br>0.01 F1243zf +<br>0.01 F1234zeE +<br>0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 |
| 0.05 | 5.3 | 0.05 | 2.8 | 0.05 | 7.6 |
| 0.1 | 5.3 | 0.1 | 2.8 | 0.1 | 7.6 |
| 0.15 | 5.3 | 0.15 | 2.8 | 0.15 | 7.6 |
| 0.2 | 5.3 | 0.2 | 2.8 | 0.2 | 7.6 |
| 0.25 | 5.3 | 0.25 | 2.8 | 0.25 | 7.6 |
| 0.3 | 5.3 | 0.3 | 2.8 | 0.3 | 7.6 |
| 0.35 | 5.3 | 0.35 | 2.8 | 0.35 | 7.6 |
| 0.4 | 5.3 | 0.4 | 2.8 | 0.4 | 7.6 |
| 0.45 | 5.3 | 0.45 | 2.8 | 0.45 | 7.6 |
| 0.5 | 5.3 | 0.5 | 2.8 | 0.5 | 7.6 |
| 0.55 | 5.3 | 0.55 | 2.8 | 0.55 | 7.6 |
| 0.6 | 5.3 | 0.6 | 2.8 | 0.6 | 7.6 |
| 0.65 | 5.2 | 0.65 | 2.8 | 0.65 | 7.6 |
| 0.7 | 5.1 | 0.7 | 2.8 | 0.7 | 7.6 |
| 0.75 | 5.0 | 0.75 | 2.8 | 0.75 | 7.5 |
| 0.8 | 4.7 | 0.8 | 2.6 | 0.8 | 7.1 |
| 0.85 | 4.3 | 0.85 | 2.5 | 0.85 | 6.5 |
| 0.9 | 3.6 | 0.9 | 2.2 | 0.9 | 5.5 |
| 0.95 | 2.6 | 0.95 | 1.8 | 0.95 | 3.8 |
| 1 | 1.2 | 1 | 1.2 | 1 | 1.2 |

-continued

| Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.8 | 0 | 4.8 | 0 | 1.5 |
| 0.05 | 6.7 | 0.05 | 5.8 | 0.05 | 2.6 |
| 0.1 | 6.7 | 0.1 | 5.8 | 0.1 | 2.6 |
| 0.15 | 6.7 | 0.15 | 5.8 | 0.15 | 2.6 |
| 0.2 | 6.7 | 0.2 | 5.8 | 0.2 | 2.6 |
| 0.25 | 6.7 | 0.25 | 5.8 | 0.25 | 2.6 |
| 0.3 | 6.7 | 0.3 | 5.8 | 0.3 | 2.6 |
| 0.35 | 6.7 | 0.35 | 5.8 | 0.35 | 2.6 |
| 0.4 | 6.7 | 0.4 | 5.8 | 0.4 | 2.6 |
| 0.45 | 6.7 | 0.45 | 5.8 | 0.45 | 2.6 |
| 0.5 | 6.7 | 0.5 | 5.8 | 0.5 | 2.6 |
| 0.55 | 6.7 | 0.55 | 5.7 | 0.55 | 2.6 |
| 0.6 | 6.7 | 0.6 | 5.6 | 0.6 | 2.6 |
| 0.65 | 6.6 | 0.65 | 5.5 | 0.65 | 2.6 |
| 0.7 | 6.5 | 0.7 | 5.4 | 0.7 | 2.6 |
| 0.75 | 6.3 | 0.75 | 5.1 | 0.75 | 2.6 |
| 0.8 | 6.1 | 0.8 | 4.8 | 0.8 | 2.4 |
| 0.85 | 5.6 | 0.85 | 4.3 | 0.85 | 2.3 |
| 0.9 | 4.7 | 0.9 | 3.6 | 0.9 | 2.0 |
| 0.95 | 3.4 | 0.95 | 2.6 | 0.95 | 1.7 |
| 1 | 1.2 | 1 | 1.2 | 1 | 1.2 |

HF - HCFO-1233xf - HFO-1234yf - HFO-1234zeZ - HCFO-1233zdE - HFO-1243zf

| Organics 0.2 F1233xf + 0.2 F1234yf + 0.2 F1243zf + 0.2 F1234zeZ + 0.2 F1233zdE | | Organics 0.96 F1233xf + 0.01 F1234yf + 0.01 F1243zf + 0.01 F1234zeZ + 0.01 F1233zdE | | Organics 0.01 F1233xf + 0.96 F1234yf + 0.01 F1243zf + 0.01 F1234zeZ + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.6 | 0 | 1.7 | 0 | 6.6 |
| 0.05 | 4.7 | 0.05 | 2.8 | 0.05 | 7.6 |
| 0.1 | 4.7 | 0.1 | 2.8 | 0.1 | 7.6 |
| 0.15 | 4.7 | 0.15 | 2.8 | 0.15 | 7.6 |
| 0.2 | 4.7 | 0.2 | 2.8 | 0.2 | 7.6 |
| 0.25 | 4.7 | 0.25 | 2.8 | 0.25 | 7.6 |
| 0.3 | 4.7 | 0.3 | 2.8 | 0.3 | 7.6 |
| 0.35 | 4.7 | 0.35 | 2.8 | 0.35 | 7.6 |
| 0.4 | 4.7 | 0.4 | 2.8 | 0.4 | 7.6 |
| 0.45 | 4.7 | 0.45 | 2.8 | 0.45 | 7.6 |
| 0.5 | 4.7 | 0.5 | 2.8 | 0.5 | 7.6 |
| 0.55 | 4.7 | 0.55 | 2.8 | 0.55 | 7.6 |
| 0.6 | 4.7 | 0.6 | 2.8 | 0.6 | 7.6 |
| 0.65 | 4.7 | 0.65 | 2.8 | 0.65 | 7.6 |
| 0.7 | 4.7 | 0.7 | 2.8 | 0.7 | 7.6 |
| 0.75 | 4.5 | 0.75 | 2.8 | 0.75 | 7.4 |
| 0.8 | 4.3 | 0.8 | 2.6 | 0.8 | 7.1 |
| 0.85 | 3.9 | 0.85 | 2.4 | 0.85 | 6.5 |
| 0.9 | 3.4 | 0.9 | 2.2 | 0.9 | 5.5 |
| 0.95 | 2.5 | 0.95 | 1.7 | 0.95 | 3.8 |
| 1 | 1.2 | 1 | 1.2 | 1 | 1.2 |

-continued

| Organics 0.01 F1233xf + 0.01 F1234yf + 0.96 F1243zf + 0.01 F1234zeZ + 0.01 F1233zdE | | Organics 0.01 F1233xf + 0.01 F1234yf + 0.01 F1243zf + 0.96 F1234zeZ + 0.01 F1233zdE | | Organics 0.01 F1233xf + 0.01 F1234yf + 0.01 F1243zf + 0.01 F1234zeZ + 0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.7 | 0 | 1.9 | 0 | 1.4 |
| 0.05 | 6.7 | 0.05 | 3.0 | 0.05 | 2.6 |
| 0.1 | 6.7 | 0.1 | 3.0 | 0.1 | 2.6 |
| 0.15 | 6.7 | 0.15 | 3.0 | 0.15 | 2.6 |
| 0.2 | 6.7 | 0.2 | 3.0 | 0.2 | 2.6 |
| 0.25 | 6.7 | 0.25 | 3.0 | 0.25 | 2.6 |
| 0.3 | 6.7 | 0.3 | 3.0 | 0.3 | 2.6 |
| 0.35 | 6.7 | 0.35 | 3.0 | 0.35 | 2.5 |
| 0.4 | 6.7 | 0.4 | 3.0 | 0.4 | 2.5 |
| 0.45 | 6.7 | 0.45 | 3.0 | 0.45 | 2.5 |
| 0.5 | 6.7 | 0.5 | 3.0 | 0.5 | 2.5 |
| 0.55 | 6.7 | 0.55 | 3.0 | 0.55 | 2.5 |
| 0.6 | 6.6 | 0.6 | 3.0 | 0.6 | 2.5 |
| 0.65 | 6.6 | 0.65 | 3.0 | 0.65 | 2.5 |
| 0.7 | 6.5 | 0.7 | 3.0 | 0.7 | 2.5 |
| 0.75 | 6.3 | 0.75 | 3.0 | 0.75 | 2.5 |
| 0.8 | 6.0 | 0.8 | 2.9 | 0.8 | 2.4 |
| 0.85 | 5.5 | 0.85 | 2.7 | 0.85 | 2.3 |
| 0.9 | 4.7 | 0.9 | 2.3 | 0.9 | 2.0 |
| 0.95 | 3.3 | 0.95 | 1.9 | 0.95 | 1.7 |
| 1 | 1.2 | 1 | 1.2 | 1 | 1.2 |

HF - HCFO-1233xf - HFC-245cb - HFO-1234zeE - HFO-1234zeZ - HCFO-1233zdE

| Organics 0.2 F1233xf + 0.2 F245cb + 0.2 F1233zdE + 0.2 F1234zeE + 0.2 F1234zeZ | | Organics 0.96 F1233xf + 0.01 F245cb + 0.01 F1233zdE + 0.01 F1234zeE + 0.01 F1234zeZ | | Organics 0.01 F1233xf + 0.96 F245cb + 0.01 F1233zdE + 0.01 F1234zeE + 0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 2.9 | 0 | 1.6 | 0 | 4.6 |
| 0.05 | 4.0 | 0.05 | 2.7 | 0.05 | 5.7 |
| 0.1 | 4.0 | 0.1 | 2.7 | 0.1 | 5.7 |
| 0.15 | 4.0 | 0.15 | 2.7 | 0.15 | 5.7 |
| 0.2 | 4.0 | 0.2 | 2.7 | 0.2 | 5.7 |
| 0.25 | 4.0 | 0.25 | 2.7 | 0.25 | 5.7 |
| 0.3 | 4.0 | 0.3 | 2.7 | 0.3 | 5.7 |
| 0.35 | 4.0 | 0.35 | 2.7 | 0.35 | 5.7 |
| 0.4 | 4.0 | 0.4 | 2.7 | 0.4 | 5.7 |
| 0.45 | 4.0 | 0.45 | 2.7 | 0.45 | 5.7 |
| 0.5 | 4.0 | 0.5 | 2.7 | 0.5 | 5.7 |
| 0.55 | 4.0 | 0.55 | 2.7 | 0.55 | 5.7 |
| 0.6 | 4.0 | 0.6 | 2.7 | 0.6 | 5.7 |
| 0.65 | 4.0 | 0.65 | 2.7 | 0.65 | 5.7 |
| 0.7 | 4.0 | 0.7 | 2.7 | 0.7 | 5.8 |
| 0.75 | 4.0 | 0.75 | 2.7 | 0.75 | 5.8 |
| 0.8 | 3.8 | 0.8 | 2.6 | 0.8 | 5.8 |
| 0.85 | 3.5 | 0.85 | 2.4 | 0.85 | 5.8 |
| 0.9 | 3.0 | 0.9 | 2.1 | 0.9 | 5.0 |
| 0.95 | 2.3 | 0.95 | 1.7 | 0.95 | 3.5 |
| 1 | 1.2 | 1 | 1.2 | 1 | 1.2 |

-continued

| Organics 0.01 F1233xf + 0.01 F245cb + 0.96 F1233zdE + 0.01 F1234zeE + 0.01 F1234zeZ | | Organics 0.01 F1233xf + 0.01 F245cb + 0.01 F1233zdE + 0.96 F1234zeE + 0.01 F1234zeZ | | Organics 0.01 F1233xf + 0.01 F245cb + 0.01 F1233zdE + 0.01 F1234zeE + 0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.4 | 0 | 4.8 | 0 | 1.9 |
| 0.05 | 2.5 | 0.05 | 5.7 | 0.05 | 3.0 |
| 0.1 | 2.5 | 0.1 | 5.8 | 0.1 | 3.0 |
| 0.15 | 2.5 | 0.15 | 5.8 | 0.15 | 3.0 |
| 0.2 | 2.5 | 0.2 | 5.8 | 0.2 | 3.0 |
| 0.25 | 2.5 | 0.25 | 5.8 | 0.25 | 3.0 |
| 0.3 | 2.5 | 0.3 | 5.8 | 0.3 | 3.0 |
| 0.35 | 2.5 | 0.35 | 5.7 | 0.35 | 3.0 |
| 0.4 | 2.5 | 0.4 | 5.7 | 0.4 | 3.0 |
| 0.45 | 2.5 | 0.45 | 5.7 | 0.45 | 3.0 |
| 0.5 | 2.5 | 0.5 | 5.7 | 0.5 | 3.0 |
| 0.55 | 2.5 | 0.55 | 5.6 | 0.55 | 3.0 |
| 0.6 | 2.5 | 0.6 | 5.6 | 0.6 | 3.0 |
| 0.65 | 2.5 | 0.65 | 5.5 | 0.65 | 3.0 |
| 0.7 | 2.5 | 0.7 | 5.3 | 0.7 | 3.0 |
| 0.75 | 2.5 | 0.75 | 5.1 | 0.75 | 3.0 |
| 0.8 | 2.4 | 0.8 | 4.7 | 0.8 | 2.8 |
| 0.85 | 2.2 | 0.85 | 4.3 | 0.85 | 2.6 |
| 0.9 | 2.0 | 0.9 | 3.6 | 0.9 | 2.3 |
| 0.95 | 1.7 | 0.95 | 2.6 | 0.95 | 1.9 |
| 1 | 1.2 | 1 | 1.2 | 1 | 1.2 |

HF - HCFO-1233xf - HFC-245cb - HFO-1234zeE - HFO-1234zeZ - HFO-1243zf

| Organics 0.2 F1233xf + 0.2 F245cb + 0.2 F1243zf + 0.2 F1234zeE + 0.2 F1234zeZ | | Organics 0.96 F1233xf + 0.01 F245cb + 0.01 F1243zf + 0.01 F1234zeE + 0.01 F1234zeZ | | Organics 0.01 F1233xf + 0.96 F245cb + 0.01 F1243zf + 0.01 F1234zeE + 0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 |
| 0.05 | 4.9 | 0.05 | 2.8 | 0.05 | 5.8 |
| 0.1 | 4.9 | 0.1 | 2.8 | 0.1 | 5.8 |
| 0.15 | 4.9 | 0.15 | 2.8 | 0.15 | 5.8 |
| 0.2 | 4.9 | 0.2 | 2.8 | 0.2 | 5.8 |
| 0.25 | 4.9 | 0.25 | 2.8 | 0.25 | 5.8 |
| 0.3 | 4.9 | 0.3 | 2.8 | 0.3 | 5.8 |
| 0.35 | 4.9 | 0.35 | 2.8 | 0.35 | 5.8 |
| 0.4 | 4.9 | 0.4 | 2.8 | 0.4 | 5.8 |
| 0.45 | 4.9 | 0.45 | 2.8 | 0.45 | 5.8 |
| 0.5 | 4.9 | 0.5 | 2.8 | 0.5 | 5.8 |
| 0.55 | 4.9 | 0.55 | 2.8 | 0.55 | 5.8 |
| 0.6 | 4.9 | 0.6 | 2.8 | 0.6 | 5.8 |
| 0.65 | 4.9 | 0.65 | 2.8 | 0.65 | 5.8 |
| 0.7 | 4.9 | 0.7 | 2.8 | 0.7 | 5.8 |
| 0.75 | 4.8 | 0.75 | 2.8 | 0.75 | 5.8 |
| 0.8 | 4.6 | 0.8 | 2.6 | 0.8 | 5.8 |
| 0.85 | 4.2 | 0.85 | 2.4 | 0.85 | 5.8 |
| 0.9 | 3.6 | 0.9 | 2.2 | 0.9 | 5.0 |
| 0.95 | 2.6 | 0.95 | 1.8 | 0.95 | 3.5 |
| 1 | 1.2 | 1 | 1.2 | 1 | 1.2 |

| Organics 0.01 F1233xf + 0.01 F245cb + 0.96 F1243zf + 0.01 F1234zeE + 0.01 F1234zeZ | | Organics 0.01 F1233xf + 0.01 F245cb + 0.01 F1243zf + 0.96 F1234zeE + 0.01 F1234zeZ | | Organics 0.01 F1233xf + 0.01 F245cb + 0.01 F1243zf + 0.01 F1234zeE + 0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.8 | 0 | 4.8 | 0 | 1.9 |
| 0.05 | 6.7 | 0.05 | 5.8 | 0.05 | 3.0 |
| 0.1 | 6.7 | 0.1 | 5.8 | 0.1 | 3.0 |
| 0.15 | 6.7 | 0.15 | 5.8 | 0.15 | 3.0 |
| 0.2 | 6.7 | 0.2 | 5.8 | 0.2 | 3.0 |
| 0.25 | 6.7 | 0.25 | 5.8 | 0.25 | 3.0 |
| 0.3 | 6.7 | 0.3 | 5.8 | 0.3 | 3.0 |
| 0.35 | 6.7 | 0.35 | 5.8 | 0.35 | 3.0 |
| 0.4 | 6.7 | 0.4 | 5.8 | 0.4 | 3.0 |
| 0.45 | 6.7 | 0.45 | 5.8 | 0.45 | 3.0 |
| 0.5 | 6.7 | 0.5 | 5.7 | 0.5 | 3.0 |
| 0.55 | 6.7 | 0.55 | 5.7 | 0.55 | 3.0 |
| 0.6 | 6.6 | 0.6 | 5.6 | 0.6 | 3.0 |
| 0.65 | 6.6 | 0.65 | 5.5 | 0.65 | 3.0 |
| 0.7 | 6.5 | 0.7 | 5.4 | 0.7 | 3.0 |
| 0.75 | 6.3 | 0.75 | 5.1 | 0.75 | 3.0 |
| 0.8 | 6.0 | 0.8 | 4.8 | 0.8 | 2.9 |
| 0.85 | 5.6 | 0.85 | 4.3 | 0.85 | 2.7 |
| 0.9 | 4.7 | 0.9 | 3.6 | 0.9 | 2.4 |
| 0.95 | 3.4 | 0.95 | 2.6 | 0.95 | 1.9 |
| 1 | 1.2 | 1 | 1.2 | 1 | 1.2 |

HF - HCFO-1233xf - HFC-245cb - HFO-1234zeE - HCFO-1233zdE - HFO-1243zf

| Organics 0.2 F1233xf + 0.2 F245cb + 0.2 F1243zf + 0.2 F1234zeE + 0.2 F1233zdE | | Organics 0.96 F1233xf + 0.01 F245cb + 0.01 F1243zf + 0.01 F1234zeE + 0.01 F1233zdE | | Organics 0.01 F1233xf + 0.96 F245cb + 0.01 F1243zf + 0.01 F1234zeE + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 |
| 0.05 | 4.9 | 0.05 | 2.8 | 0.05 | 5.8 |
| 0.1 | 4.9 | 0.1 | 2.8 | 0.1 | 5.8 |
| 0.15 | 4.9 | 0.15 | 2.8 | 0.15 | 5.8 |
| 0.2 | 4.9 | 0.2 | 2.8 | 0.2 | 5.8 |
| 0.25 | 4.9 | 0.25 | 2.8 | 0.25 | 5.8 |
| 0.3 | 4.9 | 0.3 | 2.8 | 0.3 | 5.8 |
| 0.35 | 4.9 | 0.35 | 2.8 | 0.35 | 5.8 |
| 0.4 | 4.9 | 0.4 | 2.8 | 0.4 | 5.8 |
| 0.45 | 4.9 | 0.45 | 2.8 | 0.45 | 5.8 |
| 0.5 | 4.9 | 0.5 | 2.8 | 0.5 | 5.8 |
| 0.55 | 4.9 | 0.55 | 2.8 | 0.55 | 5.8 |
| 0.6 | 4.9 | 0.6 | 2.8 | 0.6 | 5.8 |
| 0.65 | 4.9 | 0.65 | 2.8 | 0.65 | 5.8 |
| 0.7 | 4.9 | 0.7 | 2.8 | 0.7 | 5.8 |
| 0.75 | 4.7 | 0.75 | 2.8 | 0.75 | 5.8 |
| 0.8 | 4.5 | 0.8 | 2.6 | 0.8 | 5.8 |
| 0.85 | 4.1 | 0.85 | 2.4 | 0.85 | 5.8 |
| 0.9 | 3.5 | 0.9 | 2.2 | 0.9 | 5.0 |
| 0.95 | 2.6 | 0.95 | 1.7 | 0.95 | 3.5 |
| 1 | 1.2 | 1 | 1.2 | 1 | 1.2 |

| Organics 0.01 F1233xf + 0.01 F245cb + 0.96 F1243zf + 0.01 F1234zeE + 0.01 F1233zdE | | Organics 0.01 F1233xf + 0.01 F245cb + 0.01 F1243zf + 0.96 F1234zeE + 0.01 F1233zdE | | Organics 0.01 F1233xf + 0.01 F245cb + 0.01 F1243zf + 0.01 F1234zeE + 0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.8 | 0 | 4.8 | 0 | 1.5 |
| 0.05 | 6.7 | 0.05 | 5.8 | 0.05 | 2.6 |
| 0.1 | 6.7 | 0.1 | 5.8 | 0.1 | 2.6 |
| 0.15 | 6.7 | 0.15 | 5.8 | 0.15 | 2.6 |
| 0.2 | 6.7 | 0.2 | 5.8 | 0.2 | 2.6 |
| 0.25 | 6.7 | 0.25 | 5.8 | 0.25 | 2.6 |
| 0.3 | 6.7 | 0.3 | 5.8 | 0.3 | 2.6 |
| 0.35 | 6.7 | 0.35 | 5.8 | 0.35 | 2.6 |
| 0.4 | 6.7 | 0.4 | 5.8 | 0.4 | 2.6 |
| 0.45 | 6.7 | 0.45 | 5.8 | 0.45 | 2.6 |
| 0.5 | 6.7 | 0.5 | 5.7 | 0.5 | 2.6 |
| 0.55 | 6.7 | 0.55 | 5.7 | 0.55 | 2.6 |
| 0.6 | 6.6 | 0.6 | 5.6 | 0.6 | 2.6 |
| 0.65 | 6.6 | 0.65 | 5.5 | 0.65 | 2.5 |
| 0.7 | 6.5 | 0.7 | 5.4 | 0.7 | 2.5 |
| 0.75 | 6.3 | 0.75 | 5.1 | 0.75 | 2.5 |
| 0.8 | 6.0 | 0.8 | 4.8 | 0.8 | 2.4 |
| 0.85 | 5.6 | 0.85 | 4.3 | 0.85 | 2.3 |
| 0.9 | 4.7 | 0.9 | 3.6 | 0.9 | 2.0 |
| 0.95 | 3.3 | 0.95 | 2.6 | 0.95 | 1.7 |
| 1 | 1.2 | 1 | 1.2 | 1 | 1.2 |

HF - HCFO-1233xf - HFC-245cb - HFO-1234zeZ - HCFO-1233zdE - HFO-1243zf

| Organics 0.2 F1233xf + 0.2 F245cb + 0.2 F1243zf + 0.2 F1234zeZ + 0.2 F1233zdE | | Organics 0.96 F1233xf + 0.01 F245cb + 0.01 F1243zf + 0.01 F1234zeZ + 0.01 F1233zdE | | Organics 0.01 F1233xf + 0.96 F245cb + 0.01 F1243zf + 0.01 F1234zeZ + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.2 | 0 | 1.6 | 0 | 4.6 |
| 0.05 | 4.3 | 0.05 | 2.7 | 0.05 | 5.7 |
| 0.1 | 4.3 | 0.1 | 2.7 | 0.1 | 5.7 |
| 0.15 | 4.3 | 0.15 | 2.7 | 0.15 | 5.7 |
| 0.2 | 4.3 | 0.2 | 2.7 | 0.2 | 5.7 |
| 0.25 | 4.3 | 0.25 | 2.7 | 0.25 | 5.7 |
| 0.3 | 4.3 | 0.3 | 2.7 | 0.3 | 5.7 |
| 0.35 | 4.3 | 0.35 | 2.7 | 0.35 | 5.7 |
| 0.4 | 4.3 | 0.4 | 2.7 | 0.4 | 5.8 |
| 0.45 | 4.3 | 0.45 | 2.7 | 0.45 | 5.8 |
| 0.5 | 4.3 | 0.5 | 2.7 | 0.5 | 5.8 |
| 0.55 | 4.3 | 0.55 | 2.7 | 0.55 | 5.8 |
| 0.6 | 4.3 | 0.6 | 2.7 | 0.6 | 5.8 |
| 0.65 | 4.3 | 0.65 | 2.7 | 0.65 | 5.8 |
| 0.7 | 4.3 | 0.7 | 2.7 | 0.7 | 5.8 |
| 0.75 | 4.3 | 0.75 | 2.7 | 0.75 | 5.8 |
| 0.8 | 4.1 | 0.8 | 2.6 | 0.8 | 5.8 |
| 0.85 | 3.8 | 0.85 | 2.4 | 0.85 | 5.8 |
| 0.9 | 3.3 | 0.9 | 2.1 | 0.9 | 5.0 |
| 0.95 | 2.4 | 0.95 | 1.7 | 0.95 | 3.5 |
| 1 | 1.2 | 1 | 1.2 | 1 | 1.2 |

| Organics 0.01 F1233xf + 0.01 F245cb + 0.96 F1243zf + 0.01 F1234zeZ + 0.01 F1233zdE | | Organics 0.01 F1233xf + 0.01 F245cb + 0.01 F1243zf + 0.96 F1234zeZ + 0.01 F1233zdE | | Organics 0.01 F1233xf + 0.01 F245cb + 0.01 F1243zf + 0.01 F1234zeZ + 0.96 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.7 | 0 | 1.9 | 0 | 1.4 |
| 0.05 | 6.7 | 0.05 | 3.0 | 0.05 | 2.5 |
| 0.1 | 6.7 | 0.1 | 3.0 | 0.1 | 2.5 |
| 0.15 | 6.7 | 0.15 | 3.0 | 0.15 | 2.5 |
| 0.2 | 6.7 | 0.2 | 3.0 | 0.2 | 2.5 |
| 0.25 | 6.7 | 0.25 | 3.0 | 0.25 | 2.5 |
| 0.3 | 6.7 | 0.3 | 3.0 | 0.3 | 2.5 |
| 0.35 | 6.7 | 0.35 | 3.0 | 0.35 | 2.5 |
| 0.4 | 6.7 | 0.4 | 3.0 | 0.4 | 2.5 |
| 0.45 | 6.7 | 0.45 | 3.0 | 0.45 | 2.5 |
| 0.5 | 6.7 | 0.5 | 3.0 | 0.5 | 2.5 |
| 0.55 | 6.7 | 0.55 | 3.0 | 0.55 | 2.5 |
| 0.6 | 6.6 | 0.6 | 3.0 | 0.6 | 2.5 |
| 0.65 | 6.6 | 0.65 | 3.0 | 0.65 | 2.5 |
| 0.7 | 6.5 | 0.7 | 3.0 | 0.7 | 2.5 |
| 0.75 | 6.3 | 0.75 | 3.0 | 0.75 | 2.5 |
| 0.8 | 6.0 | 0.8 | 2.9 | 0.8 | 2.4 |
| 0.85 | 5.5 | 0.85 | 2.7 | 0.85 | 2.3 |
| 0.9 | 4.7 | 0.9 | 2.3 | 0.9 | 2.0 |
| 0.95 | 3.3 | 0.95 | 1.9 | 0.95 | 1.7 |
| 1 | 1.2 | 1 | 1.2 | 1 | 1.2 |

HF - HCFO-1233xf - HFO-1234zeE- HFO-1234zeZ - HCFO-1233zdE- HFO-1243zf

| Organics 0.2 F1233xf + 0.2 F1243zf + 0.2 F1233zdE + 0.2 F1234zeE + 0.2 F1234zeZ | | Organics 0.96 F1233xf + 0.01 F1243zf + 0.01 F1233zdE + 0.01 F1234zeE + 0.01 F1234zeZ | | Organics 0.01 F1233xf + 0.96 F1243zf + 0.01 F1233zdE + 0.01 F1234zeE + 0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.2 | 0 | 1.6 | 0 | 5.7 |
| 0.05 | 4.3 | 0.05 | 2.7 | 0.05 | 6.7 |
| 0.1 | 4.3 | 0.1 | 2.7 | 0.1 | 6.7 |
| 0.15 | 4.3 | 0.15 | 2.7 | 0.15 | 6.7 |
| 0.2 | 4.3 | 0.2 | 2.7 | 0.2 | 6.7 |
| 0.25 | 4.3 | 0.25 | 2.7 | 0.25 | 6.7 |
| 0.3 | 4.3 | 0.3 | 2.7 | 0.3 | 6.7 |
| 0.35 | 4.3 | 0.35 | 2.7 | 0.35 | 6.7 |
| 0.4 | 4.3 | 0.4 | 2.7 | 0.4 | 6.7 |
| 0.45 | 4.3 | 0.45 | 2.7 | 0.45 | 6.7 |
| 0.5 | 4.3 | 0.5 | 2.7 | 0.5 | 6.7 |
| 0.55 | 4.2 | 0.55 | 2.7 | 0.55 | 6.6 |
| 0.6 | 4.2 | 0.6 | 2.7 | 0.6 | 6.6 |
| 0.65 | 4.2 | 0.65 | 2.7 | 0.65 | 6.6 |
| 0.7 | 4.2 | 0.7 | 2.7 | 0.7 | 6.5 |
| 0.75 | 4.0 | 0.75 | 2.7 | 0.75 | 6.3 |
| 0.8 | 3.8 | 0.8 | 2.6 | 0.8 | 6.0 |
| 0.85 | 3.5 | 0.85 | 2.4 | 0.85 | 5.5 |
| 0.9 | 3.0 | 0.9 | 2.1 | 0.9 | 4.7 |
| 0.95 | 2.2 | 0.95 | 1.7 | 0.95 | 3.3 |
| 1 | 1.2 | 1 | 1.2 | 1 | 1.2 |

-continued

| Organics 0.01 F1233xf + 0.01 F1243zf + 0.96 F1233zdE + 0.01 F1234zeE + 0.01 F1234zeZ | | Organics 0.01 F1233xf + 0.01 F1243zf + 0.01 F1233zdE + 0.96 F1234zeE + 0.01 F1234zeZ | | Organics 0.01 F1233xf + 0.01 F1243zf + 0.01 F1233zdE + 0.01 F1234zeE + 0.96 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.4 | 0 | 4.8 | 0 | 1.9 |
| 0.05 | 2.5 | 0.05 | 5.7 | 0.05 | 3.0 |
| 0.1 | 2.5 | 0.1 | 5.8 | 0.1 | 3.0 |
| 0.15 | 2.5 | 0.15 | 5.8 | 0.15 | 3.0 |
| 0.2 | 2.5 | 0.2 | 5.8 | 0.2 | 3.0 |
| 0.25 | 2.5 | 0.25 | 5.8 | 0.25 | 3.0 |
| 0.3 | 2.5 | 0.3 | 5.8 | 0.3 | 3.0 |
| 0.35 | 2.5 | 0.35 | 5.8 | 0.35 | 3.0 |
| 0.4 | 2.5 | 0.4 | 5.8 | 0.4 | 3.0 |
| 0.45 | 2.5 | 0.45 | 5.7 | 0.45 | 3.0 |
| 0.5 | 2.5 | 0.5 | 5.7 | 0.5 | 3.0 |
| 0.55 | 2.5 | 0.55 | 5.7 | 0.55 | 3.0 |
| 0.6 | 2.5 | 0.6 | 5.6 | 0.6 | 3.0 |
| 0.65 | 2.5 | 0.65 | 5.5 | 0.65 | 3.0 |
| 0.7 | 2.5 | 0.7 | 5.3 | 0.7 | 3.0 |
| 0.75 | 2.5 | 0.75 | 5.1 | 0.75 | 3.0 |
| 0.8 | 2.4 | 0.8 | 4.7 | 0.8 | 2.8 |
| 0.85 | 2.2 | 0.85 | 4.3 | 0.85 | 2.6 |
| 0.9 | 2.0 | 0.9 | 3.6 | 0.9 | 2.3 |
| 0.95 | 1.7 | 0.95 | 2.6 | 0.95 | 1.9 |
| 1 | 1.2 | 1 | 1.2 | 1 | 1.2 |

Example 11: Temperature and Pressure Range of Systems with 6 Compounds

| System with 6 compounds | Boiling point range | |
|---|---|---|
| | Temperature ° C. | Pressure bar abs |
| HF-HCFO-1233xf-HFO-1234yf-HFC-245cb-HFO-1234zeE-HFO-1234zeZ | 0 to 40 | −1.0 to −11.6 |
| HF-HCFO-1233xf-HFO-1234yf-HFC-245cb-HFO-1234zeE-HCFO-1233zdE | 0 to 40 | −0.9 to −11.6 |
| HF-HCFO-1233xf-HFO-1234yf-HFC-245cb-HFO-1234zeE-HFO-1243zf | 0 to 40 | −1.0 to −11.6 |
| HF-HCFO-1233xf-HFO-1234yf-HFC-245cb-HFO-1234zeZ-HCFO-1233zdE | 0 to 40 | −0.9 to −11.5 |
| HF-HCFO-1233xf-HFO-1234yf-HFC-245cb-HFO-1234zeZ-HFO-1243zf | 0 to 40 | −1.0 to −11.6 |
| HF-HCFO-1233xf-HFO-1234yf-HFC-245cb-HCFO-1233zdE-HFO-1243zf | 0 to 40 | −0.9 to −11.6 |
| HF-HCFO-1233xf-HFO-1234yf-HFO-1234zeE-HFO-1234zeZ-HCFO-1233zdE | 0 to 40 | −0.9 to −11.5 |
| HF-HCFO-1233xf-HFO-1234yf-HFO-1234zeE-HFO-1234zeZ-HFO-1243zf | 0 to 40 | −1.0 to −11.6 |
| HF-HCFO-1233xf-HFO-1234yf-HFO-1234zeE-HCFO-1233zdE-HFO-1243zf | 0 to 40 | −0.9 to −11.6 |
| HF-HCFO-1233xf-HFO-1234yf-HFO-1234zeZ-HCFO-1233zdE-HFO-1243zf | 0 to 40 | −0.9 to −11.6 |
| HF-HCFO-1233xf-HFC-245cb-HFO-1234zeE-HFO-1234zeZ-HCFO-1233zdE | 0 to 40 | −0.9 to −9.0 |
| HF-HCFO-1233xf-HFC-245cb-HFO-1234zeE-HFO-1234zeZ-HFO-1243zf | 0 to 40 | −1.0 to −10.3 |
| HF-HCFO-1233xf-HFC-245cb-HFO-1234zeE-HCFO-1233zdE-HFO-1243zf | 0 to 40 | −0.9 to −10.3 |
| HF-HCFO-1233xf-HFC-245cb-HFO-1234zeZ-HCFO-1233zdE-HFO-1243zf | 0 to 40 | −1.0 to −10.3 |
| HF-HCFO-1233xf-HFO-1234zeE-HFO-1234zeZ-HCFO-1233zdE-HFO-1243zf | 0 to 40 | −0.9 to −10.3 |

Example 12: Decantation Range of Systems with 6 Compounds

| | Decantation ranges Mass percentage of HF | | |
|---|---|---|---|
| System with 6 compounds | Isotherm 0° C. | Isotherm 25° C. | Isotherm 40° C. |
| HF-HCFO-1233xf-HFO-1234yf-HFC-245cb-HFO-1234zeE-HFO-1234zeZ | 5-75 | 5-70 | 15-55 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeE-HFO-1243zf | 5-75 | 10-65 | * |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HFO-1234zeZ-HFO-1243zf | 5-75 | 10-70 | 15-50 |
| HF-HCFO-1233xf-HFO-1234yf-HFC-245cb-HCFO-1233zdE-HFO-1243zf | 5-75 | 5-70 | 15-55 |
| HF-HCFO-1233xf-HFO-1234yf-HFO-1234zeE-HFO-1234zeZ-HCFO-1233zdE | 5-75 | 5-65 | 10-55 |
| HF-HCFO-1233xf-HFO-1234yf-HFO-1234zeE-HFO-1234zeZ-HFO-1234zf | 5-70 | 10-65 | * |
| HF-HCFO-1233xf-HFO-1234yf-HFO-1234zeE-HCFO-1233zdE-HFO-1233zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HCFO-1233xf-HFC-245cb-HFO-1234zeE-HFO-1234zeZ-HCFO-1233zdE | 5-75 | 5-70 | 10-65 |
| HF-HCFO-1233xf-HFC-245cb-HFO-1234zeE-HFO-1234zeZ-HFO-1243zf | 5-75 | 10-70 | 15-45 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |
| HF-HCFO-1233xf-HFO-1234zeE-HFO-1234zeZ-HCFO-1233zdE-HFO-1243zf | 5-75 | 5-65 | 10-55 |

Example 13: Systems with Seven Compounds, Isotherm at 25° C.

HF - HCFO-1233xf - HFC-245cb - HCFO-1233zdE - HFO-1234zeE - HFO-1234zeZ - HFO-1243zf

| Organics | Organics | Organics | Organics |
|---|---|---|---|
| 0.15 F1233xf + 0.17 F245cb + 0.17 F1233zdE + 0.17 F1234zeE + 0.17 F1234zeZ + 0.17 F1243zf | 0.95 F1233xf + 0.01 F245cb + 0.01 F1233zdE + 0.01 F1234zeE + 0.01 F1234zeZ + 0.01 F1243zf | 0.01 F1233xf + 0.95 F245cb + 0.01 F1233zdE + 0.01 F1234zeE + 0.01 F1234zeZ + 0.01 F1243zf | 0.01 F1233xf + 0.01 F245cb + 0.95 F1233zdE + 0.01 F1234zeE + 0.01 F1234zeZ + 0.01 F1243zf |

| MASSFRAC HF | TOTAL PRESS. bar | MASSFRAC HF | TOTAL PRESS. bar | MASSFR HF | TOTAL PRESS. bar | MASSFRAC HF | TOTAL PRESS. bar |
|---|---|---|---|---|---|---|---|
| 0 | 3.5 | 0 | 1.7 | 0 | 4.6 | 0 | 1.5 |
| 0.05 | 4.6 | 0.05 | 2.8 | 0.05 | 5.7 | 0.05 | 2.6 |
| 0.1 | 4.6 | 0.1 | 2.8 | 0.1 | 5.7 | 0.1 | 2.6 |
| 0.15 | 4.6 | 0.15 | 2.8 | 0.15 | 5.7 | 0.15 | 2.6 |
| 0.2 | 4.6 | 0.2 | 2.8 | 0.2 | 5.7 | 0.2 | 2.6 |
| 0.25 | 4.6 | 0.25 | 2.8 | 0.25 | 5.8 | 0.25 | 2.6 |
| 0.3 | 4.6 | 0.3 | 2.8 | 0.3 | 5.8 | 0.3 | 2.6 |
| 0.35 | 4.6 | 0.35 | 2.8 | 0.35 | 5.8 | 0.35 | 2.6 |
| 0.4 | 4.6 | 0.4 | 2.8 | 0.4 | 5.8 | 0.4 | 2.6 |
| 0.45 | 4.6 | 0.45 | 2.8 | 0.45 | 5.8 | 0.45 | 2.6 |
| 0.5 | 4.6 | 0.5 | 2.8 | 0.5 | 5.8 | 0.5 | 2.6 |
| 0.55 | 4.6 | 0.55 | 2.8 | 0.55 | 5.8 | 0.55 | 2.6 |
| 0.6 | 4.6 | 0.6 | 2.8 | 0.6 | 5.8 | 0.6 | 2.6 |
| 0.65 | 4.6 | 0.65 | 2.8 | 0.65 | 5.8 | 0.65 | 2.6 |
| 0.7 | 4.6 | 0.7 | 2.8 | 0.7 | 5.8 | 0.7 | 2.6 |
| 0.75 | 4.5 | 0.75 | 2.8 | 0.75 | 5.8 | 0.75 | 2.6 |
| 0.8 | 4.2 | 0.8 | 2.6 | 0.8 | 5.8 | 0.8 | 2.4 |
| 0.85 | 3.9 | 0.85 | 2.4 | 0.85 | 5.8 | 0.85 | 2.3 |
| 0.9 | 3.3 | 0.9 | 2.2 | 0.9 | 4.9 | 0.9 | 2.0 |

| | | | | | | | |
|---|---|---|---|---|---|---|---|
| 0.95 | 2.5 | 0.95 | 1.8 | 0.95 | 3.5 | 0.95 | 1.7 |
| 1 | 1.2 | 1 | 1.2 | 1 | 1.2 | 1 | 1.2 |

| Organics<br>0.01 F1233xf +<br>0.01 F245cb +<br>0.01 F1233zdE +<br>0.95 F1234zeE +<br>0.01 F1234zeZ +<br>0.01 F1243zf | | Organics<br>0.01 F1233xf +<br>0.01 F245cb +<br>0.01 F1233zdE +<br>0.01 F1234zeE +<br>0.01 F1234zeZ +<br>0.95 F1243zf | | Organics<br>0.01 F1233xf +<br>0.01 F245cb +<br>0.01 F1233zdE +<br>0.01 F1234zeE +<br>0.95 F1234zeZ +<br>0.01 F1243zf | |
|---|---|---|---|---|---|
| MASSFRAC HF | TOTAL PRESS. bar | MASSFRAC HF | TOTAL PRESS. bar | MASSFRAC HF | TOTAL PRESS.RE bar |
| 0 | 4.8 | 0 | 5.7 | 0 | 1.9 |
| 0.05 | 5.7 | 0.05 | 6.7 | 0.05 | 3.0 |
| 0.1 | 5.8 | 0.1 | 6.7 | 0.1 | 3.0 |
| 0.15 | 5.8 | 0.15 | 6.7 | 0.15 | 3.0 |
| 0.2 | 5.8 | 0.2 | 6.7 | 0.2 | 3.0 |
| 0.25 | 5.8 | 0.25 | 6.7 | 0.25 | 3.0 |
| 0.3 | 5.8 | 0.3 | 6.7 | 0.3 | 3.0 |
| 0.35 | 5.8 | 0.35 | 6.7 | 0.35 | 3.0 |
| 0.4 | 5.8 | 0.4 | 6.7 | 0.4 | 3.0 |
| 0.45 | 5.7 | 0.45 | 6.7 | 0.45 | 3.0 |
| 0.5 | 5.7 | 0.5 | 6.7 | 0.5 | 3.0 |
| 0.55 | 5.7 | 0.55 | 6.6 | 0.55 | 3.0 |
| 0.6 | 5.6 | 0.6 | 6.6 | 0.6 | 3.0 |
| 0.65 | 5.5 | 0.65 | 6.6 | 0.65 | 3.0 |
| 0.7 | 5.3 | 0.7 | 6.5 | 0.7 | 3.0 |
| 0.75 | 5.1 | 0.75 | 6.3 | 0.75 | 3.0 |
| 0.8 | 4.8 | 0.8 | 6.0 | 0.8 | 2.9 |
| 0.85 | 4.3 | 0.85 | 5.5 | 0.85 | 2.7 |
| 0.9 | 3.6 | 0.9 | 4.7 | 0.9 | 2.4 |
| 0.95 | 2.6 | 0.95 | 3.3 | 0.95 | 1.9 |
| 1 | 1.2 | 1 | 1.2 | 1 | 1.2 |

HF - HCFO-1233xf - HFO-1234yf - HFC-245cb - HCFO-1233zdE - HFO-1234zeE -HFO-1234zeZ

| Organics<br>0.15 F1233xf +<br>0.17 F1234yf +<br>0.17 F245cb +<br>0.17 F1233zdE +<br>0.17 F1234zeE +<br>0.17 F1234zeZ | | Organics<br>0.01 F1233xf +<br>0.95 F1234yf +<br>0.01 F245cb +<br>0.01 F1233zdE +<br>0.01 F1234zeE +<br>0.01 F1234zeZ | | Organics<br>0.01 F1233xf +<br>0.01 F1234yf +<br>0.95 F245cb +<br>0.01 F1233zdE +<br>0.01 F1234zeE +<br>0.01 F1234zeZ | | Organics<br>0.01 F1233xf +<br>0.01 F1234yf +<br>0.01 F245cb +<br>0.95 F1233zdE +<br>0.01 F1234zeE +<br>0.01 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 6.6 | 0 | 4.6 | 0 | 1.5 |
| 0.05 | 4.7 | 0.05 | 7.6 | 0.05 | 5.8 | 0.05 | 2.6 |
| 0.1 | 4.7 | 0.1 | 7.6 | 0.1 | 5.8 | 0.1 | 2.6 |
| 0.15 | 4.7 | 0.15 | 7.6 | 0.15 | 5.8 | 0.15 | 2.6 |
| 0.2 | 4.7 | 0.2 | 7.6 | 0.2 | 5.8 | 0.2 | 2.6 |
| 0.25 | 4.7 | 0.25 | 7.6 | 0.25 | 5.8 | 0.25 | 2.6 |
| 0.3 | 4.7 | 0.3 | 7.6 | 0.3 | 5.8 | 0.3 | 2.6 |
| 0.35 | 4.7 | 0.35 | 7.6 | 0.35 | 5.8 | 0.35 | 2.6 |
| 0.4 | 4.7 | 0.4 | 7.6 | 0.4 | 5.8 | 0.4 | 2.6 |
| 0.45 | 4.7 | 0.45 | 7.6 | 0.45 | 5.8 | 0.45 | 2.6 |
| 0.5 | 4.7 | 0.5 | 7.6 | 0.5 | 5.8 | 0.5 | 2.6 |
| 0.55 | 4.7 | 0.55 | 7.6 | 0.55 | 5.8 | 0.55 | 2.6 |
| 0.6 | 4.7 | 0.6 | 7.6 | 0.6 | 5.8 | 0.6 | 2.6 |
| 0.65 | 4.7 | 0.65 | 7.6 | 0.65 | 5.8 | 0.65 | 2.6 |
| 0.7 | 4.7 | 0.7 | 7.6 | 0.7 | 5.8 | 0.7 | 2.6 |
| 0.75 | 4.6 | 0.75 | 7.4 | 0.75 | 5.8 | 0.75 | 2.6 |
| 0.8 | 4.4 | 0.8 | 7.1 | 0.8 | 5.8 | 0.8 | 2.5 |
| 0.85 | 4.1 | 0.85 | 6.5 | 0.85 | 5.8 | 0.85 | 2.3 |
| 0.9 | 3.5 | 0.9 | 5.5 | 0.9 | 5.0 | 0.9 | 2.0 |
| 0.95 | 2.5 | 0.95 | 3.8 | 0.95 | 3.5 | 0.95 | 1.7 |
| 1 | 1.2 | 1 | 1.2 | 1 | 1.2 | 1 | 1.2 |

-continued

| Organics<br>0.01 F1233xf +<br>0.01 F1234yf +<br>0.01 F245cb +<br>0.01 F1233zdE +<br>0.95 F1234zeE +<br>0.01 F1234zeZ | | Organics<br>0.01 F1233xf +<br>0.01 F1234yf +<br>0.01 F245cb +<br>0.01 F1233zdE +<br>0.01 F1234zeE +<br>0.95 F1234zeZ | | Organics<br>0.95 F1233xf +<br>0.01 F1234yf +<br>0.01 F245cb +<br>0.01 F1233zdE +<br>0.01 F1234zeE +<br>0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.8 | 0 | 1.9 | 0 | 1.7 |
| 0.05 | 5.8 | 0.05 | 3.0 | 0.05 | 2.8 |
| 0.1 | 5.8 | 0.1 | 3.0 | 0.1 | 2.8 |
| 0.15 | 5.8 | 0.15 | 3.0 | 0.15 | 2.8 |
| 0.2 | 5.8 | 0.2 | 3.0 | 0.2 | 2.8 |
| 0.25 | 5.8 | 0.25 | 3.0 | 0.25 | 2.8 |
| 0.3 | 5.8 | 0.3 | 3.0 | 0.3 | 2.8 |
| 0.35 | 5.8 | 0.35 | 3.0 | 0.35 | 2.8 |
| 0.4 | 5.8 | 0.4 | 3.0 | 0.4 | 2.8 |
| 0.45 | 5.7 | 0.45 | 3.0 | 0.45 | 2.8 |
| 0.5 | 5.7 | 0.5 | 3.0 | 0.5 | 2.8 |
| 0.55 | 5.7 | 0.55 | 3.0 | 0.55 | 2.8 |
| 0.6 | 5.6 | 0.6 | 3.0 | 0.6 | 2.8 |
| 0.65 | 5.5 | 0.65 | 3.0 | 0.65 | 2.8 |
| 0.7 | 5.3 | 0.7 | 3.0 | 0.7 | 2.8 |
| 0.75 | 5.1 | 0.75 | 3.0 | 0.75 | 2.8 |
| 0.8 | 4.8 | 0.8 | 2.9 | 0.8 | 2.6 |
| 0.85 | 4.3 | 0.85 | 2.7 | 0.85 | 2.5 |
| 0.9 | 3.6 | 0.9 | 2.4 | 0.9 | 2.2 |
| 0.95 | 2.6 | 0.95 | 1.9 | 0.95 | 1.8 |
| 1 | 1.2 | 1 | 1.2 | 1 | 1.2 |

HF - HCFO-1233xf - HFO-1234yf - HFC-245cb - HCFO-1233zdE - HFO-1234zeE -HFO-1243zf

| Organics<br>0.15 F1233xf +<br>0.17 F1234yf +<br>0.17 F245cb +<br>0.17 F1233zdE +<br>0.17 F1234zeE +<br>0.17 F1243zf | | Organics<br>0.01 F1233xf +<br>0.95 F1234yf +<br>0.01 F245cb +<br>0.01 F1233zdE +<br>0.01 F1234zeE +<br>0.01 F1243zf | | Organics<br>0.01 F1233xf +<br>0.01 F1234yf +<br>0.95 F245cb +<br>0.01 F1233zdE +<br>0.01 F1234zeE +<br>0.01 F1243zf | | Organics<br>0.01 F1233xf +<br>0.01 F1234yf +<br>0.01 F245cb +<br>0.95 F1233zdE +<br>0.01 F1234zeE +<br>0.01 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.6 | 0 | 4.6 | 0 | 1.5 |
| 0.05 | 5.4 | 0.05 | 7.6 | 0.05 | 5.8 | 0.05 | 2.6 |
| 0.1 | 5.4 | 0.1 | 7.6 | 0.1 | 5.8 | 0.1 | 2.6 |
| 0.15 | 5.4 | 0.15 | 7.6 | 0.15 | 5.8 | 0.15 | 2.6 |
| 0.2 | 5.4 | 0.2 | 7.6 | 0.2 | 5.8 | 0.2 | 2.6 |
| 0.25 | 5.4 | 0.25 | 7.6 | 0.25 | 5.8 | 0.25 | 2.6 |
| 0.3 | 5.4 | 0.3 | 7.6 | 0.3 | 5.8 | 0.3 | 2.6 |
| 0.35 | 5.4 | 0.35 | 7.6 | 0.35 | 5.8 | 0.35 | 2.6 |
| 0.4 | 5.4 | 0.4 | 7.6 | 0.4 | 5.8 | 0.4 | 2.6 |
| 0.45 | 5.4 | 0.45 | 7.6 | 0.45 | 5.8 | 0.45 | 2.6 |
| 0.5 | 5.4 | 0.5 | 7.6 | 0.5 | 5.8 | 0.5 | 2.6 |
| 0.55 | 5.4 | 0.55 | 7.6 | 0.55 | 5.8 | 0.55 | 2.6 |
| 0.6 | 5.4 | 0.6 | 7.6 | 0.6 | 5.8 | 0.6 | 2.6 |
| 0.65 | 5.4 | 0.65 | 7.6 | 0.65 | 5.8 | 0.65 | 2.6 |
| 0.7 | 5.4 | 0.7 | 7.6 | 0.7 | 5.8 | 0.7 | 2.6 |
| 0.75 | 5.3 | 0.75 | 7.4 | 0.75 | 5.8 | 0.75 | 2.6 |
| 0.8 | 5.0 | 0.8 | 7.1 | 0.8 | 5.8 | 0.8 | 2.5 |
| 0.85 | 4.6 | 0.85 | 6.5 | 0.85 | 5.8 | 0.85 | 2.3 |
| 0.9 | 3.9 | 0.9 | 5.5 | 0.9 | 5.0 | 0.9 | 2.1 |
| 0.95 | 2.8 | 0.95 | 3.8 | 0.95 | 3.5 | 0.95 | 1.7 |
| 1 | 1.2 | 1 | 1.2 | 1 | 1.2 | 1 | 1.2 |

-continued

| Organics 0.01 F1233xf + 0.01 F1234yf + 0.01 F245cb + 0.01 F1233zdE + 0.95 F1234zeE + 0.01 F1243zf | | Organics 0.01 F1233xf + 0.01 F1234yf + 0.01 F245cb + 0.01 F1233zdE + 0.01 F1234zeE + 0.95 F1243zf | | Organics 0.95 F1233xf + 0.01 F1234yf + 0.01 F245cb + 0.01 F1233zdE + 0.01 F1234zeE + 0.01 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.8 | 0 | 5.8 | 0 | 1.7 |
| 0.05 | 5.8 | 0.05 | 6.7 | 0.05 | 2.8 |
| 0.1 | 5.8 | 0.1 | 6.7 | 0.1 | 2.8 |
| 0.15 | 5.8 | 0.15 | 6.7 | 0.15 | 2.8 |
| 0.2 | 5.8 | 0.2 | 6.7 | 0.2 | 2.8 |
| 0.25 | 5.8 | 0.25 | 6.7 | 0.25 | 2.8 |
| 0.3 | 5.8 | 0.3 | 6.7 | 0.3 | 2.8 |
| 0.35 | 5.8 | 0.35 | 6.7 | 0.35 | 2.8 |
| 0.4 | 5.8 | 0.4 | 6.7 | 0.4 | 2.8 |
| 0.45 | 5.8 | 0.45 | 6.7 | 0.45 | 2.8 |
| 0.5 | 5.8 | 0.5 | 6.7 | 0.5 | 2.8 |
| 0.55 | 5.7 | 0.55 | 6.7 | 0.55 | 2.8 |
| 0.6 | 5.6 | 0.6 | 6.7 | 0.6 | 2.8 |
| 0.65 | 5.5 | 0.65 | 6.6 | 0.65 | 2.8 |
| 0.7 | 5.4 | 0.7 | 6.5 | 0.7 | 2.8 |
| 0.75 | 5.1 | 0.75 | 6.3 | 0.75 | 2.8 |
| 0.8 | 4.8 | 0.8 | 6.1 | 0.8 | 2.7 |
| 0.85 | 4.3 | 0.85 | 5.6 | 0.85 | 2.5 |
| 0.9 | 3.6 | 0.9 | 4.7 | 0.9 | 2.2 |
| 0.95 | 2.6 | 0.95 | 3.4 | 0.95 | 1.8 |
| 1 | 1.2 | 1 | 1.2 | 1 | 1.2 |

HF - HCFO-1233xf - HFO-1234yf - HFC-245cb - HCFO-1233zdE 5 - HFO-1243zf - HFO-1234zeZ

| Organics 0.15 F1233xf + 0.17 F1234yf + 0.17 F245cb + 0.17 F1243zf + 0.17 F1233zdE + 0.17 F1234zeZ | | Organics 0.01 F1233xf + 0.95 F1234yf + 0.01 F245cb + 0.01 F1243zf + 0.01 F1233zdE + 0.01 F1234zeZ | | Organics 0.01 F1233xf + 0.01 F1234yf + 0.95 F245cb + 0.01 F1243zf + 0.01 F1233zdE + 0.01 F1234zeZ | | Organics 0.01 F1233xf + 0.01 F1234yf + 0.01 F245cb + 0.95 F1243zf + 0.01 F1233zdE + 0.01 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 6.6 | 0 | 4.6 | 0 | 5.7 |
| 0.05 | 4.9 | 0.05 | 7.6 | 0.05 | 5.8 | 0.05 | 6.7 |
| 0.1 | 4.9 | 0.1 | 7.6 | 0.1 | 5.8 | 0.1 | 6.7 |
| 0.15 | 4.9 | 0.15 | 7.6 | 0.15 | 5.8 | 0.15 | 6.7 |
| 0.2 | 4.9 | 0.2 | 7.6 | 0.2 | 5.8 | 0.2 | 6.7 |
| 0.25 | 4.9 | 0.25 | 7.6 | 0.25 | 5.8 | 0.25 | 6.7 |
| 0.3 | 4.9 | 0.3 | 7.6 | 0.3 | 5.8 | 0.3 | 6.7 |
| 0.35 | 4.9 | 0.35 | 7.6 | 0.35 | 5.8 | 0.35 | 6.7 |
| 0.4 | 4.9 | 0.4 | 7.6 | 0.4 | 5.8 | 0.4 | 6.7 |
| 0.45 | 4.9 | 0.45 | 7.6 | 0.45 | 5.8 | 0.45 | 6.7 |
| 0.5 | 4.9 | 0.5 | 7.6 | 0.5 | 5.8 | 0.5 | 6.7 |
| 0.55 | 4.9 | 0.55 | 7.6 | 0.55 | 5.8 | 0.55 | 6.7 |
| 0.6 | 4.9 | 0.6 | 7.6 | 0.6 | 5.8 | 0.6 | 6.6 |
| 0.65 | 4.9 | 0.65 | 7.6 | 0.65 | 5.8 | 0.65 | 6.6 |
| 0.7 | 4.9 | 0.7 | 7.6 | 0.7 | 5.8 | 0.7 | 6.5 |
| 0.75 | 4.9 | 0.75 | 7.4 | 0.75 | 5.8 | 0.75 | 6.3 |
| 0.8 | 4.7 | 0.8 | 7.1 | 0.8 | 5.8 | 0.8 | 6.0 |
| 0.85 | 4.3 | 0.85 | 6.5 | 0.85 | 5.8 | 0.85 | 5.5 |
| 0.9 | 3.7 | 0.9 | 5.5 | 0.9 | 5.0 | 0.9 | 4.7 |
| 0.95 | 2.7 | 0.95 | 3.8 | 0.95 | 3.5 | 0.95 | 3.3 |
| 1 | 1.2 | 1 | 1.2 | 1 | 1.2 | 1 | 1.2 |

-continued

| Organics<br>0.01 F1233xf +<br>0.01 F1234yf +<br>0.01 F245cb +<br>0.01 F1243zf +<br>0.95 F1233zdE +<br>0.01 F1234zeZ | | Organics<br>0.01 F1233xf +<br>0.01 F1234yf +<br>0.01 F245cb +<br>0.01 F1243zf +<br>0.01 F1233zdE +<br>0.95 F1234zeZ | | Organics<br>0.95 F1233xf +<br>0.01 F1234yf +<br>0.01 F245cb +<br>0.01 F1243zf +<br>0.01 F1233zdE +<br>0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.9 | 0 | 1.7 |
| 0.05 | 2.6 | 0.05 | 3.0 | 0.05 | 2.8 |
| 0.1 | 2.6 | 0.1 | 3.0 | 0.1 | 2.8 |
| 0.15 | 2.6 | 0.15 | 3.0 | 0.15 | 2.8 |
| 0.2 | 2.6 | 0.2 | 3.0 | 0.2 | 2.8 |
| 0.25 | 2.6 | 0.25 | 3.0 | 0.25 | 2.8 |
| 0.3 | 2.6 | 0.3 | 3.0 | 0.3 | 2.8 |
| 0.35 | 2.6 | 0.35 | 3.0 | 0.35 | 2.8 |
| 0.4 | 2.6 | 0.4 | 3.0 | 0.4 | 2.8 |
| 0.45 | 2.6 | 0.45 | 3.0 | 0.45 | 2.8 |
| 0.5 | 2.6 | 0.5 | 3.0 | 0.5 | 2.8 |
| 0.55 | 2.6 | 0.55 | 3.0 | 0.55 | 2.8 |
| 0.6 | 2.6 | 0.6 | 3.0 | 0.6 | 2.8 |
| 0.65 | 2.6 | 0.65 | 3.0 | 0.65 | 2.8 |
| 0.7 | 2.6 | 0.7 | 3.0 | 0.7 | 2.8 |
| 0.75 | 2.6 | 0.75 | 3.0 | 0.75 | 2.8 |
| 0.8 | 2.5 | 0.8 | 2.9 | 0.8 | 2.7 |
| 0.85 | 2.3 | 0.85 | 2.7 | 0.85 | 2.5 |
| 0.9 | 2.0 | 0.9 | 2.4 | 0.9 | 2.2 |
| 0.95 | 1.7 | 0.95 | 1.9 | 0.95 | 1.8 |
| 1 | 1.2 | 1 | 1.2 | 1 | 1.2 |

HF - HCFO-1233xf - HFO-1234yf - HFC-245cb - HFO-1234zeE - HFO-1234zeZ - HFO-1243zf

| Organics<br>0.15 F1233xf +<br>0.17 F1234yf +<br>0.17 F245cb +<br>0.17 F1243zf +<br>0.17 F1234zeE +<br>0.17 F1234zeZ | | Organics<br>0.01 F1233xf +<br>0.95 F1234yf +<br>0.01 F245cb +<br>0.01 F1243zf +<br>0.01 F1234zeE +<br>0.01 F1234zeZ | | Organics<br>0.01 F1233xf +<br>0.01 F1234yf +<br>0.95 F245cb +<br>0.01 F1243zf +<br>0.01 F1234zeE +<br>0.01 F1234zeZ | | Organics<br>0.01 F1233xf +<br>0.01 F1234yf +<br>0.01 F245cb +<br>0.95 F1243zf +<br>0.01 F1234zeE +<br>0.01 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.6 | 0 | 4.6 | 0 | 5.8 |
| 0.05 | 5.5 | 0.05 | 7.6 | 0.05 | 5.8 | 0.05 | 6.7 |
| 0.1 | 5.5 | 0.1 | 7.6 | 0.1 | 5.8 | 0.1 | 6.7 |
| 0.15 | 5.5 | 0.15 | 7.6 | 0.15 | 5.8 | 0.15 | 6.7 |
| 0.2 | 5.5 | 0.2 | 7.6 | 0.2 | 5.8 | 0.2 | 6.7 |
| 0.25 | 5.5 | 0.25 | 7.6 | 0.25 | 5.8 | 0.25 | 6.7 |
| 0.3 | 5.5 | 0.3 | 7.6 | 0.3 | 5.8 | 0.3 | 6.7 |
| 0.35 | 5.5 | 0.35 | 7.6 | 0.35 | 5.8 | 0.35 | 6.7 |
| 0.4 | 5.5 | 0.4 | 7.6 | 0.4 | 5.8 | 0.4 | 6.7 |
| 0.45 | 5.5 | 0.45 | 7.6 | 0.45 | 5.8 | 0.45 | 6.7 |
| 0.5 | 5.5 | 0.5 | 7.6 | 0.5 | 5.8 | 0.5 | 6.7 |
| 0.55 | 5.5 | 0.55 | 7.6 | 0.55 | 5.8 | 0.55 | 6.7 |
| 0.6 | 5.5 | 0.6 | 7.6 | 0.6 | 5.8 | 0.6 | 6.7 |
| 0.65 | 5.5 | 0.65 | 7.6 | 0.65 | 5.8 | 0.65 | 6.6 |
| 0.7 | 5.5 | 0.7 | 7.6 | 0.7 | 5.8 | 0.7 | 6.5 |
| 0.75 | 5.3 | 0.75 | 7.4 | 0.75 | 5.8 | 0.75 | 6.3 |
| 0.8 | 5.1 | 0.8 | 7.1 | 0.8 | 5.8 | 0.8 | 6.1 |
| 0.85 | 4.6 | 0.85 | 6.5 | 0.85 | 5.8 | 0.85 | 5.6 |
| 0.9 | 3.9 | 0.9 | 5.5 | 0.9 | 5.0 | 0.9 | 4.7 |
| 0.95 | 2.8 | 0.95 | 3.8 | 0.95 | 3.5 | 0.95 | 3.4 |
| 1 | 1.2 | 1 | 1.2 | 1 | 1.2 | 1 | 1.2 |

| Organics<br>0.01 F1233xf +<br>0.01 F1234yf +<br>0.01 F245cb +<br>0.01 F1243zf +<br>0.95 F1234zeE +<br>0.01 F1234zeZ | | Organics<br>0.01 F1233xf +<br>0.01 F1234yf +<br>0.01 F245cb +<br>0.01 F1243zf +<br>0.01 F1234zeE +<br>0.95 F1234zeZ | | Organics<br>0.95 F1233xf +<br>0.01 F1234yf +<br>0.01 F245cb +<br>0.01 F1243zf +<br>0.01 F1234zeE +<br>0.01 F1234zeZ | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.8 | 0 | 2.0 | 0 | 1.7 |
| 0.05 | 5.8 | 0.05 | 3.1 | 0.05 | 2.8 |
| 0.1 | 5.8 | 0.1 | 3.1 | 0.1 | 2.8 |
| 0.15 | 5.8 | 0.15 | 3.1 | 0.15 | 2.8 |
| 0.2 | 5.8 | 0.2 | 3.1 | 0.2 | 2.8 |
| 0.25 | 5.8 | 0.25 | 3.1 | 0.25 | 2.8 |
| 0.3 | 5.8 | 0.3 | 3.1 | 0.3 | 2.8 |
| 0.35 | 5.8 | 0.35 | 3.1 | 0.35 | 2.8 |
| 0.4 | 5.8 | 0.4 | 3.1 | 0.4 | 2.8 |
| 0.45 | 5.8 | 0.45 | 3.1 | 0.45 | 2.8 |
| 0.5 | 5.8 | 0.5 | 3.1 | 0.5 | 2.8 |
| 0.55 | 5.7 | 0.55 | 3.1 | 0.55 | 2.8 |
| 0.6 | 5.6 | 0.6 | 3.1 | 0.6 | 2.8 |
| 0.65 | 5.5 | 0.65 | 3.1 | 0.65 | 2.8 |
| 0.7 | 5.4 | 0.7 | 3.1 | 0.7 | 2.8 |
| 0.75 | 5.1 | 0.75 | 3.1 | 0.75 | 2.8 |
| 0.8 | 4.8 | 0.8 | 2.9 | 0.8 | 2.7 |
| 0.85 | 4.3 | 0.85 | 2.7 | 0.85 | 2.5 |
| 0.9 | 3.6 | 0.9 | 2.4 | 0.9 | 2.2 |
| 0.95 | 2.6 | 0.95 | 1.9 | 0.95 | 1.8 |
| 1 | 1.2 | 1 | 1.2 | 1 | 1.2 |

HF - HCFO-1233xf - HFO-1234yf - HCFO-1233zdE - HFO-1234zeE 5 - HFO-1234zeZ - HFO-1243zf

| Organics<br>0.15 F1233xf +<br>0.17 F1234yf +<br>0.17 F1233zdE +<br>0.17 F1243zf +<br>0.17 F1234zeE +<br>0.17 F1234zeZ | | Organics<br>0.01 F1233xf +<br>0.95 F1234yf +<br>0.01 F1233zdE +<br>0.01 F1243zf +<br>0.01 F1234zeE +<br>0.01 F1234zeZ | | Organics<br>0.01 F1233xf +<br>0.01 F1234yf +<br>0.95 F1233zdE +<br>0.01 F1243zf +<br>0.01 F1234zeE +<br>0.01 F1234zeZ | | Organics<br>0.01 F1233xf +<br>0.01 F1234yf +<br>0.01 F1233zdE +<br>0.95 F1243zf +<br>0.01 F1234zeE +<br>0.01 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.6 | 0 | 1.5 | 0 | 5.7 |
| 0.05 | 5.0 | 0.05 | 7.6 | 0.05 | 2.6 | 0.05 | 6.7 |
| 0.1 | 4.9 | 0.1 | 7.6 | 0.1 | 2.6 | 0.1 | 6.7 |
| 0.15 | 4.9 | 0.15 | 7.6 | 0.15 | 2.6 | 0.15 | 6.7 |
| 0.2 | 4.9 | 0.2 | 7.6 | 0.2 | 2.6 | 0.2 | 6.7 |
| 0.25 | 4.9 | 0.25 | 7.6 | 0.25 | 2.6 | 0.25 | 6.7 |
| 0.3 | 4.9 | 0.3 | 7.6 | 0.3 | 2.6 | 0.3 | 6.7 |
| 0.35 | 4.9 | 0.35 | 7.6 | 0.35 | 2.6 | 0.35 | 6.7 |
| 0.4 | 4.9 | 0.4 | 7.6 | 0.4 | 2.6 | 0.4 | 6.7 |
| 0.45 | 4.9 | 0.45 | 7.6 | 0.45 | 2.6 | 0.45 | 6.7 |
| 0.5 | 4.9 | 0.5 | 7.6 | 0.5 | 2.6 | 0.5 | 6.7 |
| 0.55 | 4.9 | 0.55 | 7.6 | 0.55 | 2.6 | 0.55 | 6.7 |
| 0.6 | 4.9 | 0.6 | 7.6 | 0.6 | 2.6 | 0.6 | 6.6 |
| 0.65 | 4.9 | 0.65 | 7.6 | 0.65 | 2.6 | 0.65 | 6.6 |
| 0.7 | 4.8 | 0.7 | 7.6 | 0.7 | 2.6 | 0.7 | 6.5 |
| 0.75 | 4.7 | 0.75 | 7.4 | 0.75 | 2.6 | 0.75 | 6.3 |
| 0.8 | 4.4 | 0.8 | 7.1 | 0.8 | 2.5 | 0.8 | 6.0 |
| 0.85 | 4.0 | 0.85 | 6.5 | 0.85 | 2.3 | 0.85 | 5.5 |
| 0.9 | 3.4 | 0.9 | 5.5 | 0.9 | 2.0 | 0.9 | 4.7 |
| 0.95 | 2.5 | 0.95 | 3.8 | 0.95 | 1.7 | 0.95 | 3.3 |
| 1 | 1.2 | 1 | 1.2 | 1 | 1.2 | 1 | 1.2 |

| | Organics<br>0.01 F1233xf +<br>0.01 F1234yf +<br>0.01 F1233zdE +<br>0.01 F1243zf +<br>0.95 F1234zeE +<br>0.01 F1234zeZ | | Organics<br>0.01 F1233xf +<br>0.01 F1234yf +<br>0.01 F1233zdE +<br>0.01 F1243zf +<br>0.01 F1234zeE +<br>0.95 F1234zeZ | | Organics<br>0.95 F1233xf +<br>0.01 F1234yf +<br>0.01 F1233zdE +<br>0.01 F1243zf +<br>0.01 F1234zeE +<br>0.01 F1234zeZ |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.8 | 0 | 1.9 | 0 | 1.7 |
| 0.05 | 5.8 | 0.05 | 3.0 | 0.05 | 2.8 |
| 0.1 | 5.8 | 0.1 | 3.0 | 0.1 | 2.8 |
| 0.15 | 5.8 | 0.15 | 3.0 | 0.15 | 2.8 |
| 0.2 | 5.8 | 0.2 | 3.0 | 0.2 | 2.8 |
| 0.25 | 5.8 | 0.25 | 3.0 | 0.25 | 2.8 |
| 0.3 | 5.8 | 0.3 | 3.0 | 0.3 | 2.8 |
| 0.35 | 5.8 | 0.35 | 3.0 | 0.35 | 2.8 |
| 0.4 | 5.8 | 0.4 | 3.0 | 0.4 | 2.8 |
| 0.45 | 5.8 | 0.45 | 3.0 | 0.45 | 2.8 |
| 0.5 | 5.7 | 0.5 | 3.0 | 0.5 | 2.8 |
| 0.55 | 5.7 | 0.55 | 3.0 | 0.55 | 2.8 |
| 0.6 | 5.6 | 0.6 | 3.0 | 0.6 | 2.8 |
| 0.65 | 5.5 | 0.65 | 3.0 | 0.65 | 2.8 |
| 0.7 | 5.3 | 0.7 | 3.0 | 0.7 | 2.8 |
| 0.75 | 5.1 | 0.75 | 3.0 | 0.75 | 2.8 |
| 0.8 | 4.8 | 0.8 | 2.9 | 0.8 | 2.6 |
| 0.85 | 4.3 | 0.85 | 2.7 | 0.85 | 2.5 |
| 0.9 | 3.6 | 0.9 | 2.4 | 0.9 | 2.2 |
| 0.95 | 2.6 | 0.95 | 1.9 | 0.95 | 1.8 |
| 1 | 1.2 | 1 | 1.2 | 1 | 1.2 |

HF - HCFO-1233xf - HCFC-244bb- HFC-245fa - Trifluoropropyne- HFO-1225yeZ-HFO-1225zc

| | Organics<br>0.15 F1233xf +<br>0.17 F244bb +<br>0.17 F245fa +<br>0.17TFP +<br>0.17 F1225yeZ +<br>0.17 F1225zc | Organics<br>0.95 F1233xf +<br>0.01 F244bb +<br>0.01 F245fa +<br>0.01 TFP +<br>0.01 F1225yeZ +<br>0.01 F1225zc | Organics<br>0.01 F1233xf +<br>0.95 F244bb +<br>0.01 F245fa +<br>0.01 TFP +<br>0.01 F1225yeZ +<br>0.01 F1225zc | Organics<br>0.01 F1233xf +<br>0.01 F244bb +<br>0.95 F245fa +<br>0.01 TFP +<br>0.01 F1225yeZ +<br>0.01 F1225zc |
|---|---|---|---|---|
| MASSFRAC HF | TOTAL PRESSURE bar | TOTAL PRESSURE bar | TOTAL PRESSURE bar | TOTAL PRESSURE bar |
| 0 | 4.8 | 1.8 | 0.9 | 1.7 |
| 0.05 | 5.9 | 2.9 | 2.1 | 2.8 |
| 0.1 | 5.9 | 2.9 | 2.1 | 2.8 |
| 0.15 | 5.9 | 2.9 | 2.1 | 2.8 |
| 0.2 | 5.9 | 2.9 | 2.1 | 2.8 |
| 0.25 | 5.9 | 2.9 | 2.1 | 2.8 |
| 0.3 | 5.8 | 2.9 | 2.1 | 2.8 |
| 0.35 | 5.8 | 2.9 | 2.1 | 2.8 |
| 0.4 | 5.8 | 2.9 | 2.1 | 2.8 |
| 0.45 | 5.8 | 2.9 | 2.0 | 2.8 |
| 0.5 | 5.8 | 2.9 | 2.0 | 2.8 |
| 0.55 | 5.7 | 2.8 | 2.0 | 2.8 |
| 0.6 | 5.7 | 2.8 | 2.0 | 2.8 |
| 0.65 | 5.6 | 2.8 | 2.0 | 2.8 |
| 0.7 | 5.6 | 2.8 | 2.0 | 2.8 |
| 0.75 | 5.5 | 2.8 | 2.0 | 2.8 |
| 0.8 | 5.2 | 2.7 | 2.0 | 2.7 |
| 0.85 | 4.7 | 2.5 | 2.0 | 2.5 |
| 0.9 | 4.0 | 2.2 | 1.8 | 2.2 |
| 0.95 | 2.8 | 1.8 | 1.6 | 1.8 |
| 1 | 1.2 | 1.2 | 1.2 | 1.2 |

-continued

| MASSFRAC HF | Organics 0.01 F1233xf + 0.01 F244bb + 0.01 F245fa + 0.95 TFP + 0.01 F1225yeZ + 0.01 F1225zc TOTAL PRESSURE bar | Organics 0.01 F1233xf + 0.01 F244bb + 0.01 F245fa + 0.01 TFP + 0.95 F1225yeZ + 0.01 F1225zc TOTAL PRESSURE bar | Organics 0.01F1233xf + 0.01 F244bb + 0.01 F245fa + 0.01 TFP + 0.01 F1225yeZ + 0.95 F1225zc TOTAL PRESSURE bar |
|---|---|---|---|
| 0 | 11.3 | 5.1 | 5.3 |
| 0.05 | 12.1 | 6.2 | 6.3 |
| 0.1 | 12.0 | 6.2 | 6.3 |
| 0.15 | 11.9 | 6.2 | 6.3 |
| 0.2 | 11.8 | 6.2 | 6.3 |
| 0.25 | 11.7 | 6.2 | 6.3 |
| 0.3 | 11.6 | 6.2 | 6.2 |
| 0.35 | 11.5 | 6.2 | 6.2 |
| 0.4 | 11.5 | 6.2 | 6.2 |
| 0.45 | 11.4 | 6.2 | 6.2 |
| 0.5 | 11.5 | 6.2 | 6.2 |
| 0.55 | 11.5 | 6.2 | 6.2 |
| 0.6 | 11.5 | 6.2 | 6.1 |
| 0.65 | 11.5 | 6.2 | 6.0 |
| 0.7 | 11.5 | 6.1 | 5.8 |
| 0.75 | 11.5 | 5.9 | 5.6 |
| 0.8 | 11.3 | 5.6 | 5.2 |
| 0.85 | 10.5 | 5.0 | 4.6 |
| 0.9 | 8.9 | 4.2 | 3.8 |
| 0.95 | 6.0 | 3.0 | 2.7 |
| 1 | 1.2 | 1.2 | 1.2 |

Example 14: Temperature and Pressure Range of System with 7 Compounds

| System with 7 compounds | Boiling point range | |
|---|---|---|
| | Temperature °C. | Pressure bar abs |
| HF-HCFO-1233xf-HFO-1234yf-HFC-245cb-HCFO-1233zdE-HFO-1234zeE-HFO-1234zeZ | 0 to 40 | ⁻0.9⁻11.5 |
| HF-HCFO-1233xf-HFO-1234yf-HFC-245cb-HCFO-1233zdE-HFO-1234zeE-HFO-1243zf | 0 to 40 | ⁻1.0 to ⁻11.6 |
| HF-HCFO-1233xf-HFO-1234yf-HFC-245cb-HCFO-1233zdE-HFO-1234zeZ-HFO-1243zf | 0 to 40 | ⁻0.9 to ⁻11.5 |
| HF-HCFO-1233xf-HFO-1234yf-HFC-245cb-HFO-1234zeE-HFO-1234zeZ-HFO-1243zf | 0 to 40 | ⁻1.1 to ⁻11.6 |
| HF-HCFO-1233xf-HFO-1234yf-HCFO-1233zdE-HFO-1234zeE-HFO-1234zeZ-HFO-1243zf | 0 to 40 | ⁻0.9 to ⁻11.5 |
| HF-HCFO-1233xf-HFC-245cb-HCFO-1233zdE-HFO-1234zeE-HFO-1234zeZ-HFO-1243zf | 0 to 40 | ⁻0.9 to ⁻10.3 |
| HF-HCFO-1233xf-HCFC-244bb-HFC-245fa-Trifluoropropyne-HFO-1225yeZ-HFO-1225zc | 0 to 40 | ⁻0.7 to ⁻17.5 |

Example 15: Decantation Range of System with 7 Compounds

| System with 7 compounds | Decantation ranges Mass percentage of HF | | |
|---|---|---|---|
| | Temp 0° C. | Temp 25° C. | Temp 40° C. |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HFC-245cb-HFO-1234zeE-HFO-1234zeZ-HFO-1243zf | 5-75 | 10-65 | * |

-continued

|  | Decantation ranges Mass percentage of HF | | |
|---|---|---|---|
| System with 7 compounds | Temp 0° C. | Temp 25° C. | Temp 40° C. |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HCFO-1233xf-HFC-245cb-HCFO-1233zdE-HFO-1234zeE-HFO-1234zeZ-HFO-1243zf | 5-75 | 5-70 | 10-55 |
| HF-HCFO-1233xf-HCFC-244bb-HFC-245fa-Trifluoropropyne-HFO-1225yeZ-HFO-1225zc | 1-80 | 20-99 | 5-75 |

Example 16: Systems with 8 Compounds

HF - HCFO-1233xf - HFO-1234yf - HFC-245cb - HCFO-1233zdE 5 - HFO-1234zeE - HFO-1234zeZ - HFO-1243zf

| Organics 0.01 F1233xf + 0.94 F1234yf + 0.01 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1234zeE + 0.01 F1234zeZ + 0.01 F1243zf | | Organics 0.01 F1233xf + 0.01 F1234yf + 0.01 F245cb + 0.94 F1233zdE + 0.01 F1234zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 4.6 | 0 | 1.5 | 0 | 4.8 |
| 0.05 | 7.6 | 0.05 | 5.8 | 0.05 | 2.6 | 0.05 | 5.8 |
| 0.1 | 7.6 | 0.1 | 5.8 | 0.1 | 2.6 | 0.1 | 5.8 |
| 0.15 | 7.6 | 0.15 | 5.8 | 0.15 | 2.6 | 0.15 | 5.8 |
| 0.2 | 7.6 | 0.2 | 5.8 | 0.2 | 2.6 | 0.2 | 5.8 |
| 0.25 | 7.6 | 0.25 | 5.8 | 0.25 | 2.6 | 0.25 | 5.8 |
| 0.3 | 7.6 | 0.3 | 5.8 | 0.3 | 2.6 | 0.3 | 5.8 |
| 0.35 | 7.6 | 0.35 | 5.8 | 0.35 | 2.6 | 0.35 | 5.8 |
| 0.4 | 7.6 | 0.4 | 5.8 | 0.4 | 2.6 | 0.4 | 5.8 |
| 0.45 | 7.6 | 0.45 | 5.8 | 0.45 | 2.6 | 0.45 | 5.8 |
| 0.5 | 7.6 | 0.5 | 5.8 | 0.5 | 2.6 | 0.5 | 5.7 |
| 0.55 | 7.6 | 0.55 | 5.8 | 0.55 | 2.6 | 0.55 | 5.7 |
| 0.6 | 7.6 | 0.6 | 5.8 | 0.6 | 2.6 | 0.6 | 5.6 |
| 0.65 | 7.6 | 0.65 | 5.8 | 0.65 | 2.6 | 0.65 | 5.5 |
| 0.7 | 7.5 | 0.7 | 5.8 | 0.7 | 2.6 | 0.7 | 5.4 |
| 0.75 | 7.4 | 0.75 | 5.8 | 0.75 | 2.6 | 0.75 | 5.1 |
| 0.8 | 7.1 | 0.8 | 5.8 | 0.8 | 2.5 | 0.8 | 4.8 |
| 0.85 | 6.5 | 0.85 | 5.8 | 0.85 | 2.3 | 0.85 | 4.3 |
| 0.9 | 5.5 | 0.9 | 5.0 | 0.9 | 2.1 | 0.9 | 3.6 |
| 0.95 | 3.8 | 0.95 | 3.5 | 0.95 | 1.7 | 0.95 | 2.6 |
| 1 | 1.2 | 1 | 1.2 | 1 | 1.2 | 1 | 1.2 |

| Organics 0.01 F1233xf + 0.01 F1234yf + 0.01F 245cb + 0.01 F1233zdE + 0.01 F1234zeE + 0.94 F1234zeZ + 0.01 F1243zf | | Organics 0.01 F1233xf + 0.01 F1234yf + 0.01 F245cb + 0.01 F1233zdE + 0.01 F1234zeE + 0.01 F1234zeZ + 0.94 F1243zf | | Organics 0.16 F1233xf + 0.14 F1234yf + 0.14 F245cb + 0.14 F1233zdE + 0.14 F1234zeE + 0.14 F1234zeZ + 0.14 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 2.0 | 0 | 5.7 | 0 | 3.9 |
| 0.05 | 3.1 | 0.05 | 6.7 | 0.05 | 5.0 |
| 0.1 | 3.1 | 0.1 | 6.7 | 0.1 | 5.0 |
| 0.15 | 3.1 | 0.15 | 6.7 | 0.15 | 5.0 |
| 0.2 | 3.1 | 0.2 | 6.7 | 0.2 | 5.0 |
| 0.25 | 3.1 | 0.25 | 6.7 | 0.25 | 5.0 |
| 0.3 | 3.1 | 0.3 | 6.7 | 0.3 | 5.0 |
| 0.35 | 3.1 | 0.35 | 6.7 | 0.35 | 5.0 |
| 0.4 | 3.1 | 0.4 | 6.7 | 0.4 | 5.0 |
| 0.45 | 3.1 | 0.45 | 6.7 | 0.45 | 5.0 |
| 0.5 | 3.1 | 0.5 | 6.7 | 0.5 | 5.0 |

-continued

| | | | | | |
|---|---|---|---|---|---|
| 0.55 | 3.1 | 0.55 | 6.7 | 0.55 | 5.0 |
| 0.6 | 3.1 | 0.6 | 6.6 | 0.6 | 5.0 |
| 0.65 | 3.1 | 0.65 | 6.6 | 0.65 | 5.0 |
| 0.7 | 3.1 | 0.7 | 6.5 | 0.7 | 5.0 |
| 0.75 | 3.1 | 0.75 | 6.3 | 0.75 | 4.9 |
| 0.8 | 2.9 | 0.8 | 6.0 | 0.8 | 4.6 |
| 0.85 | 2.7 | 0.85 | 5.5 | 0.85 | 4.2 |
| 0.9 | 2.4 | 0.9 | 4.7 | 0.9 | 3.6 |
| 0.95 | 1.9 | 0.95 | 3.3 | 0.95 | 2.6 |
| 1 | 1.2 | 1 | 1.2 | 1 | 1.2 |

HF-HFO-1234yf-HFC-245cb-HCFO-1233xf-HFO-1234zeE-HFO-1234zeZ-HCFO-1233zdE-HCFC-244bb

| MASSFRAC HF | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar |
|---|---|---|---|---|
| 0 | 1.7 | 6.6 | 4.5 | 1.5 |
| 0.05 | 2.8 | 7.5 | 5.7 | 2.6 |
| 0.1 | 2.8 | 7.5 | 5.7 | 2.6 |
| 0.15 | 2.8 | 7.5 | 5.7 | 2.6 |
| 0.2 | 2.8 | 7.5 | 5.7 | 2.6 |
| 0.25 | 2.8 | 7.5 | 5.7 | 2.6 |
| 0.3 | 2.8 | 7.5 | 5.7 | 2.6 |
| 0.35 | 2.8 | 7.5 | 5.7 | 2.6 |
| 0.4 | 2.8 | 7.5 | 5.7 | 2.6 |
| 0.45 | 2.8 | 7.5 | 5.7 | 2.6 |
| 0.5 | 2.8 | 7.5 | 5.7 | 2.6 |
| 0.55 | 2.8 | 7.5 | 5.7 | 2.6 |
| 0.6 | 2.8 | 7.5 | 5.7 | 2.6 |
| 0.65 | 2.8 | 7.5 | 5.7 | 2.6 |
| 0.7 | 2.8 | 7.5 | 5.7 | 2.6 |
| 0.75 | 2.8 | 7.4 | 5.7 | 2.6 |
| 0.8 | 2.6 | 7.0 | 5.7 | 2.4 |
| 0.85 | 2.4 | 6.5 | 5.7 | 2.3 |
| 0.9 | 2.2 | 5.4 | 4.9 | 2.0 |
| 0.95 | 1.8 | 3.8 | 3.5 | 1.7 |
| 1 | 1.2 | 1.2 | 1.2 | 1.2 |

| MASSFRAC HF | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.01 F1234zeZ + 0.94 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
|---|---|---|---|---|
| 0 | 4.8 | 1.9 | 0.8 | 3.2 |
| 0.05 | 5.7 | 3.0 | 2.0 | 4.3 |
| 0.1 | 5.7 | 3.0 | 2.0 | 4.3 |
| 0.15 | 5.7 | 3.0 | 2.0 | 4.3 |
| 0.2 | 5.7 | 3.0 | 2.0 | 4.3 |
| 0.25 | 5.7 | 3.0 | 2.0 | 4.3 |
| 0.3 | 5.7 | 3.0 | 2.0 | 4.3 |
| 0.35 | 5.7 | 3.0 | 2.0 | 4.3 |
| 0.4 | 5.7 | 3.0 | 2.0 | 4.3 |
| 0.45 | 5.7 | 3.0 | 2.0 | 4.3 |
| 0.5 | 5.7 | 3.0 | 2.0 | 4.3 |
| 0.55 | 5.6 | 3.0 | 2.0 | 4.2 |
| 0.6 | 5.6 | 3.0 | 2.0 | 4.2 |
| 0.65 | 5.5 | 3.0 | 2.0 | 4.2 |
| 0.7 | 5.3 | 3.0 | 2.0 | 4.2 |
| 0.75 | 5.1 | 3.0 | 1.9 | 4.2 |
| 0.8 | 4.7 | 2.9 | 1.9 | 4.0 |
| 0.85 | 4.3 | 2.7 | 1.9 | 3.7 |
| 0.9 | 3.6 | 2.4 | 1.8 | 3.2 |

| | | | | |
|---|---|---|---|---|
| 0.95 | 2.6 | 1.9 | 1.6 | 2.4 |
| 1 | 1.2 | 1.2 | 1.2 | 1.2 |

HF-HFO-1234yf-HFC-245cb-HCFO-1233xf-HFO-1234zeE-5 HFO-1234zeZ-HCFO-1233zdE-Trifluoropropyne

| MASSFRAC HF | Organics 0.16 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar |
|---|---|---|---|---|
| 0 | 5.0 | 6.7 | 4.7 | 1.8 |
| 0.05 | 6.0 | 7.6 | 5.8 | 2.9 |
| 0.1 | 6.0 | 7.6 | 5.8 | 2.9 |
| 0.15 | 6.0 | 7.6 | 5.8 | 2.9 |
| 0.2 | 6.0 | 7.6 | 5.8 | 2.9 |
| 0.25 | 6.0 | 7.6 | 5.8 | 2.9 |
| 0.3 | 6.0 | 7.6 | 5.8 | 2.9 |
| 0.35 | 6.0 | 7.6 | 5.8 | 2.9 |
| 0.4 | 6.0 | 7.6 | 5.8 | 2.9 |
| 0.45 | 6.0 | 7.6 | 5.8 | 2.9 |
| 0.5 | 6.0 | 7.6 | 5.8 | 2.9 |
| 0.55 | 6.0 | 7.6 | 5.8 | 2.9 |
| 0.6 | 6.0 | 7.6 | 5.8 | 2.9 |
| 0.65 | 6.0 | 7.6 | 5.8 | 2.9 |
| 0.7 | 6.0 | 7.6 | 5.8 | 2.9 |
| 0.75 | 5.9 | 7.5 | 5.8 | 2.9 |
| 0.8 | 5.6 | 7.1 | 5.8 | 2.8 |
| 0.85 | 5.1 | 6.6 | 5.8 | 2.6 |
| 0.9 | 4.3 | 5.5 | 5.0 | 2.2 |
| 0.95 | 3.1 | 3.8 | 3.5 | 1.8 |
| 1 | 1.2 | 1.2 | 1.2 | 1.2 |

| MASSFRAC HF | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 TPF TOTAL PRESSURE bar |
|---|---|---|---|---|
| 0 | 4.9 | 2.0 | 1.6 | 11.2 |
| 0.05 | 5.8 | 3.1 | 2.7 | 12.0 |
| 0.1 | 5.9 | 3.1 | 2.7 | 11.9 |
| 0.15 | 5.9 | 3.1 | 2.7 | 11.8 |
| 0.2 | 5.9 | 3.1 | 2.7 | 11.7 |
| 0.25 | 5.8 | 3.1 | 2.7 | 11.6 |
| 0.3 | 5.8 | 3.1 | 2.7 | 11.5 |
| 0.35 | 5.8 | 3.1 | 2.7 | 11.5 |
| 0.4 | 5.8 | 3.1 | 2.7 | 11.4 |
| 0.45 | 5.8 | 3.1 | 2.7 | 11.4 |
| 0.5 | 5.8 | 3.1 | 2.7 | 11.4 |
| 0.55 | 5.8 | 3.1 | 2.7 | 11.5 |
| 0.6 | 5.7 | 3.1 | 2.7 | 11.5 |
| 0.65 | 5.6 | 3.1 | 2.7 | 11.5 |
| 0.7 | 5.4 | 3.1 | 2.7 | 11.5 |
| 0.75 | 5.2 | 3.1 | 2.7 | 11.5 |
| 0.8 | 4.9 | 3.0 | 2.6 | 11.2 |
| 0.85 | 4.4 | 2.8 | 2.4 | 10.4 |
| 0.9 | 3.6 | 2.4 | 2.1 | 8.8 |
| 0.95 | 2.6 | 1.9 | 1.7 | 5.9 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HFC-245fa

| MASSFRAC HF | Organics<br>0.16 F1234yf +<br>0.14 F245cb +<br>0.14 F1233xf +<br>0.14 F1234zeE +<br>0.14 F1234zeZ +<br>0.14 F1233zdE +<br>0.14 F245fa<br>TOTAL PRESSURE bar | Organics<br>0.94 F1234yf +<br>0.01 F245cb +<br>0.01 F1233xf +<br>0.01 F1234zeE +<br>0.01 F1234zeZ +<br>0.01 F1233zdE +<br>0.01 F245fa<br>TOTAL PRESSURE bar | Organics<br>0.01 F1234yf +<br>0.94 F245cb +<br>0.01 F1233xf +<br>0.01 F1234zeE +<br>0.01 F1234zeZ +<br>0.01 F1233zdE +<br>0.01 F245fa<br>TOTAL PRESSURE bar | Organics<br>0.01 F1234yf +<br>0.01 F245cb +<br>0.94 F1233xf +<br>0.01 F1234zeE +<br>0.01 F1234zeZ +<br>0.01 F1233zdE +<br>0.01 F245fa<br>TOTAL PRESSURE bar |
|---|---|---|---|---|
| 0 | 3.4 | 6.6 | 4.5 | 1.7 |
| 0.05 | 4.5 | 7.5 | 5.7 | 2.8 |
| 0.1 | 4.5 | 7.5 | 5.7 | 2.8 |
| 0.15 | 4.5 | 7.5 | 5.7 | 2.8 |
| 0.2 | 4.5 | 7.5 | 5.7 | 2.8 |
| 0.25 | 4.5 | 7.5 | 5.7 | 2.8 |
| 0.3 | 4.5 | 7.5 | 5.7 | 2.8 |
| 0.35 | 4.5 | 7.5 | 5.7 | 2.8 |
| 0.4 | 4.5 | 7.5 | 5.7 | 2.8 |
| 0.45 | 4.5 | 7.5 | 5.7 | 2.8 |
| 0.5 | 4.5 | 7.5 | 5.7 | 2.8 |
| 0.55 | 4.5 | 7.5 | 5.7 | 2.8 |
| 0.6 | 4.5 | 7.5 | 5.7 | 2.8 |
| 0.65 | 4.5 | 7.5 | 5.7 | 2.8 |
| 0.7 | 4.5 | 7.5 | 5.7 | 2.8 |
| 0.75 | 4.4 | 7.4 | 5.7 | 2.8 |
| 0.8 | 4.2 | 7.1 | 5.8 | 2.6 |
| 0.85 | 3.9 | 6.5 | 5.7 | 2.5 |
| 0.9 | 3.3 | 5.4 | 4.9 | 2.2 |
| 0.95 | 2.4 | 3.8 | 3.5 | 1.8 |
| 1 | 1.2 | 1.2 | 1.2 | 1.2 |

| MASSFRAC HF | Organics<br>0.01 F1234yf +<br>0.01 F245cb +<br>0.01 F1233xf +<br>0.94 F1234zeE +<br>0.01 F1234zeZ +<br>0.01 F1233zdE +<br>0.01 F245fa<br>TOTAL PRESSURE bar | Organics<br>0.01 F1234yf +<br>0.01 F245cb +<br>0.01 F1233xf +<br>0.01 F1234zeE +<br>0.94 F1234zeZ +<br>0.01 F1233zdE +<br>0.01 F245fa<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.94 F1233zdE +<br>0.01 F245fa<br>TOTAL PRESSURE bar | Organics<br>0.01 F1234yf +<br>0.01 F245cb +<br>0.01 F1233xf +<br>0.01 F1234zeE +<br>0.01 F1234zeZ +<br>0.01 F1233zdE +<br>0.94 F245fa<br>TOTAL PRESSURE bar |
|---|---|---|---|---|
| 0 | 4.8 | 1.9 | 1.5 | 1.6 |
| 0.05 | 5.7 | 3.0 | 2.6 | 2.8 |
| 0.1 | 5.7 | 3.0 | 2.6 | 2.8 |
| 0.15 | 5.7 | 3.0 | 2.6 | 2.8 |
| 0.2 | 5.7 | 3.0 | 2.6 | 2.8 |
| 0.25 | 5.7 | 3.0 | 2.6 | 2.8 |
| 0.3 | 5.7 | 3.0 | 2.6 | 2.8 |
| 0.35 | 5.7 | 3.0 | 2.6 | 2.8 |
| 0.4 | 5.7 | 3.0 | 2.6 | 2.8 |
| 0.45 | 5.7 | 3.0 | 2.6 | 2.8 |
| 0.5 | 5.7 | 3.0 | 2.6 | 2.8 |
| 0.55 | 5.6 | 3.0 | 2.6 | 2.8 |
| 0.6 | 5.6 | 3.0 | 2.6 | 2.8 |
| 0.65 | 5.5 | 3.0 | 2.6 | 2.8 |
| 0.7 | 5.3 | 3.0 | 2.6 | 2.8 |
| 0.75 | 5.1 | 3.0 | 2.6 | 2.8 |
| 0.8 | 4.7 | 2.9 | 2.5 | 2.7 |
| 0.85 | 4.3 | 2.7 | 2.3 | 2.5 |
| 0.9 | 3.6 | 2.4 | 2.0 | 2.2 |
| 0.95 | 2.6 | 1.9 | 1.7 | 1.8 |
| 1 | 1.2 | 1.2 | 1.2 | 1.2 |

HF-HFO-1234yf-HFC-245cb-HCFO-1233xf-HFO-1234zeE-5 HFO-1234zeZ-HCFO-1233zdE-HFO-1225yeZ

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225yeZ TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225yeZ TOTAL PRESSURE bar |
|---|---|---|---|---|
| 0 | 3.8 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.5 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 5.0 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.6 | 5.5 | 4.9 | 2.2 |
| 0.95 | 2.6 | 3.8 | 3.5 | 1.8 |
| 1 | 1.2 | 1.2 | 1.2 | 1.2 |

| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225yeZ TOTAL PRESSURE bar |
|---|---|---|---|---|
| 0 | 4.8 | 1.9 | 1.5 | 5.1 |
| 0.05 | 5.8 | 3.0 | 2.6 | 6.1 |
| 0.1 | 5.8 | 3.0 | 2.6 | 6.1 |
| 0.15 | 5.8 | 3.0 | 2.6 | 6.1 |
| 0.2 | 5.8 | 3.0 | 2.6 | 6.1 |
| 0.25 | 5.8 | 3.0 | 2.6 | 6.1 |
| 0.3 | 5.8 | 3.0 | 2.6 | 6.1 |
| 0.35 | 5.8 | 3.0 | 2.6 | 6.1 |
| 0.4 | 5.8 | 3.0 | 2.6 | 6.1 |
| 0.45 | 5.8 | 3.0 | 2.6 | 6.1 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.1 |
| 0.65 | 5.5 | 3.0 | 2.6 | 6.1 |
| 0.7 | 5.3 | 3.0 | 2.6 | 6.0 |
| 0.75 | 5.1 | 3.0 | 2.6 | 5.8 |
| 0.8 | 4.8 | 2.9 | 2.5 | 5.5 |
| 0.85 | 4.3 | 2.7 | 2.3 | 5.0 |
| 0.9 | 3.6 | 2.4 | 2.1 | 4.2 |
| 0.95 | 2.6 | 1.9 | 1.7 | 2.9 |
| 1 | 1.2 | 1.2 | 1.2 | 1.2 |

-continued

HF-HFO-1234yf-HFC-245cb-HCFO-1233xf-HFO-1234zeE-HFO-1234zeZ-HCFC-1233zdE-HFO-1225zc

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225zc TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225zc TOTAL PRESSURE bar |
|---|---|---|---|---|
| 0 | 3.9 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.6 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 4.9 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.5 | 5.5 | 4.9 | 2.2 |
| 0.95 | 2.6 | 3.8 | 3.5 | 1.8 |
| 1 | 1.2 | 1.2 | 1.2 | 1.2 |

| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225zc TOTAL PRESSURE bar |
|---|---|---|---|---|
| 0 | 4.8 | 1.9 | 1.5 | 5.2 |
| 0.05 | 5.8 | 3.0 | 2.6 | 6.2 |
| 0.1 | 5.8 | 3.0 | 2.6 | 6.2 |
| 0.15 | 5.8 | 3.0 | 2.6 | 6.2 |
| 0.2 | 5.8 | 3.0 | 2.6 | 6.2 |
| 0.25 | 5.8 | 3.0 | 2.6 | 6.2 |
| 0.3 | 5.8 | 3.0 | 2.6 | 6.2 |
| 0.35 | 5.8 | 3.0 | 2.6 | 6.2 |
| 0.4 | 5.8 | 3.0 | 2.6 | 6.2 |
| 0.45 | 5.8 | 3.0 | 2.6 | 6.2 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.0 |
| 0.65 | 5.5 | 3.0 | 2.6 | 5.9 |
| 0.7 | 5.3 | 3.0 | 2.6 | 5.8 |
| 0.75 | 5.1 | 3.0 | 2.6 | 5.5 |
| 0.8 | 4.8 | 2.9 | 2.5 | 5.1 |
| 0.85 | 4.3 | 2.7 | 2.3 | 4.6 |
| 0.9 | 3.6 | 2.4 | 2.1 | 3.8 |
| 0.95 | 2.6 | 1.9 | 1.7 | 2.7 |
| 1 | 1.2 | 1.2 | 1.2 | 1.2 |

Example 17: Temperature and Pressure Range of System with 5 to 8 Compounds

| System with 8 compounds | Boiling point range | |
|---|---|---|
| | Temperature ° C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ⁻1.0⁻11.5 |
| HF-HFO-1234yf-HFC-245cb-HCFO-1233xf-HFO-1234zeE-HFO-1234zeZ-HCFO-1233zdE-HCFC-244bb | 0 to 40 | ⁻0.7 to ⁻11.5 |
| HF-HFO-1234yf-HFC-245cb-HCFO-1233xf-HFO-1234zeE-HFO-1234zeZ-HCFO-1233zdE-Trifluoropropyne | 0 to 40 | ⁻1.0 to ⁻17.4 |
| HF-HFO-1234yf-HFC-245cb-HCFO-1233xf-HFO-1234zeE-HFO-1234zeZ-HCFO-1233zdE-HFC-245fa | 0 to 40 | ⁻0.9 to ⁻11.5 |
| HF-HFO-1234yf-HFC-245cb-HCFO-1233xf-HFO-1234zeE-HFO-1234zeZ-HCFO-1233zdE-HFO-1225yeZ | 0 to 40 | ⁻1.0 to ⁻11.5 |
| HF-HFO-1234yf-HFC-245cb-HCFO-1233xf-HFO-1234zeE-HFO-1234zeZ-HCFC-1233zdE-HFO-1225zc | 0 to 40 | ⁻1.0 to ⁻11.5 |

Example 18: Decantation Ranges of System with 8 Compounds

| System with 8 compounds | Decantation ranges Mass percentage of HF Temperature | | |
|---|---|---|---|
| | 0° C. | 25° C. | 40° C. |
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-1234zeE-HFO-1234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

Example 19: Systems with 13 Compounds

| | HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-5 HFO-1225zc | | | | |
|---|---|---|---|---|---|
| MASSFRAC HF | Organics 0.087 F1234yf + 0.083 F245cb + F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |

| | HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-5 HFO-1225zc | | | | |
|---|---|---|---|---|---|
| | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc |
| MASSFRAC HF | TOTAL PRESSURE bar | TOTAL PRESSURE bar | TOTAL PRESSURE bar | TOTAL PRESSURE bar | TOTAL PRESSURE bar |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

Example 20: Temperature and Pressure Range of System with 13 Compounds

| | Boiling point range | |
|---|---|---|
| System with 13 compounds | Temperature °C. | Pressure bar abs |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 0 to 40 | ⁻0.7⁻18.0 |

Example 21: Decantation Ranges of System with 13 Compounds

| | Decantation ranges Mass percentage of HF Temperature | | |
|---|---|---|---|
| System with 13 compounds | 0° C. | 25° C. | 40° C. |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 5-75% | 10-70% | 15-60% |

EMBODIMENTS

1. An azeotropic or quasi-azeotropic composition comprising hydrogen fluoride, 3,3,3-trifluoro-2-chloropropene and one or more (hydro)halocarbon compounds comprising between 1 and 3 carbon atoms.

2. The composition as in embodiment 1, in which it comprises hydrogen fluoride, 3,3,3-trifluoro-2-chloropropene, and one or more compounds chosen from E-1,3,3,3-tetrafluoropropene, Z-1,3,3,3-tetrafluoropropene, 3,3,3-trifluoropropene, 2,3,3,3-tetrafluoropropene, E-3,3,3-trifluoro-1-chloropropene, trifluoropropyne, 1,1,1,3,3-pentafluoropropane, 1,1,1,3,3-pentafluoropropene, 1,1,1,2,2-pentafluoropropane, 2-chloro,1,1,1,2-tetrafluoropropane and 1,1,1,2,3-pentafluoropropane.

3. The composition as in embodiment 1 or 2, in which it comprises hydrogen fluoride, 3,3,3-trifluoro-2-chloropropene and at least one or more organic compounds chosen from 1,1,1,2,2-pentafluoropropane, E-3,3,3-trifluoro-1-chloropropene, E-1,3,3,3-tetrafluoropropene, Z-1,3,3,3-tetrafluoropropene, 3,3,3-trifluoropropene and 2,3,3,3-tetrafluoropropene.

4. The composition as in any one of the preceding embodiments, in which it is heteroazeotropic or quasi-heteroazeotropic.

5. The composition as in any one of the preceding embodiments, in which it comprises hydrogen fluoride, 3,3,3-trifluoro-2-chloropropene, E-3,3,3-trifluoro-1-chloropropene and optionally one or more organic compounds chosen from E-1,3,3,3-tetrafluoropropene, Z-1,3,3,3-tetrafluoropropene, 3,3,3-trifluoropropene, 1,1,1,2,2-pentafluoropropane and 2,3,3,3-tetrafluoropropene.

6. The composition as in any one of the preceding embodiments, in which it comprises hydrogen fluoride, 3,3,3-trifluoro-2-chloropropene, E-1,3,3,3-tetrafluoropropene and optionally one or more organic compounds chosen from Z-1,3,3,3-tetrafluoropropene, 3,3,3-trifluoropropene, 1,1,1,2,2-pentafluoropropane and 2,3,3,3-tetrafluoropropene.

7. The composition as in any one of the preceding embodiments, in which it comprises a hydrogen fluoride, 3,3,3-trifluoro-2-chloropropene, Z-1,3,3,3-tetrafluoropropene and optionally one or more organic compounds chosen from 3,3,3-trifluoropropene, 1,1,1,2,2-pentafluoropropane and 2,3,3,3-tetrafluoropropene.

8. The composition as in any one of the preceding embodiments, in which it comprises hydrogen fluoride, 3,3,3-trifluoro-2-chloropropene, 3,3,3-trifluoropropene and optionally one or more organic compounds chosen from 1,1,1,2,2-pentafluoropropane and 2,3,3,3-tetrafluoropropene.

9. The composition as in any one of the preceding embodiments, in which it comprises hydrogen fluoride, 3,3,3-trifluoro-2-chloropropene, 1,1,1,2,2-pentafluoropropane and 2,3,3,3-tetrafluoropropene.

10. The composition as in any one of the preceding embodiments, in which it comprises hydrogen fluoride, 3,3,3-trifluoro-2-chloropropene and 2,3,3,3-tetrafluoropropene.

11. The composition as in any one of the preceding embodiments, in which the composition comprises from 1% to 85% by weight of hydrogen fluoride and from 99% to 15% by weight of the sum of the organic compounds.

12. The composition as in any one of the preceding embodiments, in which the composition comprises from 5% to 80% by weight of hydrogen fluoride and from 95% to 20% by weight of the sum of the organic compounds.

13. The composition as in any one of the preceding embodiments, in which the boiling point of said composition is between −20° C. and 80° C., and at a pressure of between 0.1 and 44 bar absolute, preferentially between 0° C. and 40° C. and preferentially at a pressure of between 0.7 and 18 bar absolute, advantageously between 0.9 and 12.5 bar absolute.

The invention claimed is:

1. An azeotropic or quasi-azeotropic composition comprising:
   hydrogen fluoride,
   3,3,3-trifluoro-2-chloropropene, and
   one or more (hydro)halocarbon compounds selected from:
      the group consisting of chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene; or
      the group consisting of 1,1,1,3,3-pentafluoropropane and Z-3,3,3-trifluoro-1-chloropropene.

2. The azeotropic or quasi-azeotropic composition according to claim 1, wherein the one or more (hydro)halocarbon compounds is selected from the group consisting of chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

3. The azeotropic or quasi-azeotropic composition according to claim 2, further comprising E-3,3,3-trifluoro-1-chloropropene.

4. The azeotropic or quasi-azeotropic composition according to claim 2, in which the composition comprises from 1% to 85% by weight of hydrogen fluoride and from 99% to 15% by weight of the sum of the organic compounds.

5. The azeotropic or quasi-azeotropic composition according to claim 2, in which the composition comprises from 5% to 80% by weight of hydrogen fluoride and from 95% to 20% by weight of the sum of the organic compounds.

6. The azeotropic or quasi-azeotropic composition according to claim 2, in which the boiling point of said composition is between −20° C. and 80° C., and at a pressure of between 0.1 and 44 bar absolute.

7. The azeotropic or quasi-azeotropic composition according to claim 2, in which the boiling point of said composition is between 0° C. and 40° C. and at a pressure of between 0.7 and 18 bar absolute.

8. The azeotropic or quasi-azeotropic composition according to claim 2, in which the boiling point of said composition is between 0° C. and 40° C. and at a pressure of between 0.9 and 12.5 bar absolute.

9. The azeotropic or quasi-azeotropic composition according to claim 1, wherein the one or more (hydro)halocarbon compounds is selected from the group consisting of 1,1,1,3,3-pentafluoropropane, and Z-3,3,3-trifluoro-1-chloropropene.

10. The azeotropic or quasi-azeotropic composition according to claim 9, further comprising E-3,3,3-trifluoro-1-chloropropene.

11. The azeotropic or quasi-azeotropic composition according to claim 9, in which the composition comprises from 1% to 85% by weight of hydrogen fluoride and from 99% to 15% by weight of the sum of the organic compounds.

12. The azeotropic or quasi-azeotropic composition according to claim 9, in which the composition comprises from 5% to 80% by weight of hydrogen fluoride and from 95% to 20% by weight of the sum of the organic compounds.

13. The azeotropic or quasi-azeotropic composition according to claim 9, in which the boiling point of said composition is between −20° C. and 80° C., and at a pressure of between 0.1 and 44 bar absolute.

14. The azeotropic or quasi-azeotropic composition according to claim 9, in which the boiling point of said composition is between 0° C. and 40° C. and at a pressure of between 0.7 and 18 bar absolute.

15. The azeotropic or quasi-azeotropic composition according to claim 9, in which the boiling point of said composition is between 0° C. and 40° C. and at a pressure of between 0.9 and 12.5 bar absolute.

16. An azeotropic or quasi-azeotropic composition comprising:
   hydrogen fluoride,
   3,3,3-trifluoro-2-chloropropene
   E-3,3,3-trifluoro-1-chloropropene, and
   one or more (hydro)halocarbon compounds selected from:
      the group consisting of chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene; or
      the group consisting of 1,1,1,3,3-pentafluoropropane, Z-3,3,3-trifluoro-1-chloropropene, and 2-chloro-1,1,1,2-tetrafluoropropane.

* * * * *